US012496304B2

(12) United States Patent
Wolff-Winiski et al.

(10) Patent No.: US 12,496,304 B2
(45) Date of Patent: Dec. 16, 2025

(54) SELECTIVE GLUCOCORTICOID RECEPTOR MODIFIERS FOR TREATING IMPAIRED SKIN WOUND HEALING

(71) Applicant: AKRIBES BIOMEDICAL GMBH, Vienna (AT)

(72) Inventors: Barbara Wolff-Winiski, Vienna (AT); Anton Stütz, Vienna (AT); Nicole Schöfmann, Vienna (AT); Petra Dörfler, Vienna (AT)

(73) Assignee: AKRIBES BIOMEDICAL GMBH, Vienna (AT)

( * ) Notice: Subject to any disclaimer, the term of this patent is extended or adjusted under 35 U.S.C. 154(b) by 379 days.

(21) Appl. No.: 17/380,855

(22) Filed: Jul. 20, 2021

(65) Prior Publication Data

US 2022/0047602 A1 Feb. 17, 2022

Related U.S. Application Data

(63) Continuation of application No. PCT/EP2020/051457, filed on Jan. 22, 2020.

(30) Foreign Application Priority Data

Jan. 22, 2019 (EP) .................................... 19153026
Apr. 18, 2019 (EP) .................................... 19170117

(51) Int. Cl.

| | |
|---|---|
| ***A61K 31/536*** | (2006.01) |
| ***A61K 31/416*** | (2006.01) |
| ***A61K 31/437*** | (2006.01) |
| ***A61K 31/4525*** | (2006.01) |
| ***A61K 31/4709*** | (2006.01) |
| ***A61P 17/02*** | (2006.01) |
| ***G01N 33/50*** | (2006.01) |

(52) U.S. Cl.

CPC .......... *A61K 31/536* (2013.01); *A61K 31/416* (2013.01); *A61K 31/437* (2013.01); *A61K 31/4525* (2013.01); *A61K 31/4709* (2013.01); *A61P 17/02* (2018.01); *G01N 33/5023* (2013.01); *G01N 33/5041* (2013.01); *G01N 33/5044* (2013.01); *G01N 2333/54* (2013.01); *G01N 2333/705* (2013.01); *G01N 2333/78* (2013.01)

(58) Field of Classification Search

CPC .. A61K 31/536; A61K 31/416; A61K 31/437; A61K 31/4525; A61K 31/4709; A61K 31/4439; A61K 31/4704; A61K 31/4725; A61K 31/5355; A61P 17/02; G01N 33/5023; G01N 33/5041; G01N 33/5044; G01N 2333/54; G01N 2333/705; G01N 2333/78; G01N 33/6881; G01N 2333/545; G01N 2800/52; C07D 405/12; C07D 405/14; C07D 413/12; C07D 471/04

See application file for complete search history.

(56) References Cited

U.S. PATENT DOCUMENTS

| | | | | |
|---|---|---|---|---|
| 8,282,909 B2 | | 10/2012 | Steckel et al. | |
| 2005/0282903 A1 | * | 12/2005 | Wade .................. | A61K 31/557 514/573 |
| 2007/0281959 A1 | * | 12/2007 | Zhi ......................... | A61P 35/00 514/285 |
| 2009/0016969 A1 | * | 1/2009 | Steckel .................. | A61K 47/14 424/45 |
| 2009/0318355 A1 | * | 12/2009 | Chen ...................... | A61K 38/30 514/1.1 |
| 2011/0003797 A1 | * | 1/2011 | Dankulich .............. | A61P 29/00 540/603 |
| 2013/0171273 A1 | * | 7/2013 | Al-Mulla ............. | A61K 31/433 424/722 |
| 2023/0285361 A1 | * | 9/2023 | Hunt .................... | A61K 31/337 514/405 |

FOREIGN PATENT DOCUMENTS

| | | | |
|---|---|---|---|
| EP | 2062880 | A1 | 5/2009 |
| EP | 2300472 | B1 | 1/2012 |
| EP | 3312608 | A1 | 4/2018 |
| EP | 3639855 | A1 | 4/2020 |
| WO | 2000066522 | A1 | 11/2000 |
| WO | 2003086294 | A2 | 10/2003 |
| WO | 2004026248 | A2 | 4/2004 |
| WO | 2004066920 | A2 | 8/2004 |

(Continued)

OTHER PUBLICATIONS

Kirker KR, James GA. In vitro studies evaluating the effects of biofilms on wound-healing cells: a review. APMIS. Apr. 2017;125(4): 344-352. (Year: 2017).*

Krzyszczyk P, Schloss R, Palmer A, Berthiaume F. The Role of Macrophages in Acute and Chronic Wound Healing and Interventions to Promote Pro-wound Healing Phenotypes. Front Physiol. May 1, 2018;9:419. (Year: 2018).*

Han et al. Chronic Wound Healing: A Review of Current Management and Treatments. Adv. Ther 34, 599-610. Published 2017. (Year: 2017).*

(Continued)

*Primary Examiner* — James H Alstrum-Acevedo
*Assistant Examiner* — Lauren Wells
(74) *Attorney, Agent, or Firm* — Greenberg Traurig, LLP; Melissa Hunter-Ensor; Scott Goncher

(57) ABSTRACT

The present invention relates to a Selective Glucocorticoid Receptor Modulator (SEGRM), or a pharmaceutically acceptable salt thereof, for use in the treatment of impaired skin wound healing in a subject, an in vitro method for identifying a subject suffering from impaired skin wound healing to be responsive to the treatment with a Selective Glucocorticoid Receptor Modulator (SEGRM), or a pharmaceutically acceptable salt thereof, and kits and kits-of-part related thereto.

14 Claims, 19 Drawing Sheets

Figure 1:
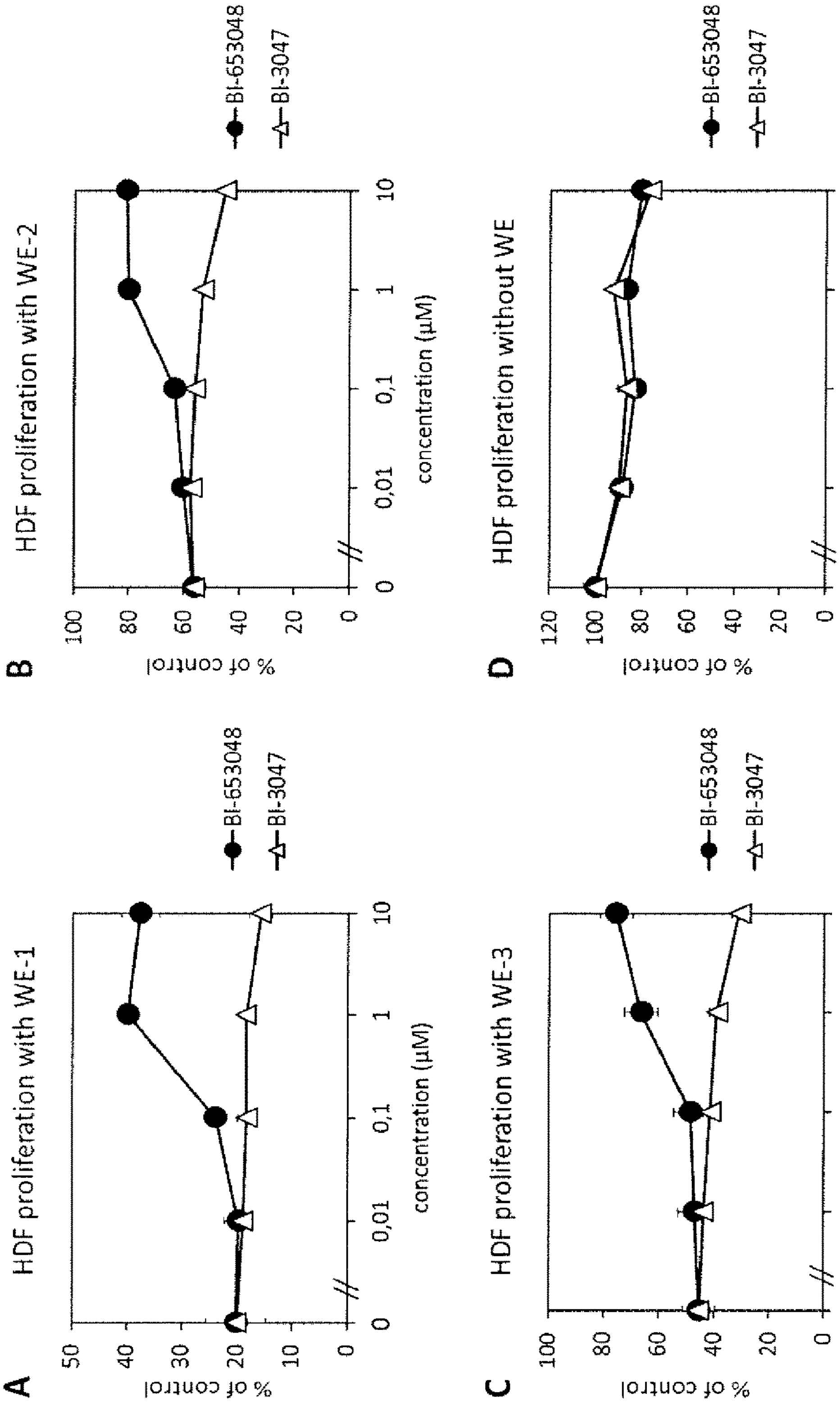

Specification includes a Sequence Listing.

(56) References Cited

FOREIGN PATENT DOCUMENTS

| | | | |
|---|---|---|---|
| WO | 2004075840 | A2 | 9/2004 |
| WO | 2004093805 | A2 | 11/2004 |
| WO | 2005082909 | A1 | 9/2005 |
| WO | 2006019716 | A1 | 2/2006 |
| WO | 2006050998 | A1 | 5/2006 |
| WO | 2008005686 | A2 | 1/2008 |
| WO | 2008021728 | A2 | 2/2008 |
| WO | 2008021729 | A2 | 2/2008 |
| WO | 2008027796 | A2 | 3/2008 |
| WO | 2008033655 | A2 | 3/2008 |
| WO | 2008076048 | A1 | 6/2008 |
| WO | 2008154129 | A1 | 12/2008 |
| WO | 2009023471 | A2 | 2/2009 |
| WO | 2009042377 | A1 | 4/2009 |
| WO | 2009065503 | A1 | 5/2009 |
| WO | 2009103007 | A2 | 8/2009 |
| WO | 2009108525 | A2 | 9/2009 |
| WO | 2009111214 | A1 | 9/2009 |
| WO | 2009149139 | A1 | 12/2009 |
| WO | 2010123769 | A1 | 10/2010 |
| WO | 2010138421 | A1 | 12/2010 |
| WO | 2010141247 | A1 | 12/2010 |
| WO | 2011031574 | A1 | 3/2011 |
| WO | 2011053567 | A1 | 5/2011 |
| WO | 2012170175 | A1 | 12/2012 |
| WO | 2013126156 | A1 | 8/2013 |
| WO | 2017046096 | A1 | 3/2017 |
| WO | 2018046678 | A1 | 3/2018 |
| WO | 2018046685 | A1 | 3/2018 |
| WO | 2018049255 | A1 | 3/2018 |
| WO | 2018077792 | A1 | 5/2018 |
| WO | 2018183947 | A1 | 10/2018 |
| WO | 2018/197461 | A1 | 11/2018 |
| WO | 2018230713 | A1 | 12/2018 |
| WO | 2018236749 | A2 | 12/2018 |

OTHER PUBLICATIONS

Stolte et al. Evolution of glucocorticoid receptors with different glucocorticoid sensitivity. Journal of Endocrinology. vol. 190: Iss 1. Published 2006. (Year: 2006).*

Klubo-Gwiezdzinska et al. Combined Immunosuppressive Therapy Induces Remission in Patients With Severe Type B Insulin Resistance: A Prospective. Diabetes Care. vol. 4, Nov. 2018. (Year: 2018).*

Tecilazich, F., Dinh, T. L., & Veves, A. (2013). Emerging drugs for the treatment of diabetic ulcers. Expert Opinion on Emerging Drugs, 18(2), 207-217. https://doi.org/10.1517/14728214.2013.802305 (Year: 2017).*

Vollmer TR, Stockhausen A, Zhang JZ. Anti-inflammatory effects of mapracorat, a novel selective glucocorticoid receptor agonist, is partially mediated by MAP kinase phosphatase-1 (MKP-1). J Biol Chem. Oct. 12, 2012;287(42):35212-35221. (Year: 2012).*

MedKoo. Mapracorat. Retrieved from the Wayback Machine on Jun. 26, 2024. Published Feb. 26, 2017. (Year: 2017).*

Ndip A, Ebah L, Mbako A. Neuropathic diabetic foot ulcers—evidence-to-practice. Int J Gen Med. 2012;5:129-34. doi: 10.2147/IJGM.S10328. Epub Feb. 10, 2012. (Year: 2012).*

Santema TB, Poyck PP, Ubbink DT. Skin grafting and tissue replacement for treating foot ulcers in people with diabetes. Cochrane Database Syst Rev. Feb. 11, 2016;2(2):CD011255. (Year: 2016).*

Akkus et al., “Effect of Carnitine on Cutaneous Wound Healing in Immunosuppressed Rats,” Journal of Surgical Research, Aug. 2009, vol. 155, No. 2, pp. 301-305.

International Search Report and Written Opinion in International Patent Application No. PCT/EP2020/051457, mailed May 8, 2020 (18 pages).

Reuter et al., “Selective Non-Steroidal Glucocorticoid Receptor Agonists Attenuate Inflarrmation but Do Not Impair Intestinal Epithelial Cell,” Restitution In Vitro, PLOS One, vol. 7, No. 1, Jan. 25, 2012.

Reuter et al., “M1682 Compound a (CpdA), a Selective Glucocorticoid Receptor Agonist (SEGRA), Positively Affects Wound Healing While Reducing NF-KappaB Activity in Intestinal Epithelial Cells,” Gastroenterology: Official Publication of the American Gastroenterological Association, Williams & Wilkins, US, vol. 134, No. 4, p. A-396, Apr. 1, 2008.

Schacke et al., “Characterization of ZK 245186, a novel, selective glucocorticoid receptor agonist for the topical treatment of inflammatory skin diseases,” British Journal of Pharmacology, John Wiley & Sons Ltd, GB, vol. 158, No. 4, Oct. 1, 2009, pp. 1088-1103.

Anderson et al., “Factors That Impair Wound Healing,” Journal of the American College of Clinical Wound Specialists, 2014, vol. 4, No. 4, pp. 84-91.

Badarau et al., “Discovery of a subnanomolar and selective spirocyclic agonist of the glucocorticoid receptor,” European Journal of Medicinal Chemistry, Jan. 1, 2019, vol. 161, pp. 354-363.

Dissemond et al., “Modern wound care—practical aspects of non-interventional topical treatment of patients with chronic wounds,” JDDG: Journal der Deutschen Dermatologischen Gesellschaft, 2014, vol. 12, vol. 7, pp. 541-554.

Hengge et al., “Adverse effects of topical glucocorticosteroids,” Journal of the American Academy of Dermatology, Jan. 2006, vol. 54, No. 1, pp. 1-15.

Schacke et al., “Dissociation of transactivation from transrepression by a selective glucocorticoid receptor agonist leads to separation of therapeutic effects from side effects,” Proceedings of the National Academy of Sciences of the United States of America, Jan. 6, 2004, vol. 101, No. 1, pp. 227-232.

Wicke et al., “Effects of Steroids and Retinoids on Wound Healing,” Archives of Surgery, Nov. 2000, vol. 135, No. 11, pp. 1265-1270.

STN Registry No. 2089130-74-3 (Apr. 7, 2017); STN Registry No. 1807867-82-8 (Sep. 22, 2015); STN Registry No. 1245526-82-2 (Oct. 5, 2010); STN Registry No. 1198784-72-3 (Dec. 28, 2009); STN Registry No. 1196509-69-2-2 (Dec. 8, 2009); STN Registry No. 887375-26-0 (Jun. 11, 2006); STN Registry No. 143-28-2 (Nov. 16, 1984); (4 pages).

Cavet et al., “Anti-allergic effects of mapracorat, a novel selective glucocorticoid receptor agonist, in human conjunctival fibroblasts and epithelial cells.,” Molecular Vision, Jul. 19, 2013, pp. 1515-1525 (11 pages).

Anderson et al., “Factors That Impair Wound Healing,” Journal of the American College of Clinical Wound Specialists (2014) 4, pp. 84-91.

Dinh, et al., “Mechanisms Involved in the Development and Healing of Diabetic Foot Ulceration” Diabetes 61., Nov. 2012, pp. 2937-2947.

Durmus, et al. “The Effects of Single-Dose Dexamethasone on Wound Healing in Rats,” Anesth. Analg., 97, 2003, pp. 1377-1380.

Löwenberg, et al., “Novel insights into mechanisms of glucocorticoid action and the development of new glucocorticoid receptor ligands,” Steroids 73, Dec. 14, 2007, pp. 1025-1029.

Stahn, et al., “Molecular mechanisms of glucocorticoid action and selective glucocorticoid receptor agonists,” Molecular and Cellular Endocrinology 275, (2007) pp. 71-78.

* cited by examiner

A) Pig wounds with R848 + WE-01

B) Pig wounds with R848 + WE-02

C) Pig wounds with R848 + human serum

D) Pig wounds with human serum

Figure 15

| | WE | Mapracorat |
|---|---|---|
| WE-04 | 100 | 745 |
| WE-05 | 100 | 431 |
| WE-06 | 100 | 317 |
| WE-07 | 100 | 307 |
| WE-08 | 100 | 296 |
| WE-09 | 100 | 294 |
| WE-10 | 100 | 289 |
| WE-11 | 100 | 269 |
| WE-12 | 100 | 265 |
| WE-13 | 100 | 260 |
| WE-14 | 100 | 256 |
| WE-15 | 100 | 255 |
| WE-16 | 100 | 249 |
| WE-17 | 100 | 246 |
| WE-18 | 100 | 241 |
| WE-19 | 100 | 240 |
| WE-20 | 100 | 239 |
| WE-21 | 100 | 235 |
| WE-22 | 100 | 231 |
| WE-23 | 100 | 230 |
| WE-24 | 100 | 227 |
| WE-25 | 100 | 224 |
| WE-03 | 100 | 220 |
| WE-26 | 100 | 217 |
| WE-27 | 100 | 216 |
| WE-28 | 100 | 209 |
| WE-29 | 100 | 208 |
| WE-02 | 100 | 207 |
| WE-30 | 100 | 205 |
| WE-31 | 100 | 201 |
| WE-32 | 100 | 197 |
| WE-33 | 100 | 195 |
| WE-34 | 100 | 194 |
| WE-35 | 100 | 189 |
| WE-01 | 100 | 189 |
| WE-36 | 100 | 187 |
| WE-37 | 100 | 183 |
| WE-38 | 100 | 183 |

| | WE | Mapracorat |
|---|---|---|
| WE-39 | 100 | 182 |
| WE-40 | 100 | 182 |
| WE-41 | 100 | 182 |
| WE-42 | 100 | 179 |
| WE-43 | 100 | 178 |
| WE-44 | 100 | 173 |
| WE-45 | 100 | 173 |
| WE-46 | 100 | 166 |
| WE-47 | 100 | 166 |
| WE-48 | 100 | 165 |
| WE-49 | 100 | 159 |
| WE-50 | 100 | 158 |
| WE-51 | 100 | 151 |
| WE-52 | 100 | 150 |
| WE-53 | 100 | 150 |
| WE-54 | 100 | 148 |
| WE-55 | 100 | 147 |
| WE-56 | 100 | 146 |
| WE-57 | 100 | 146 |
| WE-58 | 100 | 142 |
| WE-59 | 100 | 141 |
| WE-60 | 100 | 140 |
| WE-61 | 100 | 138 |
| WE-62 | 100 | 136 |
| WE-63 | 100 | 135 |
| WE-64 | 100 | 134 |
| WE-65 | 100 | 132 |
| WE-66 | 100 | 132 |
| WE-67 | 100 | 131 |
| WE-68 | 100 | 130 |
| WE-69 | 100 | 128 |
| WE-70 | 100 | 127 |
| WE-71 | 100 | 127 |
| WE-72 | 100 | 125 |
| WE-73 | 100 | 125 |
| WE-74 | 100 | 124 |
| WE-75 | 100 | 123 |
| WE-76 | 100 | 122 |

A)

B)

SELECTIVE GLUCOCORTICOID RECEPTOR MODIFIERS FOR TREATING IMPAIRED SKIN WOUND HEALING

CROSS-REFERENCE TO RELATED APPLICATIONS

This application is a continuation of International PCT Application No. PCT/EP2020/051457, filed Jan. 22, 2020, designating the United States and published in English, which claims priority to and the benefit of European Patent Application No. 19153026.0, filed Jan. 22, 2019, and European Patent Application No. 19170117.6, filed Apr. 18, 2019, the contents of all of which are hereby incorporated by reference in their entireties.

SEQUENCE LISTING

The present application contains a Sequence Listing which has been submitted electronically in ASCII format and is hereby incorporated by reference in its entirety. Said ASCII copy, created on Aug. 15, 2023, is named 190546-010403US-SL.txt and is 1,145 bytes in size.

The present invention relates to a Selective Glucocorticoid Receptor Modulator (SEGRM), or a pharmaceutically acceptable salt thereof, for use in the treatment of impaired skin wound healing in a subject, an in vitro method for identifying a subject suffering from impaired skin wound healing to be responsive to the treatment with a Selective Glucocorticoid Receptor Modulator (SEGRM), or a pharmaceutically acceptable salt thereof, and kits and kits-of-part related thereto.

Chronic wounds are a major health issue worldwide with 6.5 million affected patients in the US alone and an expected increase due to the aging population and growing incidence of metabolic diseases [Sen C K et al (2009) Wound Repair Regen 17: 763-771; Gould L et al (2015) Wound Repair Regen 23:1-13].

Chronic wounds have a multifactorial etiology and are dependent on different variables: a) underlying disease, e.g. diabetes, arterial or venous insufficiency, b) pressure, c) age and nutritional status and d) microbial environment [Gould L et al (2015) Wound Repair Regen 23:1-13].

Chronic wounds are generally understood as those wounds that have not healed within 2 months. They are a major health issue worldwide. In developed countries, including the US and the EU, it has been estimated that 1 to 2% of the total population will experience a chronic wound during their lifetime [Gottrup F (2004) Am J Surg 187:38S-43S].

The major chronic wound indications are venous ulcers, pressure ulcers and diabetic foot ulcers. Venous ulcers are defects in pathologically altered tissue on the lower leg based on chronic venous insufficiency, often accompanied by deep venous thrombosis. Pressure ulcers are the results of severe tissue hypoxemia in immobilized patients. Diabetic foot ulceration can affect up to 25% of patients with diabetes throughout their lifetime and often results in lower limb amputation. The standard of care for all of these wounds, as recommended by the German Society for Dermatology [Dissemond J et al (2014) JDDG 1610-0379/2014/1207: 541-554] includes wound dressings, surgical and biological (maggot) debridement, infection control and negative pressure therapy. Regranex® (PDGF: platelet-derived growth factor) was the only registered pharmacological treatment for a long time, but its therapeutic efficacy is minor, as is the success of cell-based therapies. Recombinant human EGF (rhEGF) is registered as Heberprot-P® in several countries for treating ulcerations in the diabetic foot ulcus syndrome. Moreover, Trafermin (brand name: Fiblast®), also known as recombinant human basic fibroblast growth factor (rhbFGF), is a recombinant form of human basic fibroblast growth factor (bFGF) which is marketed in Japan as a topical spray for the treatment of skin ulcers.

Recurrence is a problem in one third of all chronic wounds, regardless of their treatment.

Even though they are anti-inflammatory in other settings, topical glucocorticoids cannot be used because one of their side effects is actually delayed wound healing [Hengge U R (2006) J Am Acad Dermatol 54:1-15]. Therefore, as a dogma in the prior art, topical glucocorticoids are described to impair wound healing [Wicke C et al (2000) Arch Surg 135:1265-1270; Anderson K et al (2014) J Am Coll Clin Wound Spec 4:84-91]. Further, non-steroidal anti-inflammatory drugs, e.g. ibuprofen, are only effective in ameliorating wound pain [Dissemond J et al (2014), supra].

There is therefore an ongoing and strong medical need for reliable and effective therapies for the treatment of impaired skin wound healing in patients.

It was surprisingly found in the present application, as shown in the examples and corresponding Figures, that Selective Glucocorticoid Receptor Modulators (SEGRMs) exhibit an outstanding fibroblast proliferation (2D) enhancing and fibroblast derived matrix formation (3D) enhancing effect, increase Collagen-1 and -3 expression and inhibit IL-1beta secretion in a human-linked ex vivo wound healing model using wound exudates from chronic wound patients. For example, the effect of mapracorat, as exemplary SEGRM, was studied on fibroblast proliferation in the presence of >80 human wound exudates, leading to increases of >120%.

Figure 13:
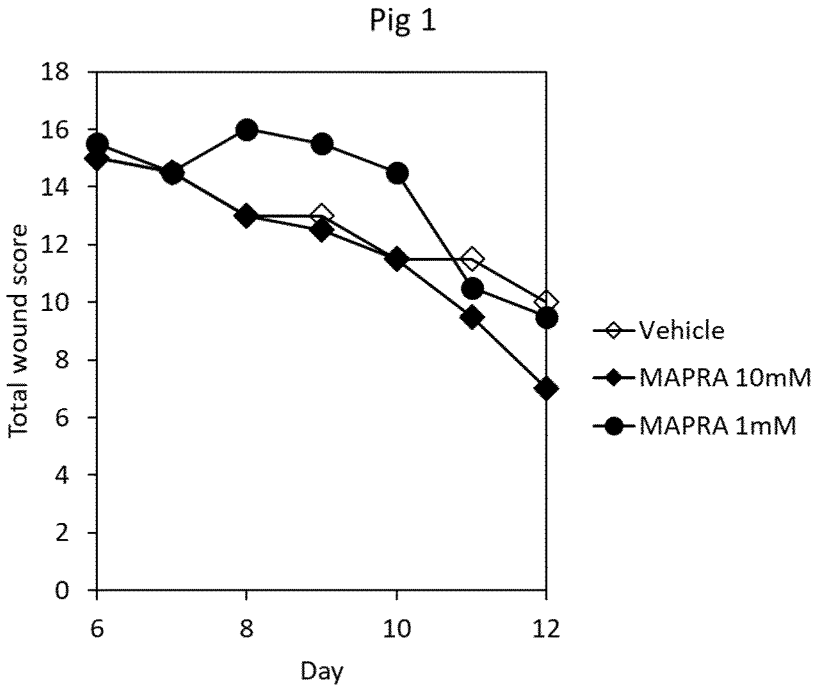
Figure 13:
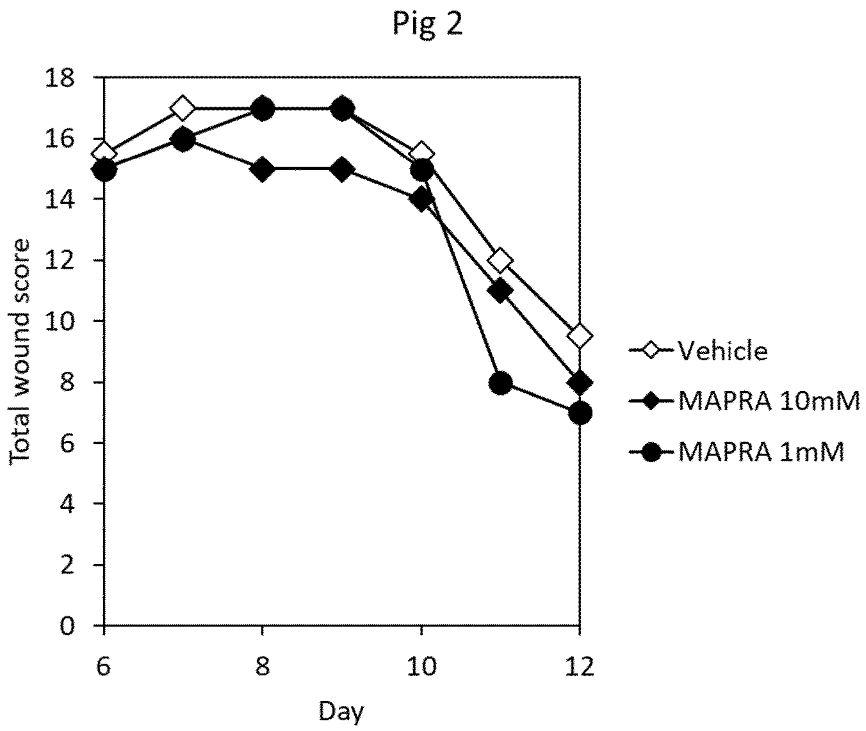
Figure 13:
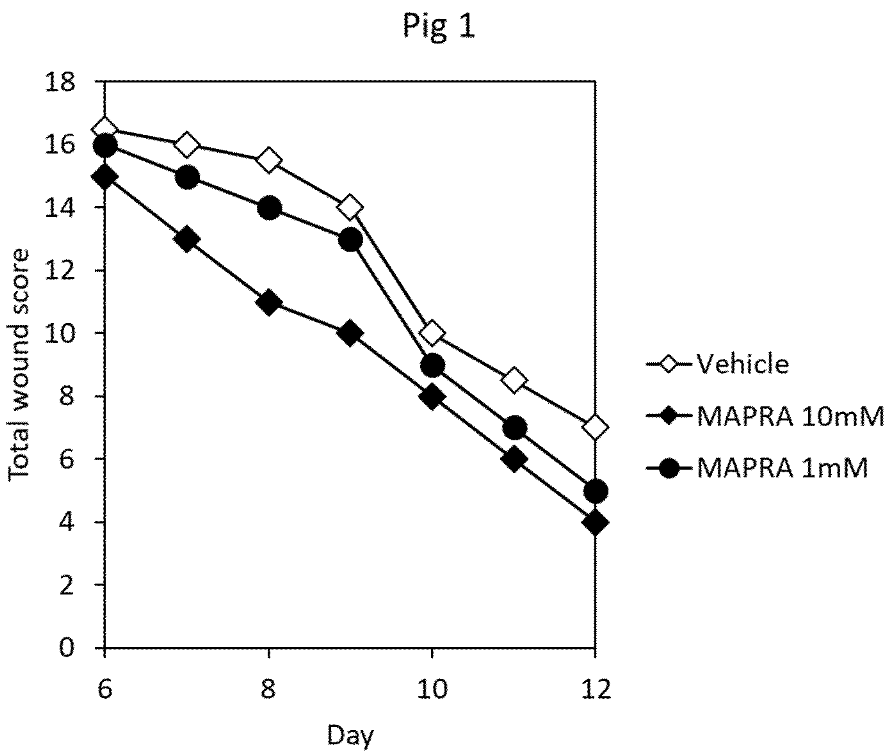
Figure 13:
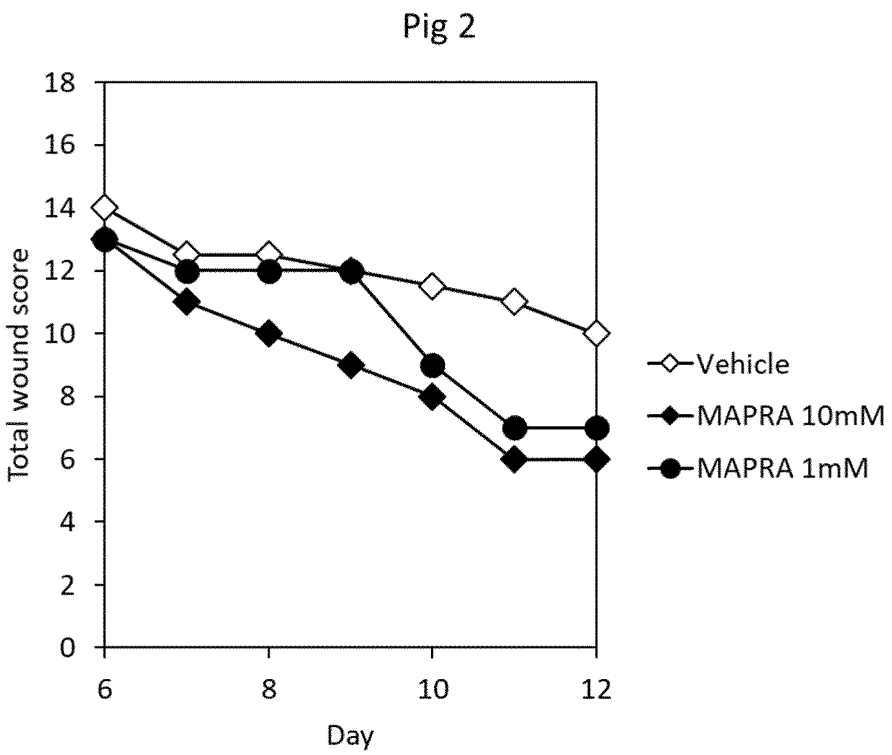
Figure 13:
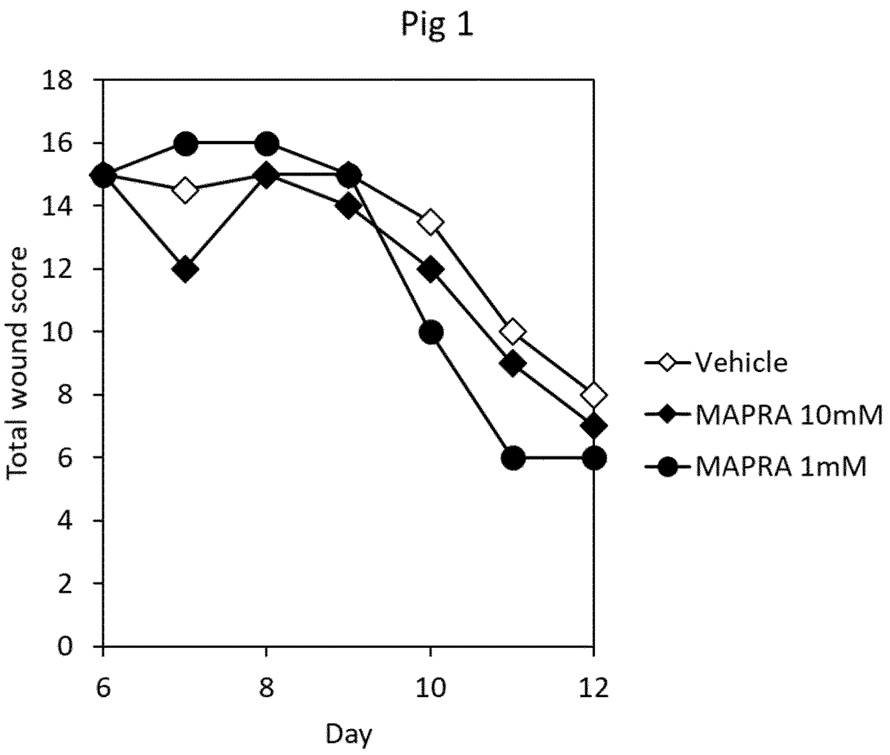
Figure 13:
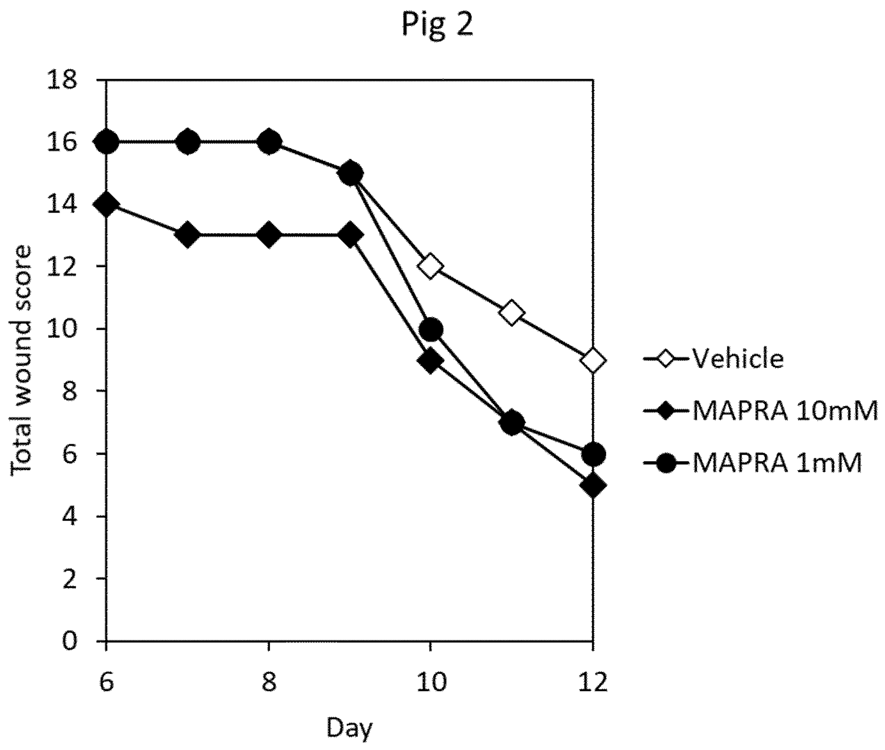
Figure 13:
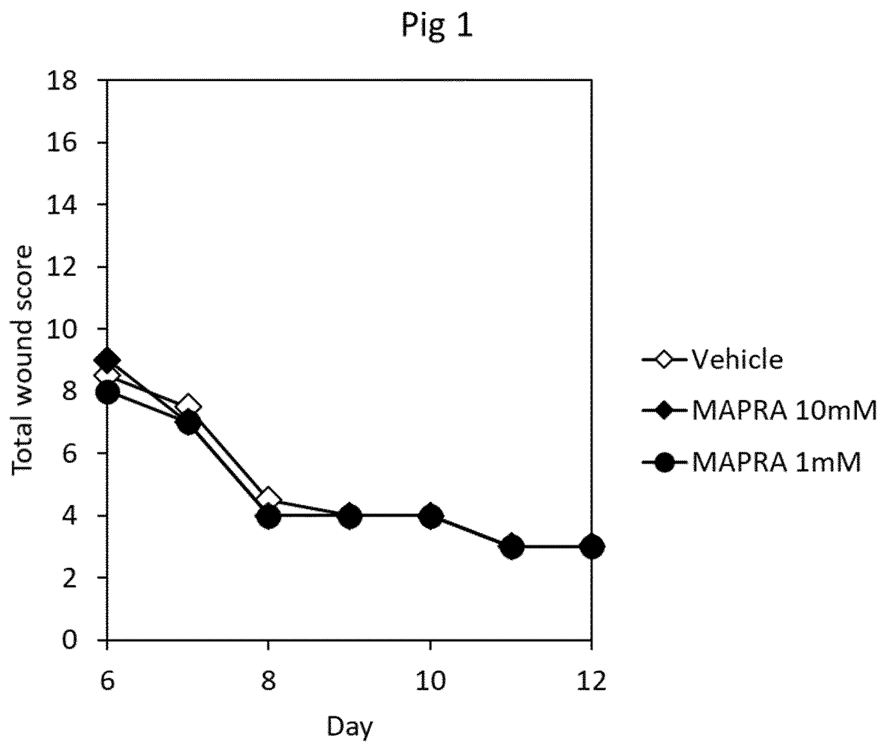
Figure 13:
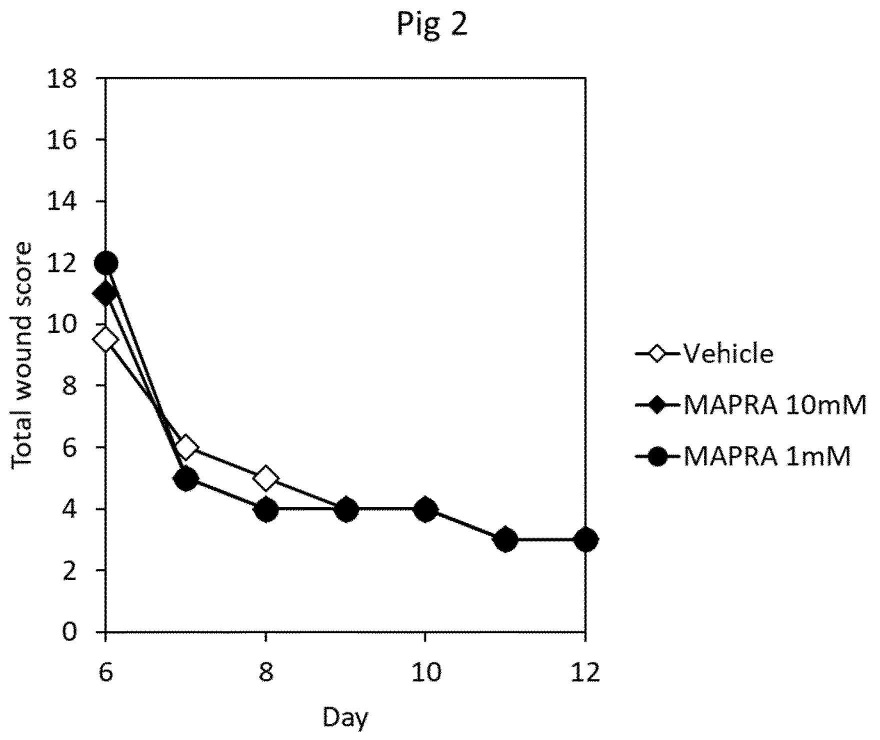

Moreover, it was found that mapracorat reduced the wound score from days 6 to 12 in wounds treated with wound exudates from chronic human wounds and/or the TLR 7/8 agonist R848 (resiquimod) as inducers of delayed wound healing in a pig model of delayed wound healing (FIG. 13).

Figure 2:
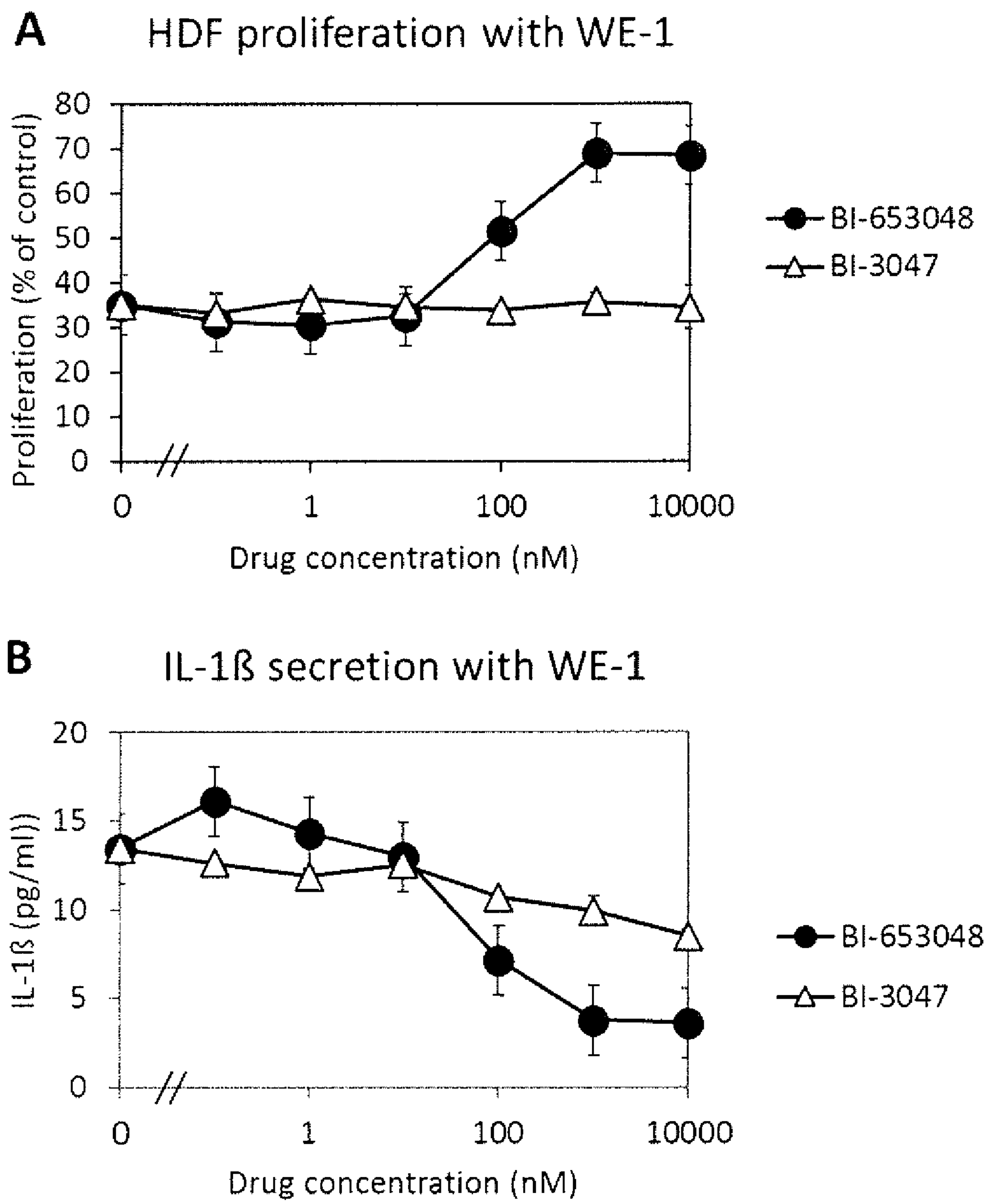

In addition, it was found in the examples that BI-653048, but not its inactive analogue BI-3047, dose-dependently enhanced fibroblast proliferation in the presence of different aggressive wound exudates (FIG. 1) and inhibited IL-1β secretion in these cultures (FIG. 2). The chemically different SEGRMs mapracorat, ZK216348 and HY14234 had similar effects on proliferation and IL-1β secretion or mRNA expression in the presence of wound exudates (FIGS. 5, 8, and 9-11). While qualitatively similar, the magnitude of effects differed depending on the SEGRM compound and the individual wound exudate. Therefore, in a preferred embodiment a personalized medicine approach with in vitro pretesting of patient exudates against different compounds can be performed by using methods of the invention described herein. Expression of collagen 1 and collagen 3 mRNAs in the fibroblast proliferation assay with wound exudate, but not medium, was increased by BI-653048 and mapracorat (FIGS. 3 and 6-8). The effect was reversed by the glucocorticoid receptor antagonist mifepristone (FIG. 4).

Figure 12:
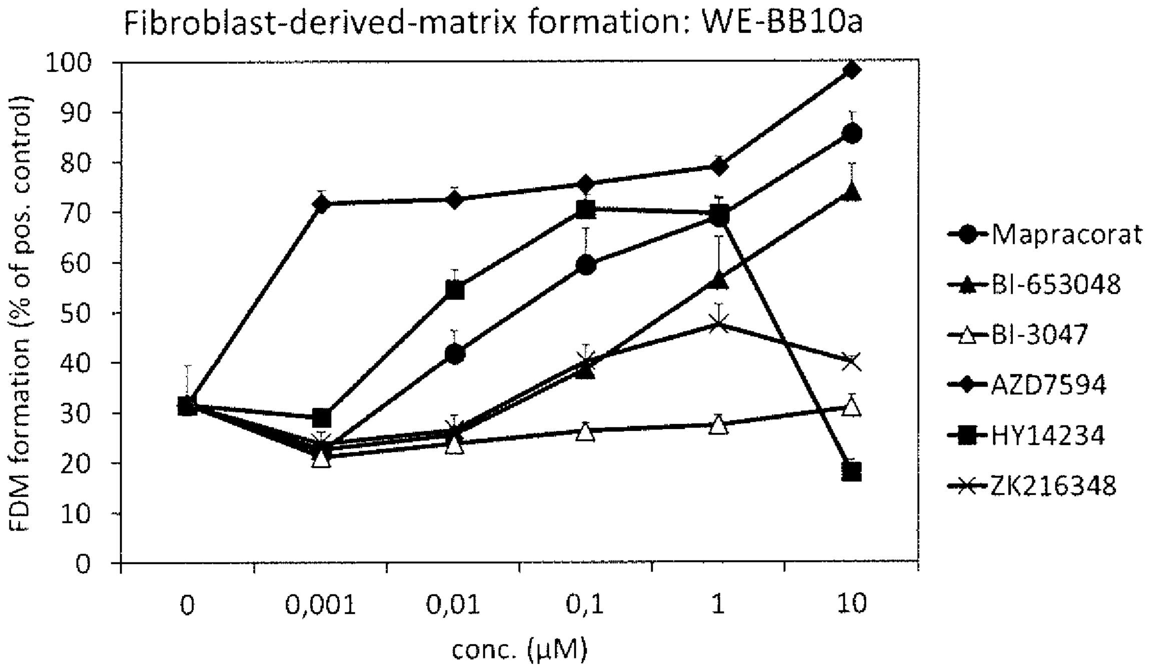

Further, a positive effect was observed in 3D fibroblast culture with wound exudate from a patient with a chronic, non-healing wound with a plurality of structurally different SEGRMs, including BI-653048 (but not its inactive analogue BI-3047), mapracorat, ZK216348, AZD7594, and HY14234 (FIG. 12). The fibroblast proliferation assay (2D) as well as the fibroblast derived matrix formation assay (3D) are human-linked ex vivo assays for wound healing.

Therefore, in one embodiment, the present invention relates to a Selective Glucocorticoid Receptor Modulator (SEGRM), or a pharmaceutically acceptable salt thereof, for use in the treatment of impaired skin wound healing in a subject.

The human glucocorticoid receptor, also designated "GR", "GC" or "GCR", is also known as NR3C1 (nuclear receptor subfamily 3, group C, member 1) and is the receptor to which cortisol and other glucocorticoids bind. In a preferred embodiment, the glucocorticoid receptor is human glucocorticoid receptor.

The GR is expressed in almost every cell in the body and regulates genes controlling the development, metabolism, and immune response. Because the receptor gene is expressed in several forms, it has many different (pleiotropic) effects in different parts of the body.

When the GR binds to glucocorticoids, its primary mechanism of action is the regulation of gene transcription. The unbound receptor resides in the cytosol of the cell. After the receptor is bound to glucocorticoid, the receptor-glucocorticoid complex can take different paths. The activated GR complex up-regulates the expression of anti-inflammatory proteins in the nucleus or represses the expression of pro-inflammatory proteins in the cytosol (by preventing the translocation of other transcription factors from the cytosol into the nucleus). Alternatively, repression can be achieved by binding of the receptor to DNA in the same site where another transcription factor would bind, thus abrogating the effect of the other transcription factor.

In humans, the GR protein is encoded by NR3C1 gene which is located on chromosome 5 (5q31). Various alternatively spliced isoforms exist.

"Selective Glucocorticoid Receptor Modulators" or "SEGRMs" are a well-known and established compound class. Selective Glucocorticoid Receptor Modulators are preferably non-steroidal Selective Glucocorticoid Receptor Modulator (SEGRM). In older prior art documents, Selective Glucocorticoid Receptor Modulators are also designated as "selective glucocorticoid receptor agonists" or "SEGRAs" or as "dissociated glucocorticoid receptor agonists" or "DIGRAs". Further, in another preferred embodiment, SEGRMS are also designated in some prior art documents as "SGRM", "GR agonists" or "SEDIGRAMs". Accordingly, in a preferred embodiment, "Selective Glucocorticoid Receptor Activators" or "SEGRAs" are a well-known and established compound class. Selective Glucocorticoid Receptor Activators are preferably non-steroidal Selective Glucocorticoid Receptor Activators (SEGRA). In another preferred embodiment, it is also referred to SEGRM or SEGRA in the prior art as "Selective Glucocorticoid Receptor Activators and Modulators" or "SEGRAMs". Accordingly, in a preferred embodiment, the terms "SEGRM" and "SEGRA" are synonyms. Preferably, the synonymous meaning is reflected in some prior art by the term "SEGRAMs".

Glucocorticoids are known to exhibit anti-inflammatory properties. However, as mentioned above, glucocorticoids also exhibit severe side effects, e.g., among several others, skin atrophy. As mentioned above, topical glucocorticoids cannot be used for e.g. diabetic ulcers and other common types of skin wounds with delayed wound healing, because one of their side effects is actually delayed wound healing.

SEGRMs achieve their selectivity by triggering only a subset of the glucocorticoid receptor mechanisms of action. In particular, SEGRM specifically bind to a glucocorticoid receptor (GC), but trigger only a subset the GC mechanisms of action.

Both non-selective glucocorticoids and SEGRMs exhibit their effect by binding to and activating the glucocorticoid receptor (GR). In contrast to glucocorticoids, which activate the GR to work through at least two signal transduction pathways commonly designated as "transactivation" and "transrepression", SEGRMs activate the GR in such a way that they only or mainly operate through one of these two main possible pathways, preferably by transrepression.

In the absence of glucocorticoids, the GR resides in the cytosol in an inactive state complexed with heat shock proteins (HSPs) and immunophilins. Binding of glucocorticoids to the GR activates the receptor by causing a conformational change in the GR and thus a dissociation of the bound HSPs. The activated GR can then regulate gene expression via one of two pathways "transactivation" and "transrepression":

Transactivation: The direct pathway is designated transactivation, whereby the activated GR dimerizes, is translocated into the nucleus and binds to specific sequences of DNA called glucocorticoid response elements (GREs). The GR/DNA complex recruits other proteins which transcribe downstream DNA into mRNA and eventually protein. Examples of glucocorticoid-responsive genes include those that encode tyrosine aminotransferase (TAT), annexin A1, T22D3, angiotensin-converting enzyme, neutral endopeptidase, dual specificity phosphatase 1, interferon regulatory factor 1 and other anti-inflammatory proteins.

Transrepression: The second, indirect pathway is called transrepression, in which activated monomeric GR binds to other transcription factors such as NF-κB and AP-1 and prevents these from up-regulating the expression of their target genes. These target genes encode proteins such as cyclooxygenase, NO synthase, phospholipase A2, tumor necrosis factor, transforming growth factor beta, ICAM-1, and a number of other pro-inflammatory proteins.

Hence the anti-inflammatory effects of glucocorticoids result from both transactivation and transrepression.

Accordingly, a SEGRM is a compound that more strongly transrepresses than transactivates.

Assays for determining transrepression are known in the art and include determining LPS-induced secretion of cytokines IL-12 or TNFalpha from PBMC cells, as e.g. described in detail in Schäcke et al. (2004; PNAS, 101: 227-232) or inhibition of collagenase promoter activity, inhibition of cytokine secretion, such as IL-12 or IFNgamma, in stimulated human primary cells, or inhibition of lymphocyte proliferation in mixed lymphocyte reaction, as all described in detail in Schäcke et al. (2009; Br. J. Pharmacol., 158: 1088-1103).

Assays for determining transactivation are known in the art and include determining the induction of tyrosine aminotransferase (TAT) activity in hepatocytes, as e.g. described in detail Schäcke et al. (2004; PNAS, 101: 227-232) or the induction of MMTV promoter activity or induction of TAT activity, as described in detail in Schäcke et al. (2009; Br. J. Pharmacol., 158: 1088-1103).

Preferably, the assays for determining transactivation and transrepression may be performed as follows as described in Schäcke et al (2009):

Preferably, inhibition of collagenase promoter activity may be determined as follows as described in Schäcke et al (2009): HeLa cells stably transfected with a luciferase reporter gene linked to the collagenase promoter are cultured for 24 h in Dulbecco's modified Eagle's medium supplemented with 3% charcoal absorbed foetal calf serum (FCS), 50 units$\cdot$mL$^{-1}$ penicillin and 50 mg$\cdot$mL$^{-1}$ streptomycin, 4 mmol$\cdot$L$^{-1}$ L-glutamine and 300 μg$\cdot$mL$^{-1}$ geneticin. Cells are then seeded onto 96-well dishes ($1\times10^4$ cells per well). After 24 h, cells are incubated with inflammatory stimulus [10 $ng\cdot mL^{-1}$ 12-o-tetradecanoylphorbol 13-acetate (TPA)] with or without increasing concentrations (1 $pmol\cdot L^{-1}$ to 1 $mmol\cdot L^{-1}$) of reference or test compounds. As negative control (unstimulated cells) cells are incubated with 0.1% dimethylsulphoxide (DMSO) and as positive control cells (stimulated cells) are incubated with 10 $mg\cdot mL^{-1}$ TPA plus 0.1% DMSO. After 18 h luciferase assay is carried out.

Preferably, inhibition of secretion of cytokines IFN-γ and IL-12p40 in stimulated human primary cells may be determined as follows as described in Schäcke et al (2009): Effects of compounds on monocytic secretion of IL-12p40 is determined after stimulation of peripheral blood mononuclear cells (PBMCs) from healthy donors with 10 $ng\cdot mL^{-1}$ lipopolysaccharide (*Escherichia coli* serotype 0127:B8; Sigma). Effects on interferon (IFN)-γ secretion are determined after PBMC stimulation with 10 $\mu g\cdot mL^{-1}$ of the mitogenic lectin, phytohemagglutinin. After 24 h incubation (37° C., 5% $CO_2$), cytokine concentrations in supernatants of treated cells are determined using specific ELISA kits: IFN-γ and IL-12p40 ELISA (R&D Systems).

Preferably, induction of MMTV promoter activity may be determined as follows as described in Schäcke et al (2009): The MMTV promoter is linked to a luciferase reporter gene and HeLa cells are stably transfected with this construct. Cells are grown in Dulbecco's modified Eagle's medium supplemented with 50 units of penicillin and 300 $\mu g\cdot mL^{-1}$ geneticin. To study transactivation activity of GR ligands, cells are cultured for 24 h in medium supplemented with 3% charcoal absorbed FCS. Cells are then seeded onto 96-well plates with $1\times10^4$ cells per well. After 24 h, cells are incubated with increasing concentrations of reference (dexamethasone) or test compounds. As negative control (unstimulated cells) cells are treated with 0.1% DMSO. Cells are incubated for 18 h with compounds, and then luciferase activity as a measure of GR activity is determined.

Preferably, induction of TAT activity may be determined as follows as described in Schäcke et al (2009): Induction of TAT by test compounds is determined in vitro using the human hepatoma cell line, HepG2. HepG2 cells are cultured in minimum essential medium containing 2 $mmol\cdot L^{-1}$ glutamax, 10% heat-inactivated FCS and 1% non-essential amino acids. To test induction of TAT by test compounds cells are seeded onto 96-well plates with $1\times10^5$ cells per well. After 24 h cells are incubated with test medium containing increasing concentrations of test and reference compounds. After 24 h cells are lysed and TAT activity is measured as absorption of the aromatic p-hydroxybenzaldehyde at 340 nm upon conversion of p-hydroxyphenylpyruvate.

Therefore, in yet a further preferred embodiment of the present invention, the Selective Glucocorticoid Receptor Modulator (SEGRM), or pharmaceutically acceptable salt thereof, is a non-steroidal Selective Glucocorticoid Receptor Modulator (SEGRM). A Selective Glucocorticoid Receptor Modulator binds to a Glucocorticoid Receptor (GC). In a more preferred embodiment, SEGRMs achieve their selectivity by triggering only a subset of the mechanisms of action with an affinity (KD) less than 100 nM, 70 nM, 60 nM, 50 nM, 40 nM, 30 nM, 20 nM or 10 nM. Affinity (KD) can be determined by methods known in the art, for example, by using surface plasmon resonance (SPR) measurement, e.g. using a Biacore device. Preferably, affinity is determined at about 20° C. or 25° C.

In yet a further preferred embodiment of the present invention, the non-steroidal Selective Glucocorticoid Receptor Modulator (SEGRM) triggers transrepression upon binding to a Glucocorticoid Receptor (GC) in a cell and exhibits less transactivation upon binding to a Glucocorticoid Receptor (GC) in a cell as compared to Dexamethasone.

In one preferred embodiment, the $IC_{50}$ value for transrepression activity of a SEGRM for use of the invention is at most 100-fold, 50-fold, 30-fold, at most 10 fold, at most 5-fold or at most 2-fold higher than the $IC_{50}$ value for transrepression activity of dexamethasone. In one more preferred embodiment, the $IC_{50}$ value for transrepression activity of a SEGRM is similar to the $IC_{50}$ value for transrepression activity of dexamethasone, as e.g. found for mapracorat. For example, the $IC_{50}$ value for transrepression activity of dexamethasone may also be lower, such as 2-fold or 5-fold lower, than the $IC_{50}$ value for transrepression activity of dexamethasone. The values are preferably determined in one of the transrepression assays described above.

In one preferred embodiment, the efficacy of transrepression activity of a SEGRM for use of the invention is at least 30%, 40%, 50%, 60%, 70%, 80% or 90% of the efficacy of transrepression activity of dexamethasone. The values are preferably determined in one of the transrepression assays described above.

In one preferred embodiment, the $EC_{50}$ value for transactivation activity of a SEGRM for use of the invention is at least 20-fold, 40-fold, 50-fold or 100-fold higher than the $EC_{50}$ value for transactivation activity of dexamethasone. The values are preferably determined in one of the transactivation assays described above.

As explained above, SEGRMs exhibit their effect by binding to and activating the glucocorticoid receptor (GR).

Accordingly, in a preferred embodiment, a SEGRM for use according to the present invention is an activator of the glucocorticoid receptor (GR).

Accordingly, in a preferred embodiment, a SEGRM for use according to the present invention is a glucocorticoid receptor (GR) agonist.

Preferably, an activator of the glucocorticoid receptor (GR), or a glucocorticoid receptor (GR) agonist, is understood as a compound which activates the GR through transactivation and/or transrepression of the GR. Transactivation and transrepression can be determined using the assays above.

As explained above, a SEGRM for use according to the invention is a compound that more strongly transrepresses than transactivates. Accordingly, in a preferred embodiment, a SEGRM for use according to the invention activates the GR through transrepression and optionally transactivation of the GR. In a more preferred embodiment, a SEGRM for use according to the invention activates the GR through transrepression and transactivation of the GR, wherein the SEGRM strongly transrepresses than transactivates. Assays for determining transactivation and transrepression and for determining whether the SEGRM more strongly transrepresses than transactivates are described above.

Preferably, a SEGRM that is an activator of the glucocorticoid receptor (GR), or a glucocorticoid receptor (GR) agonist, can be positively tested in an in vitro translocation assay as described in Example 1.10. The assay represents an additional positive assay for a SEGRM that is an activator of the glucocorticoid receptor (GR), or a glucocorticoid receptor (GR) agonist. In particular, the assay does not allow to distinguish between an active Glucocorticoid and an active SEGRM, as also glucocorticoids effect translocation of the glucocorticoid receptor from the cytoplasm into the nucleus in primary human fibroblasts in an in vitro culture at a concentration of 10 nM at 37° C. for the assay in Example 1.10.

Accordingly, in a preferred embodiment, a SEGRM that is an activator of the glucocorticoid receptor (GR), or a glucocorticoid receptor (GR) agonist, for use of the invention, effects translocation of the glucocorticoid receptor from the cytoplasm into the nucleus in primary human fibroblasts in an in vitro culture at a concentration of the SEGRM of 10 nM or 100 nM at 37° C. The assay is described in detail in Example 1.10. In particular, the cultured cells are starved overnight, incubated with compound for 45 minutes at 37° C. and fixed with 4% paraformaldehyde for 10 minutes at room temperature, followed by permeabilization with 0.5% Triton X100 in PBS in 1% BSA, for 10 minutes at room temperature. Subsequently, the cells are stained with a mouse-anti-glucocorticoid receptor monoclonal antibody. Detection may be performed by immunofluorescence microscopy using a secondary antibody labeled with a fluorescent label.

In yet a further preferred embodiment of the present invention, the non-steroidal Selective Glucocorticoid Receptor Modulator (SEGRM) specifically binds to a Glucocorticoid Receptor (GC) with an affinity (KD) less than 100 nM.

In yet a further preferred embodiment of the present invention, the non-steroidal Selective Glucocorticoid Receptor Modulator (SEGRM) specifically binds to a Glucocorticoid Receptor (GC). A SEGRM is understood to specifically bind to a Glucocorticoid Receptor (GC) in case the competition factor for a SEGRM, defined as $IC_{50}$ of SEGRM test compound/$IC_{50}$ of reference compound, for Glucocorticoid Receptor (GC) is lower than 20, 10, 5, 4 or 2 and the competition factor for progesterone receptor (PR), androgen receptor (AR) and mineralocorticoid receptor (MR) is at least 5, 10, 15, 20, 30, 40 or 50. The competition factor can be determined as described in Schäcke et al. (2009; Br. J. Pharmacol., 158: 1088-1103). As described in Schäcke et al., a suitable reference compound for GC is dexamethasone, a suitable reference compound for PR is progesterone, a suitable reference compound for AR is metribolone, and a suitable reference compound for MR is aldosterone.

Preferably, the competition factor may be determined as follows as described in Schäcke et al (2009):

The IC50 values for determining receptor binding may be determined as follows as described in Schäcke et al (2009): extracts from Sf9 cells, infected with recombinant baculovirus coding for the human GR, progesterone receptor (PR), androgen receptor (AR) or mineralocorticoid receptor (MR) are used for the receptor binding assays, as already described in Schäcke et al. (2004). All receptor nomenclature follows the 'Guide to receptors and channels' (Alexander et al., 2008). For the binding assays for GR, PR, AR and MR [1,2,4,6,7-3H]dexamethasone (approximately 3.18 $GBq\cdot mmol^{-1}$)(~20 $nmol\cdot L^{-1}$), [1,2,6,7-3H(N)]progesterone (approximately 3.7 $GBq\cdot mmol^{-1}$), [17a-methyl 3H]methyltrienolone (approximately 3.18 $GBq\cdot mmol^{-1}$) or D[1,2,6,7-3H(N)]aldosterone (approximately 2.81 $GBq\cdot mmol^{-1}$) respectively, SF9 cytosol (100-500 μg protein), test compounds and binding buffer (10 $mmol\cdot L^{-1}$ Tris/HCL pH 7.4, 1.5 $mmol\cdot L^{-1}$ EDTA, 10% glycerol) are mixed in a total volume of 50 μL and incubated for 1 h at room temperature. After incubation, 50 μL of cold charcoal suspension is added for 5 min and the mixtures are transferred to microtiter filtration plates. The mixtures are filtered into Picoplates (Canberra Packard) and mixed with 200 μL Microszint-40 (Canberra Packard). The bound radioactivity is determined with a Packard Top Count plate reader. Specific binding is defined as the difference between binding of [1,2,4,6,7-3H] dexamethasone, [1,2,6,7-3H(N)]progesterone, [17a-methyl-3H]methyltrienolone and D[1,2,6,7-3H(N)]aldosterone in the absence and presence of 10 $\mu mol\cdot L^{-1}$ unlabelled dexamethasone, progesterone, metribolone or aldosterone respectively. The concentration of test compound giving 50% inhibition of specific binding (IC50) is determined from Hill analysis of the binding curves. The competition factor (CF) is defined as IC50 of test compound/IC50 of reference compound, and can be determined accordingly. By definition, CF is 1.0 for the reference compounds. The reference compound for GC is preferably dexamethasone, a suitable reference compound for PR is progesterone, a suitable reference compound for AR is metribolone, and a suitable reference compound for MR is aldosterone.

In one preferred embodiment, the Selective Glucocorticoid Receptor Modulator (SEGRM), or pharmaceutically acceptable salt thereof for use of the invention is a Selective Glucocorticoid Receptor Modulator (SEGRM) which is characterized as follows:

the SEGRM specifically binds to a Glucocorticoid Receptor (GC) with an affinity (KD) of less than 100 nM, and/or the competition factor for the SEGRM i) is lower than 20 for Glucocorticoid Receptor (GC), and ii) is at least 5 for progesterone receptor (PR), androgen receptor (AR) and mineralocorticoid receptor (MR), wherein the competition factor is defined as IC50 value of the SEGRM/IC50 of a reference compound, and wherein the reference compound for GC is dexamethasone, the reference compound for PR is progesterone, the reference compound for AR is metribolone, and the reference compound for MR is aldosterone, and/or the EC50 value for transactivation activity of the SEGRM upon binding to a Glucocorticoid Receptor (GC) in a cell is at least 20-fold higher than the EC50 value for transactivation activity of dexamethasone and/or the the IC50 value for transrepression activity of the SEGRM upon binding to a Glucocorticoid Receptor (GC) in a cell is at most 100-fold higher than the IC50 value for transrepression activity of dexamethasone.

Therefore, in one preferred embodiment, the Selective Glucocorticoid Receptor Modulator (SEGRM), or pharmaceutically acceptable salt thereof, for use of the invention is a non-steroidal Selective Glucocorticoid Receptor Modulator (SEGRM), and:

the SEGRM specifically binds to a Glucocorticoid Receptor (GC) with an affinity (KD) of less than 100 nM, and/or the competition factor for the SEGRM i) is lower than 20 for Glucocorticoid Receptor (GC), and ii) is at least 5 for progesterone receptor (PR), androgen receptor (AR) and mineralocorticoid receptor (MR), wherein the competition factor is defined as IC50 value of the SEGRM/IC50 of a reference compound, and wherein the reference compound for GC is dexamethasone, the reference compound for PR is progesterone, the reference compound for AR is metribolone, and the reference compound for MR is aldosterone, and/or the EC50 value for transactivation activity of the SEGRM upon binding to a Glucocorticoid Receptor (GC) in a cell is at least 20-fold higher than the EC50 value for transactivation activity of dexamethasone and/or the the IC50 value for transrepression activity of the SEGRM upon binding to a Glucocorticoid Receptor (GC) in a cell is at most 100-fold higher than the IC50 value for transrepression activity of dexamethasone.

In yet a further preferred embodiment, the Selective Glucocorticoid Receptor Modulator (SEGRM), or pharmaceutically acceptable salt thereof specifically binds to a Glucocorticoid Receptor (GC) with an affinity (KD) of less than 100 nM, and/or is a non-steroidal SEGRM.

Preferably, for a SEGRM that more strongly transrepresses than transactivates as defined above, activity of the SEGRM can, in addition, be positively tested in an in vitro assay as described in Example 1.10, 1.11 and/or 1.12. The assays represent additional positive assays for a SEGRM which does more strongly transrepress than transactivate and which assays may be used to differentiate between active and inactive stereoisomers of the same structure, such as BI-3047. In particular, the assays do not allow to distinguish between an active Glucocorticoid and an active SEGRM, as also glucocorticoids effect translocation of the glucocorticoid receptor from the cytoplasm into the nucleus in primary human fibroblasts in an in vitro culture at a concentration of 10 nM at 37° C. in case of the translocation assay in Example 1.10.

Accordingly, in a preferred embodiment, a SEGRM for use of the invention effects translocation of the glucocorticoid receptor from the cytoplasm into the nucleus in primary human fibroblasts in an in vitro culture at a concentration of the SEGRM of 10 nM or 100 nM at 37° C. The assay is described in detail in Example 1.10. In particular, the cultured cells are starved overnight, incubated with compound for 45 minutes at 37° C. and fixed with 4% paraformaldehyde for 10 minutes at room temperature, followed by permeabilization with 0.5% Triton X100 in PBS in 1% BSA, for 10 minutes at room temperature. Subsequently, the cells are stained with a mouse-anti-glucocorticoid receptor monoclonal antibody. Detection may be performed by immunofluorescence microscopy using a secondary antibody labeled with a fluorescent label.

Accordingly, in another preferred embodiment, a SEGRM for use of the invention reduces spontaneous IL-8 secretion from human monocytes in vitro at a concentration of 100 nM at 37° C. by at least 20%, 30% or 50% as compared to control cells incubated without SEGRM compound. The assay is described in detail in Example 1.11.

Accordingly, in yet another preferred embodiment, a SEGRM for use of the invention reduces IL-8 secretion from LPS-stimulated U937-cells in vitro at a concentration of 100 nM at 37° C. by at least 20%, 30% or 50% as compared to control cells incubated without SEGRM compound. The assay is described in detail in Example 1.12.

Suitable SEGRM for use in the invention are known in the art and include mapracorat (also known as ZK-245186) and related 5-substituted quinolone and isoquinoline derivative compounds, 5-{[(1S,2S)-1-(2-chloro-3-fluoro-4-methoxyphenyl)-3,3,3-trifluoro-2-hydroxy-2-(methoxymethyl)propyl]amino}-7-fluoro-1H-quinolin-2-one, 5-{(1S,2S)[1-(2-chloro-3-fluoro-4-methoxyphenyl)-3,3,3-trifluoro-2-hydroxy-2-(hydroxymethyl)propyl]amino}-7-fluoro-1H-quinolin-2-one, BI653048, HY14234, LGD-5552, MK-5932, Org 214007-0, Compound A, AL-438, ZK-216348, PF-802, Fosdagrocorat, and Compound 10. Further suitable SEGRM for use in the invention which are known in the art include [(3S)-1-[(3R)-5-oxotetrahydrofuran-3-carbonyl]-3-piperidyl]4-[(1R,2S)-1-(4-cyclopropylphenyl)-2-[[(2R)-tetrahydrofuran-2-carbonyl]amino]propoxy]benzoate, 5-{(1S,2R)[1-(2-chloro-3-fluoro-4-methoxyphenyl)-3,3,3-trifluoro-2-hydroxy-2-([methylsulfanyl]methyl)propyl]amino}-1H-chinoline-2-one, AZD-7594, AZD-5423, AZD-2906, JPT-117968, and SEGRM compounds disclosed in WO 2008/076048 A1, SEGRM disclosed in WO 2018/236749 A2, WO 2018/049255 A1 and WO 2018/183947 A1, BI-54903, BI-607812, GW870086X, PF-00251802, BOL-303242-X, which is a synonym for mapracorate, and further DIGRA compounds and formulations thereof disclosed in WO 2017/046096, WO 2009/023471 A2, WO 2008/027796 A2, WO 2008/033655 A2, WO 2008/005686 A2, WO 2008/021728 A2, WO 2008/021729 A2, WO 2008/154129 A1, WO 2009/042377 A1, WO 2010/123769 A1, WO 2012/170175 A1, the NO-donating DIGRA compounds disclosed in WO 2013/126156 A1, Cortivazol, Fluorocortivazol, spirocyclic analogues of fluorocortivazol disclosed in Badarau E. et al. (European Journal of Medicinal Chemistry, 2019, 161: 354-363), SEGRM compounds disclosed in WO 2003/086294 A2, WO 2004026248 A2, WO 2004/066920 A2, WO 2004/075840 A2, WO 2004/093805 A2, WO 2009/108525 A2, WO 2009/111214 A1, WO 2010/138421 A1, WO 2010/141247 A1, WO 2011/031574 A1, WO 2011/053567 A1, compounds disclosed in WO 2005/082909 A1, WO 2006/019716 A1, and WO 2009/103007 A2, WO 00/66522 A1, and RU24858.

Fosdagrocorat, also known as dagrocorat 2-(dihydrogen phosphate), has the following structure:

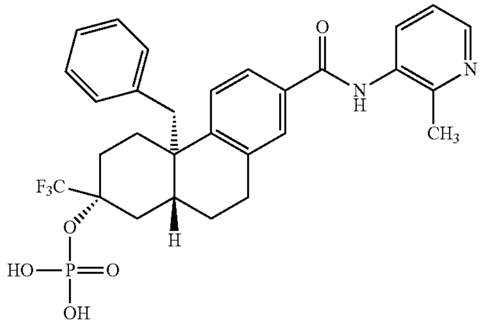

HY14234 has the following structure:

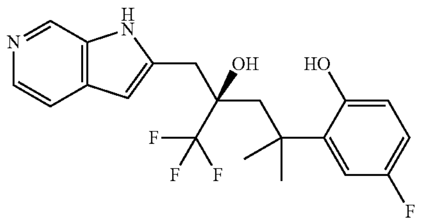 [SMILES: CC(C)(C[C@@](O)(Cc1cc2ccncc2[nH]1)C(F)(F)F)c1cc(F)ccc1O]

LGD-5552 has the following structure:

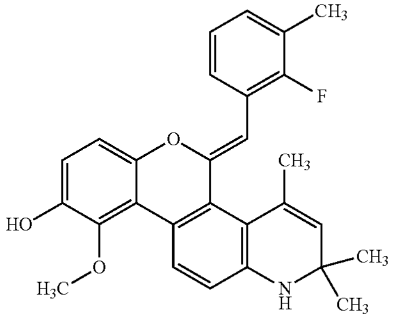 [SMILES: COc1c(O)ccc2c1-c1ccc3c(c1/C(=C/c1cccc(C)c1F)O2)C(C)=CC(C)(C)N3]

MK-5932 has the following structure:

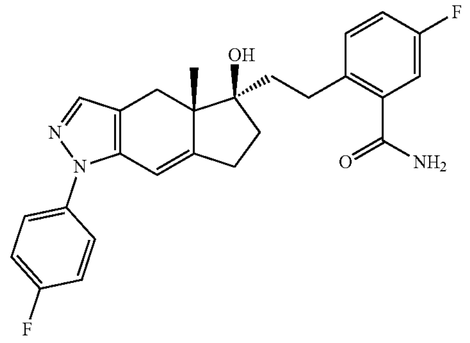 [SMILES: C[C@]12Cc3cnn(-c4ccc(F)cc4)c3C=C1CC[C@@]2(O)CCc1ccc(F)cc1C(N)=O]

Org 214007-0 has the following structure:

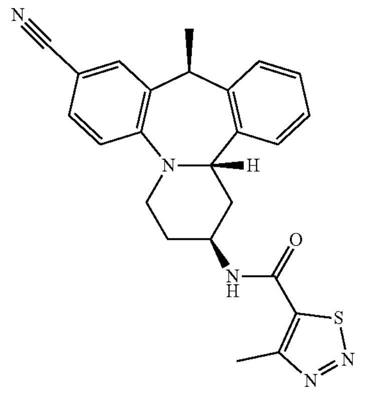 [SMILES: Cc1nnsc1C(=O)N[C@H]1CCN2c3ccc(C#N)cc3[C@@H](C)c3ccccc3[C@@H]2C1]

The chloride salt of compound A has the following structure:

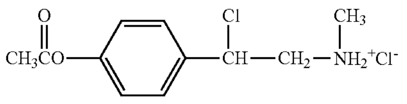

AL-438 has the following structure:

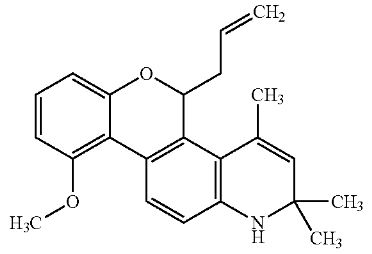 [SMILES: C=CCC1Oc2cccc(OC)c2-c2ccc3c(c21)C(C)=CC(C)(C)N3]

PF-802 has the following structure:

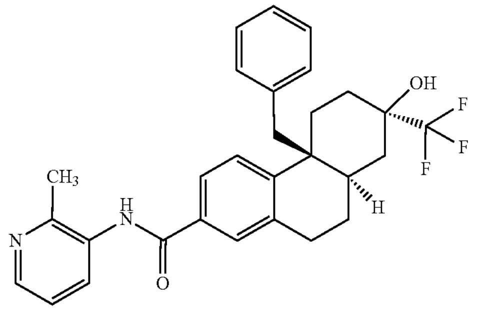 [SMILES: Cc1ncccc1NC(=O)c1ccc2c(c1)CC[C@@H]1C[C@@](O)(C(F)(F)F)CC[C@@]21Cc1ccccc1]

Compound 10 has the following structure:

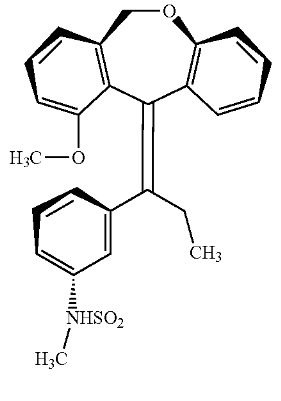

AZD-7594 has the IUPAC name 3-(5-((1R,2S)-2-(2,2-difluoropropanamido)-1-(2,3-dihydrobenzo[b][1,4]dioxin-6-yl)propoxy)-1H-indazol-1-yl)-N-(tetrahydrofuran-3-yl) benzamide and has the following structure:

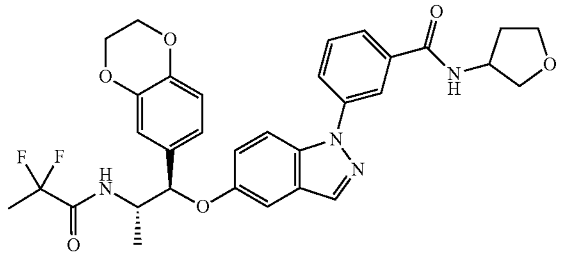 [SMILES: C[C@H](NC(=O)C(C)(F)F)[C@H](Oc1ccc2c(cnn2-c2cccc(C(=O)NC3CCOC3)c2)c1)c1ccc2c(c1)OCCO2]

AZD-5423 has the IUPAC name 2,2,2-Trifluoro-N-((1R,2S)-1-((1-(4-fluorophenyl)-1H-indazol-5-yl)oxy)-1-(3-methoxyphenyl)-2-propanyl)acetamide and has the following structure:

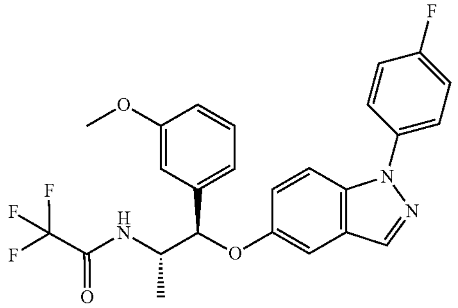 [SMILES: COc1cccc([C@@H](Oc2ccc3c(cnn3-c3ccc(F)cc3)c2)[C@H](C)NC(=O)C(F)(F)F)c1]

AZD-2906 has the IUPAC name N-((1R,2S)-1-((1-(4-fluorophenyl)-1H-indazol-5-yl)oxy)-1-(6-methoxypyridin-3-yl)propan-2-yl)cyclopropanecarboxamide and has the following structure:

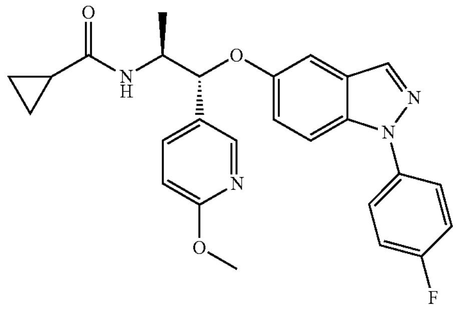 [SMILES: COc1ccc([C@@H](Oc2ccc3c(cnn3-c3ccc(F)cc3)c2)[C@H](C)NC(=O)C2CC2)cn1]

JPT-117968 has the following structure:

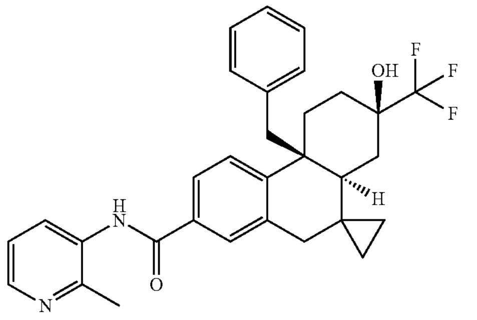 [SMILES: Cc1ncccc1NC(=O)c1ccc2c(c1)CC1(CC1)[C@@H]1C[C@@](O)(C(F)(F)F)CC[C@@]21Cc1ccccc1]

[(3S)-1-[(3R)-5-oxotetrahydrofuran-3-carbonyl]-3-piperidyl]4-[(1R,2S)-1-(4-cyclopropylphenyl)-2-[[(2R)-tetrahydrofuran-2-carbonyl]amino]propoxy]benzoate has the following structure:

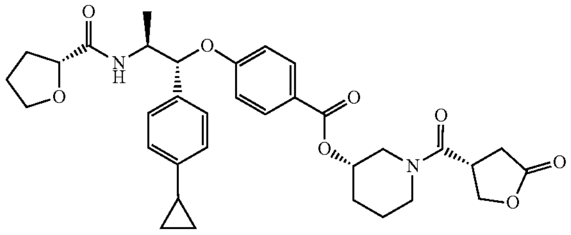 [SMILES: C[C@H](NC(=O)[C@H]1CCCO1)[C@H](Oc1ccc(C(=O)O[C@H]2CCCN(C(=O)[C@H]3COC(=O)C3)C2)cc1)c1ccc(C2CC2)cc1]

WO 2008/076048 A1 discloses compounds of formula (I):

(I)

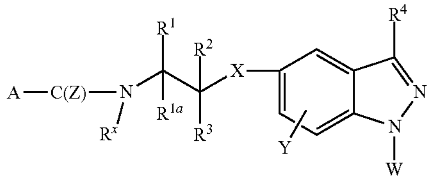

wherein:

A is $C_{1-6}$alkyl, $C_{1-6}$hydroxyalkyl, $C_{1-6}$cyanoalkyl, cyano, $C_{1-6}$nitroalkyl, nitro, $C_{1-6}$alkylS(O)$_n$, $C_{1-6}$alkoxy, $C_{3-7}$cycloalkyl$C_{1-6}$alkyl, $C_{3-7}$cycloalkyl, $C_{3-7}$heterocycloalkyl, $C_{3-7}$heterocycloalkyl$C_{1-6}$alkyl, $C_{1-6}$haloalkyl, $C_{1-6}$alkyl$C_{1-6}$thioalkyl, $C_{1-6}$thioalkyl, $C_{1-6}$alkylO$C_{1-6}$ alkyl, $C_{1-6}$alkylO$C_{1-6}$alkylO, $C_{1-6}$alkylC(O)$C_{1-6}$alkyl, $C_{1-6}$alkylC(O), $C_{1-6}$alkylC(O)O$C_{1-6}$alkyl, $C_{1-6}$alkylC (O)O, $C_{1-6}$alkylOC(O)$C_{1-6}$alkyl, $C_{1-6}$alkylOC(O), HOC(O), $NR^5R^6C_{1-6}$alkyl, $NR^5R^6$, $NR^5R^6C(O)C_{1-6}$alkyl, $NR^5R^6C(O)$, $NR^5R^6OC(O)C_{1-6}$alkyl, $NR^5R^6OC$ (O), $R^7NH$, $C_{5-10}$aryl, $C_{1-3}$alkyl, $C_{5-10}$aryl, $C_{5-10}$heteroaryl, $C_{1-3}$alkyl or $C_{5-10}$heteroaryl, whereby the cycloalkyl, heterocycloalkyl, aryl or heteroaryl may be optionally substituted by one or more substituents independently selected from halo, cyano, hydroxy, $C_{1-4}$alkyl, $C_{1-4}$alkoxy, $C_{1-4}$ haloalkyl, $C_{1-4}$alkylOC(O), $C_{1-4}$alkylO$C_{1-4}$alkyl, $C_{1-4}$alkylS(O)$_2$ and $C_{1-4}$haloalkylO, and $R^x$ is hydrogen, or A forms together with $R^x$ a 5 to 6 membered azacyclic ring optionally having one or more further heteroatoms independently selected from O, N and S;

$R^1$ and $R^{1a}$ are independently selected from hydrogen, $C_{1-4}$alkyl, $C_{1-4}$hydroxyalkyl, $C_{1-4}$alkylO$C_{1-4}$alkyl, $C_{1-4}$alkyl$C_{1-4}$thioalkyl and $C_{1-4}$haloalkyl, or $R^1$ and $R^{1a}$ together are oxo;

$R^2$ is hydrogen or $C_{1-4}$alkyl;

$R^3$ is $C_{5-10}$aryl, $C_{5-10}$aryl$C_{1-4}$alkyl, $C_{5-10}$arylO, $C_{5-10}$arylO$C_{1-4}$alkyl or $C_{5-10}$heteroaryl, which may be optionally substituted by one or more substituents independently selected from B;

B is $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$ cycloalkyl$C_{1-4}$thioalkyl, $C_{3-6}$cycloalkylS, $C_{1-3}$alkylS(O)$_n$$C_{1-4}$ alkyl, $C_{1-3}$alkylS(O), $C_{1-4}$ haloalkyl, $C_{1-4}$haloalkylO, halo, nitro, cyano, $C_{1-4}$alkylO$C_{1-4}$alkylO$C_{1-4}$alkyl, $C_{1-4}$alkylC(O)$C_{1-4}$ alkyl, $C_{1-4}$alkylC(O), $C_{1-4}$alkylC (O)O$C_{1-4}$alkyl, $C_{1-4}$alkylC(O)O, $C_{1-4}$alkylOC(O)$C_{1-4}$ alkyl, $C_{1-4}$alkylOC(O), $NR^8R^9C_{1-4}$alkyl, $NR^8R^9$, $NR^8R^9C(O)C_{1-4}$alkyl, $NR^8R^9C(O)$, $NR^8R^9OC(O)C_{1-4}$ alkyl, $NR^8R^9OC(O)$, $NR^8R^9C(O)OC_{1-4}$alkyl, $NR^8R^9C$ (O)O, $R^9C(O)R^8NC_{1-4}$alkyl, $R^9C(O)R^8NH$, $C_{1-4}$alkylNH, $C_{1-4}$alkylOC(O)NH, $C_{1-4}$alkylC(O)O $C_{1-4}$alkylNH, $C_{1-4}$alkylC(O)$C_{1-4}$ alkylNH, $C_{1-4}$alkylC(O)NH, $NR^8R^9S(O)_nC_{1-4}$alkyl or $NR^8R^9S(O)_n$;

n is 1 or 2;

$R^4$ is hydrogen, hydroxy, halo, $C_{1-4}$alkyl or

W is hydrogen, or phenyl, $C_{1-4}$alkyl, $C_{3-7}$cycloalkyl, thienyl, isoxazolyl, pyrazolyl, pyridinyl, pyridazinyl or pyrimidinyl all of which are optionally substituted by one or more substituents independently selected from $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkyl$C_{1-4}$thioalkyl, $C_{3-6}$cycloalkylS, $C_{3-6}$cycloalkyl, $C_{3-6}$cycloalkyl$C_{1-4}$alkyl, $C_{3-6}$heterocycloalkyl, $C_{3-6}$heterocycloalkyl$C_{1-4}$alkyl, $C_{1-4}$alkylS(O)$_n$$C_{1-4}$alkyl, $C_{1-4}$alkylS(O)$_n$, $C_{1-4}$haloalkyl, $C_{1-4}$haloalkylO, halo, nitro, cyano, $C_{1-4}$alkylO$C_{1-4}$alkyl, $C_{1-4}$alkylO$C_{1-4}$alkylO$C_{1-4}$alkyl, $C_{1-4}$alkylC(O)$C_{1-4}$alkyl, $C_{1-4}$alkylC(O), $C_{1-4}$alkylC(O)O$C_{1-4}$alkyl, $C_{1-4}$alkylC(O)O, $C_{1-4}$alkylOC(O)$C_{1-4}$alkyl, $C_{1-4}$alkylOC(O), $NR^{10}R^{11}$, $NR^{10}R''C(O)C_{1-4}$alkyl, $NR^{10}R^{11}C(O)$, $NR^{10}R^{11}C(O)O$, $NR^{10}R^{11}C_{1-4}$alkyl, $NR^{10}R^{11}OC(O)$, $R^{11}C(O)R^{10}NC_{1-4}$alkyl, $R^{11}C(O)R^{10}NH$, $C_{1-4}$alkylOC(O)$C_{1-4}$alkylNH, $C_{1-4}$alkylOC(O)NH, $C_{1-4}$alkylC(O)O$C_{1-4}$alkyMH, $C_{1-4}$alkylC(O)$C_{1-4}$ alkylNH, $C_{1-4}$alkylC(O)NH, $NR^{10}R^{11}S(O)_nC_{1-4}$ alkyl or $NR^{10}R^{11}S(O)_n$;

X is $CH_2$, O, S, S(O)$_n$, NH or N$C_{1-4}$alkyl;

Y is hydrogen, halo, $C_{1-4}$thioalkyl, $C_{1-4}$haloalkyl, $C_{1-4}$ haloalkylO, nitro, cyano, hydroxy, $R^{12}C(O)$, $R^{12}OC(O)$, $R^{12}C(O)O$, $C_{1-6}$alkylS(O)$_n$, $R^{12}R^{13}NS(O)_n$, benzyloxy, imidazolyl, $C_{1-4}$alkylNHC(O), $NR^{12}R^{13}C(O)$, $C_{1-4}$alkylC(O)NH or $NR^{12}R^{13}$;

Z is O or S;

$R^5$, $R^6$, $R^8$, $R^9$, $R^{10}$ $R^{11}$, $R^{12}$ and $R^{13}$ are independently selected from hydrogen, $C_{1-6}$alkylC(O), $NHR^7C(O)$ and $C_{1-6}$alkyl; and $R^7$ is hydrogen, $C_{1-6}$alkyl, $C_{1-6}$alkylC(O)O$C_{1-3}$alkyl, $C_{1-6}$alkylC(O)O, $C_{1-6}$alkylOC(O)$C_{1-3}$alkyl, $C_{1-6}$alkylOC(O), $C_{1-6}$alkylC(O), $C_{5-10}$heteroaryl$C_{1-3}$alkyl, $C_{5-10}$heteroaryl, $C_{5-10}$aryl$C_{1-3}$alkyl, $C_{5-10}$aryl, $C_{3-6}$cycloalkyl$C_{1-3}$alkyl or $C_{3-6}$cycloalkyl;

or a pharmaceutically acceptable salt thereof.

Badarau E. et al. (European Journal of Medicinal Chemistry, 2019, 161: 354-363) spirocyclic analogues of fluorocortivazol which can be used according to the present invention. Exemplary compounds and their synthesis, which can be used according to the present invention are:

compounds of formulas 8a-e and 9a-e:

8a-e

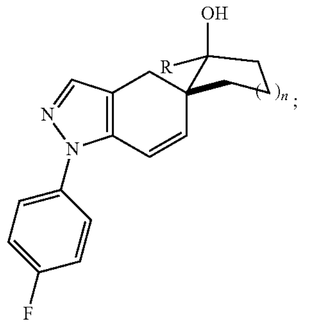

-continued 9a-e

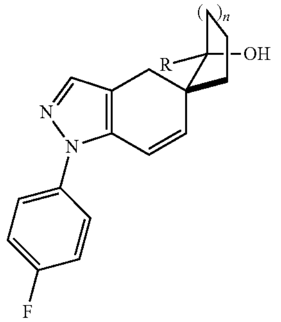

wherein:

in compounds 8a, 8b: n=1, R=phenyl, in compounds 8b, 9b: n=2, R=dibenzyl, in compounds 8c, 9c: n=3, R=phenyl, in compounds 8d, 9d: n=3, R=phenyl, in compounds 8e, 9e: n=3, R=benzyl.

compounds of formulas 10a-c:

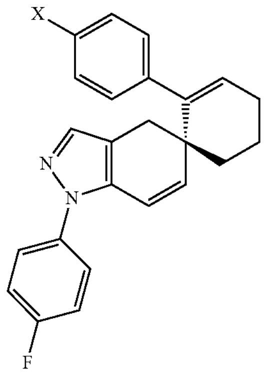

10a, X = H
10b, X = OH
10c, X = OMe and compounds of formulas 11a-b, 12a-b, 13a-b and 14a:

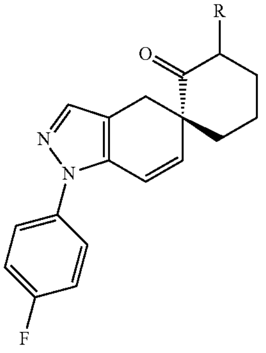

+

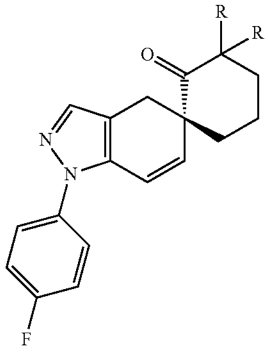

11a,b 12a,b (b)

(c)

-continued

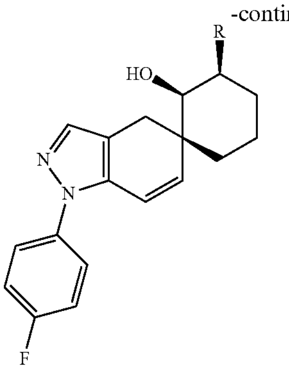

13a,b

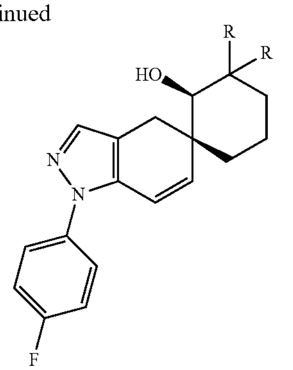

14a wherein in compounds 11a, 12a, 13a, 14a: R=benzyl in compounds 11b, 12b, 13b: R=propargyl.

BI-54903 is also known as tiotropium, in particular the bromide salt thereof.

BI-607812 has the following structure:

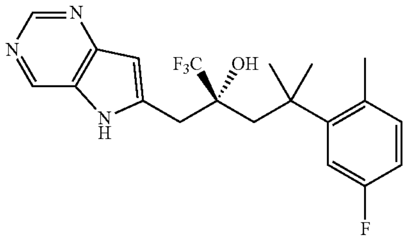 [SMILES: Cc1ccc(F)cc1C(C)(C)C[C@@](O)(Cc1cc2ncncc2[nH]1)C(F)(F)F]

GW870086X has the following structure:

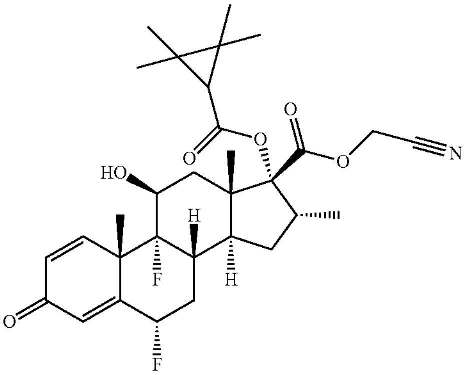

PF-00251802 is the active metabolite of active metabolite of fosdagrocorat. PF-00251802 is also known as dagrocorat and has the following structure:

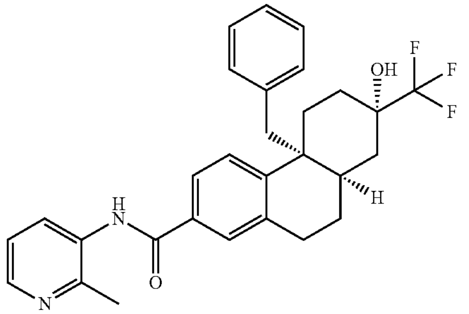 [SMILES: Cc1ncccc1NC(=O)c1ccc2c(c1)CC[C@@H]1C[C@](O)(C(F)(F)F)CC[C@]21Cc1ccccc1]

Cortivazol has the following structure:

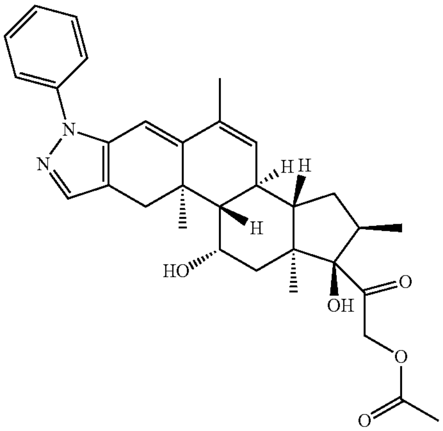

Fluorocortivazol is known in the art and is for example disclosed in Badarau E. (2019; supra).

WO 2008/021728 A2, WO 2008/021729 A2, WO 2008/005686 A2, WO 2008/027796 A2, WO 2009/042377 A1, WO 2010/123769 A1, WO 2009/023471 A2, WO 2012/170175 A1 and WO 2008/033655 A2 disclose DIGRA compounds of formula (I):

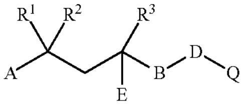

(I)

wherein A and Q are independently selected from the group consisting of unsubstituted and substituted aryl and heteroaryl groups, unsubstituted and substituted cycloalkyl and heterocycloalkyl groups, unsubstituted and substituted cycloalkenyl and heterocycloalkenyl groups, unsubstituted and substituted cycloalkynyl and heterocycloalkynyl groups, and unsubstituted and substituted heterocyclic groups; $R^1$ and $R^2$ are independently selected from the group consisting of hydrogen, unsubstituted $C_1$-$C_{15}$ (alternatively, $C_1$-$C_{10}$ or $C_1$-$C_5$, or $C_1$-$C_3$) linear or branched alkyl groups, substituted $C_1$-$C_{15}$ (alternatively, $C_1$-$C_{10}$, or $C_1$-$C_5$, or $C_1$-$C_3$) linear or branched alkyl groups, unsubstituted $C_3$-$C_{15}$ cycloalkyl groups, and substituted $C_3$-$C_{15}$ (alternatively, $C_3$-$C_6$, or $C_3$-$C_5$) cycloalkyl groups; $R^3$ is selected from the group consisting of hydrogen, unsubstituted $C_1$-$C_{15}$ (alternatively, $C_1$-$C_{10}$, or $C_1$-$C_5$, or $C_1$-$C_3$) linear or branched alkyl groups, substituted $C_1$-$C_{15}$ (alternatively, $C_1$-$C_{10}$, or $C_1$-$C_5$, or $C_1$-$C_3$) linear or branched alkyl groups, unsubstituted $C_3$-$C_{15}$ (alternatively, $C_3$-$C_6$, or $C_3$-$C_5$) cycloalkyl and heterocycloalkyl groups, substituted $C_3$-$C_{15}$ (alternatively, $C_3$-$C_6$, or $C_3$-$C_5$) cycloalkyl and heterocycloalkyl groups, aryl groups, heteroaryl groups, and heterocyclylic groups; B comprises a carbonyl, amino, divalent hydrocarbon, or heterohydrocarbon group; E is hydroxy or amino group; and D is absent or comprises a carbonyl group, —NH—, or —NR'—, wherein R' comprises an unsubstituted or substituted $C_1$-$C_{15}$ (alternatively, $C_1$-$C_{10}$, or $C_1$-$C_5$, or $C_1$-$C_3$) linear or branched alkyl group; and wherein $R^1$ and $R^2$ together may form an unsubstituted or substituted $C_3$-$C_{15}$ cycloalkyl group.

In one embodiment, B can comprise one or more unsaturated carbon-carbon bonds.

In another embodiment, B can comprise an alkylenecarbonyl, alkyleneoxycarbonyl, alkylenecarbonyloxy, alkyleneoxycarbonylamino, alkyleneamino, alkenylenecarbonyl, alkenyleneoxycarbonyl, alkenylenecarbonyloxy, alkenyleneoxycarbonylamino, alkenyleneamino, alkynylenecarbonyl, alkynyleneoxycarbonyl, alkynylenecarbonyloxy, alkynyleneoxycarbonylamino, alkynyleneamino, arylcarbonyloxy, aryloxycarbonyl, or ureido group.

In still another embodiment, A and Q are independently selected from the group consisting of aryl and heteroaryl groups substituted with at least a halogen atom, cyano group, hydroxy group, or $C_1$-$C_{10}$ alkoxy group (alternatively, $C_1$-$C_5$ alkoxy group, or $C_1$-$C_3$ alkoxy group); $R^1$, $R^2$, and $R^3$ are independently selected from the group consisting of unsubstituted and substituted $C_1$-$C_5$ alkyl groups (preferably, $C_1$-$C_3$ alkyl groups); B is a $C_1$-$C_5$ alkylene group (alternatively, $C_1$-$C_3$ alkyl groups); D is the —NH— or —NR'— group, wherein R' is a $C_1$-$C_5$ alkyl group (preferably, $C_1$-$C_3$ alkyl group); and E is the hydroxy group.

In yet another embodiment, A comprises a dihydrobenzofuranyl group substituted with a halogen atom; Q comprises a quinolinyl or isoquinolinyl group substituted with a $C_1$-$C_{10}$ alkyl group; $R^1$ and $R^2$ are independently selected from the group consisting of unsubstituted and substituted $C_1$-$C_5$ alkyl groups (preferably, $C_1$-$C_3$ alkyl groups); B is a $C_1$-$C_3$ alkylene group; D is the —NH— group; E is the hydroxy group; and $R^3$ comprises a completely halogenated $C_1$-$C_{10}$ alkyl group (preferably, completely halogenated $C_1$-$C_5$ alkyl group; more preferably, completely halogenated $C_1$-$C_3$ alkyl group).

In still another embodiment, A comprises a dihydrobenzofuranyl group substituted with a fluorine atom; Q comprises a quinolinyl or isoquinolinyl group substituted with a methyl group; $R^1$ and $R^2$ are independently selected from the group consisting of unsubstituted and substituted $C_1$-$C_5$ alkyl groups; B is a $C_1$-$C_3$ alkylene group; D is the —NH— group; E is the hydroxy group; and R comprises a trifluoromethyl group.

Further, a DIGRA compound of formula (IV) is disclosed, which is mapracorat:

(IV)

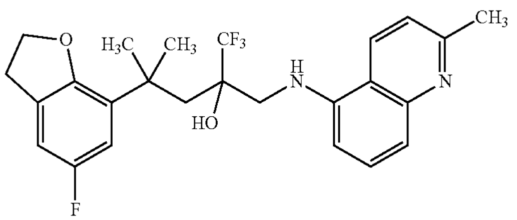

WO 2013/126156 A1 discloses NO-donating DIGRA compounds.

BI653048 is the compound (R)-2-(4-((5-(Ethylsulfonyl)-1H-pyrrolo[2,3-c]pyridin-2-yl)methyl)-5,5,5-trifluoro-4-hydroxy-2-methylpentan-2-yl)-5-fluorobenzamide.

The phosphate salt thereof has the following structure:

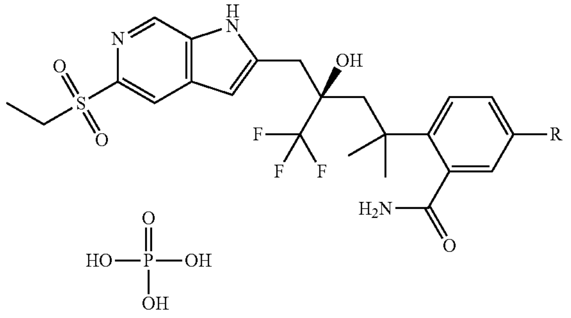

BI653048 and related compounds as well as their synthesis are disclosed in WO 2009/149139 A1 and EP 2 300 472.

WO 2017/046096 discloses the following SEGRM compounds as well as their synthesis. The SEGRM compounds in WO 2017/046096 are particularly preferred for use of the invention:

A compound of following formula (I) below:

(I)

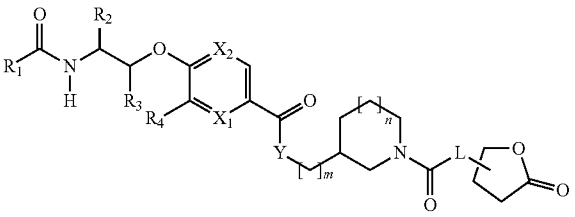

wherein $R_1$ is selected from the group consisting of 5- and 6-membered heteroaryl, ($C_1$-$C_6$)alkyl, ($C_3$-$C_6$)cycloalkyl, (4-6)-membered heterocycloalkyl and phenyl, wherein said 5- and 6-membered heteroaryl, ($C_1$-$C_6$)alkyl, ($C_3$-$C_6$)cycloalkyl, (4-6)-membered heterocycloalkyl and phenyl is optionally substituted with one or more substituents independently selected from ($C_1$-$C_4$)alkyl, ($C_1$-$C_4$)alkoxy, halogen, hydroxyl and cyano;

$R_2$ is selected from ($C_1$-$C_3$)alkyl and halo($C_1$-$C_3$)alkyl;

$R_3$ is selected from phenyl, 5-membered heteroaryl and 6-membered heteroaryl, wherein said phenyl, 5-membered heteroaryl and 6-membered heteroaryl are optionally substituted with one or more substituents independently selected from $R_5$;

$R_4$ is selected from hydrogen, halogen, ($C_1$-$C_4$)alkyl and halo($C_1$-$C_4$)alkyl;

$R_5$ is selected from halogen, cyano, ($C_1$-$C_6$)alkyl, ($C_3$-$C_6$) cycloalkyl, ($C_1$-$C_6$)alkoxy, halo($C_1$-$C_6$)alkyl, halo($C_1$-$C_6$)alkoxy, hydroxy($C_1$-$C_6$)alkyl, phenyl, 5-membered heteroaryl, 6-membered heteroaryl and —$S(O)_2R_a$, wherein $R_a$ represents ($C_1$-$C_4$)alkyl;

$X_1$ is selected from CH, C($R_b$) and N, wherein $R_b$ represents halogen, ($C_1$-$C_4$)alkyl or halo($C_1$-$C_4$)alkyl;

$X_2$ is selected from CH and N;

Y is selected from —NH— and —O—;

m is 0 or 1; n is 0 or 1;

L represents a bond, —O—, —NH— or —N($R_c$)—, wherein $R_c$ represents ($C_1$-$C_4$)alkyl;

or pharmaceutically acceptable salts, hydrates or solvates thereof.

Preferably, the SEGRM compound for use of the invention is selected from the following compounds:

N-[(3S)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, 5-[(1R,2S)-1-(4-cyclopropylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-(2,2-difluoropropanoylamino)propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-3-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-5-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]thiazole-4-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]-3-methyl-isoxazole-5-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-5-carboxamide, 5-[(1R,2S)-1-(4-cyclopropylphenyl)-2-[[(2S)-2-hydroxybutanoyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[[(2R)-2-hydroxypropanoyl]amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-5-carboxamide, 5-[(1R,2S)-1-(4-cyclopropylphenyl)-2-[[(2R)-2-hydroxybutanoyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-methoxyacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-hydroxy-2-methyl-propanoyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-(3-hydroxypropanoylamino)propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(1-hydroxycyclobutanecarbonyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(1-hydroxycyclopropanecarbonyl)amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-4-carboxamide, 5-[(1R,2S)-1-(4-cyclopropylphenyl)-2-[[(2S)-tetrahydrofuran-2-carbonyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-hydroxyacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[[(2R)-tetrahydrofuran-2-carbonyl]amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-3-carboxamide,

[(3S)-1-[(3R)-5-oxotetrahydrofuran-3-carbonyl]-3-piperidyl]-4-[(1R,2S)-1-(4-cyclopropylphenyl)-2-[(2,2,2-trifluoroacetyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-(1,2,5-thiadiazole-3-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-[(5-methylthiazole-2-carbonyl)amino]pro poxy]benzoate,

[(3S)-1-[(3R)-5-oxotetrahydrofuran-3-carbonyl]-3-piperidyl]-4-[(1R,2S)-1-(4-cyclopropylphenyl)-2-(thiazole-5-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-[(4-methyl-1,2,5-oxadiazole-3-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(5-methylthiazole-4-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(4-methylthiazole-5-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(5-methyl-1,3,4-oxadiazole-2-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(4-methylthiadiazole-5-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(4-methyloxazole-5-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(2-methoxyacetyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(2-methylpyrazole-3-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(2-methylthiazole-5-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[[(2R)-tetrahydrofuran-2-carbonyl]amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(3-methyltriazole-4-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-(1,2,4-oxadiazole-3-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-[(I-methylimidazole-2-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(3-methylisoxazole-5-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(5-methyl-1,2,4-oxadiazole-3-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(I-methylimidazole-4-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-(isothiazole-3-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-[(3-methylisoxazole-4-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-(thiazole-2-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-(isothiazole-5-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-[(5-methylisothiazole-4-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-(oxazole-2-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-(oxazole-5-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-(isoxazole-3-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-(thiadiazole-4-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-[(5-methylisoxazole-3-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-(isoxazole-5-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-(thiazole-4-carbonylamino)propoxy]benzoate,

[(3S)-1-[(3R)-5-oxotetrahydrofuran-3-carbonyl]-3-piperidyl]-4-[(1R,2S)-1-(4-cyclopropylphenyl)-2-[(3-methyl-1,2,4-oxadiazole-5-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-[(1-methylpyrazole-3-carbonyl)amino]propoxy]benzoate,

[(3S)-1-[(3R)-5-oxotetrahydrofuran-3-carbonyl]-3-piperidyl]-4-[(1R,2S)-1-(4-cyclopropylphenyl)-2-(2,2-difluoropropanoylamino)propoxy]benzoate, N-[(3R)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(2R)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3S)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3S)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(3R)-5-oxotetrahydrofuran-3-carbonyl]pyrrolidin-3-yl]-5-[(1R,2S)-1-(p-tolyl)-2-[(2,2,2-trifluoroacetyl)amino]propoxy]pyridine-2-carboxamide, 5-[(1R,2S)-1-(4-ethylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-bromophenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, N-[(3S)-1-[(3R)-5-oxotetrahydrofuran-3-carbonyl]-3-piperidyl]-5-[(1R,2S)-1-(4-phenyl phenyl)-2-[(2,2,2-trifluoroacetyl)amino]propoxy]pyridine-2-carboxamide, N-[(3S)-1-[(3R)-5-oxotetrahydrofuran-3-carbonyl]-3-piperidyl]-4-[(1R,2S)-1-(p-tolyl)-2[(2,2,2-trifluoroacetyl)amino]propoxy]benzamide,

[(3S)-1-[(3R)-5-oxotetrahydrofuran-3-carbonyl]-3-piperidyl]-4-[(1R,2S)-1-(p-tolyl)-2-[(2,2,2-trifluoroacetyl)amino]propoxy]benzoate, N-[(3S)-1-[[(3S)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide, N-[(3S)-1-[[(3R)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide,

[(3S)-2-oxotetrahydrofuran-3-yl](3S)-3-[[5-[(1R,2S)-1-(p-tolyl)-2-[(2,2,2-trifluoroacetyl)amino]propoxy]pyridine-2-carbonyl]amino]piperidine-1-carboxylate,

[(3R)-2-oxotetrahydrofuran-3-yl](3S)-3-[[5-[(1R,2S)-1-(p-tolyl)-2-[(2,2,2-trifluoroacetyl)amino]propoxy]pyridine-2-carbonyl]amino]piperidine-1-carboxylate,

[(3S)-5-oxotetrahydrofuran-3-yl](3S)-3-[[5-[(1R,2S)-1-(p-tolyl)-2-[(2,2,2-trifluoroacetyl)amino]propoxy]pyridine-2-carbonyl]amino]piperidine-1-carboxylate or

[(34)-5-oxotetrahydrofuran-3-yl](3S)-3-[[5-[(1R,2S)-1-(p-tolyl)-2-[(2,2,2-trifluoroacetyl)amino]propoxy]pyridine-2-carbonyl]amino]piperidine-1-carboxylate or pharmaceutically acceptable salts, hydrates or solvates thereof.

In a more preferred embodiment, [(3S)-1-[(3R)-5-oxotetrahydrofuran-3-carbonyl]-3-piperidyl]-4-[(1R,2S)-1-(4-cyclopropylphenyl)-2-[[(2R)-tetrahydrofuran-2-carbonyl]amino]propoxyl benzoate or a pharmaceutically acceptable salt thereof can be used according to the invention. The compound corresponds to "Compound 37" in WO 2017/046096 and has the following structure:

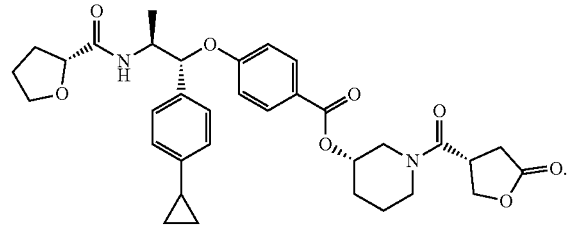 [SMILES: C[C@H](NC(=O)[C@H]1CCCO1)[C@H](Oc1ccc(C(=O)O[C@H]2CCCN(C(=O)[C@H]3COC(=O)C3)C2)cc1)c1ccc(C2CC2)cc1]

The following three SEGRM compounds as well as their synthesis are disclosed in WO 2009/065503.

5-{[(1S,2S)-1-(2-chloro-3-fluoro-4-methoxyphenyl)-3,3,3-trifluoro-2-hydroxy-2-(methoxymethyl)propyl]amino}-7-fluoro-1H-quinolin-2-one has the following structure:

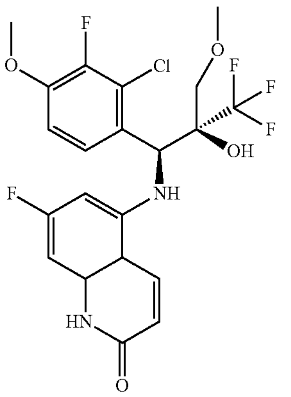 [SMILES: COC[C@@](O)([C@@H](NC1=CC(F)=CC2NC(=O)C=CC12)c1ccc(OC)c(F)c1Cl)C(F)(F)F]

The compound is known as example 5 of WO 2009/065503 A (without stereochemistry as racemate) and can be obtained from the racemic form by chiral HPLC on Chiralpak IC 5 μm with the eluent hexane/ethanol (4:1).

In an even more preferred embodiment, 5-{[(1S,2S)-1-(2-chloro-3-fluoro-4-methoxyphenyl)-3,3,3-trifluoro-2-hydroxy-2-(methoxymethyl)propyl]amino}-7-fluoro-1H-quinolin-2-one or a pharmaceutically acceptable salt thereof can be used according to the invention.

5-{(1S,2S)[1-(2-chloro-3-fluoro-4-methoxyphenyl)-3,3,3-trifluoro-2-hydroxy-2-(hydroxymethyl)propyl]amino}-7-fluoro-1H-quinolin-2-one has the following structure:

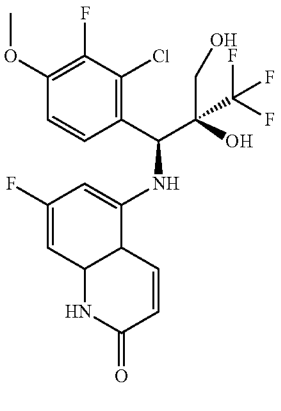 [SMILES: COc1ccc([C@H](NC2=CC(F)=CC3NC(=O)C=CC23)[C@](O)(CO)C(F)(F)F)c(Cl)c1F]

The compound is known as example 7 of WO 2009/065503 A (without stereochemistry as racemate) and can be obtained from the racemic form by chiral HPLC on Chiralpak IC 5 μm with the eluent hexane/ethanol (4:1).

In a more preferred embodiment, 5-{(1S,2S)[1-(2-chloro-3-fluoro-4-methoxyphenyl)-3,3,3-trifluoro-2-hydroxy-2-(hydroxymethyl)propyl]amino}-7-fluoro-1H-quinolin-2-one or a pharmaceutically acceptable salt thereof can be used according to the invention.

5-{(1S,2R)[1-(2-chloro-3-fluoro-4-methoxyphenyl)-3,3,3-trifluoro-2-hydroxy-2-([methylsulfanyl]methyl)propyl]amino}-1H-chinoline-2-one has the following formula:

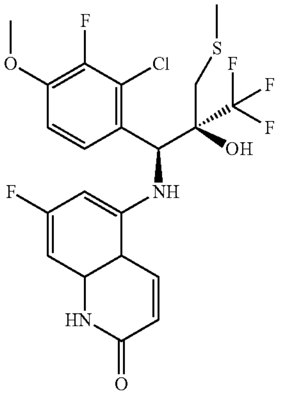 [SMILES: COc1ccc([C@H](NC2=CC(F)=CC3NC(=O)C=CC23)[C@](O)(CSC)C(F)(F)F)c(Cl)c1F]

The compound is known as example 3 of WO 2009/065503 (without stereochemistry as racemate) and can be obtained from the racemic form by chiral HPLC on Chiralpak IC 5 μm with the eluent hexane/ethanol (4:1).

In a more preferred embodiment, 5-{(1S,2R)[1-(2-chloro-3-fluoro-4-methoxyphenyl)-3,3,3-trifluoro-2-hydroxy-2-([methylsulfanyl]methyl)propyl]amino}-1H-chinoline-2-one or a pharmaceutically acceptable salt thereof can be used according to the invention.

These SEGRM compounds as well as their synthesis are disclosed in WO 2009/065503.

Accordingly, in one embodiment, the use of the compounds of Formula (I) is preferred according to the invention:

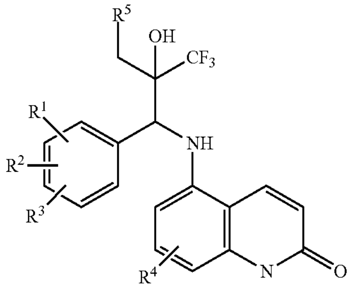

(I)

wherein $R^1$ and $R^2$ independently of one another, mean a hydrogen atom, a hydroxy group, a halogen atom, an optionally substituted ($C_1$-$C_{10}$)-alkyl group, an optionally substituted ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$together mean a group that is selected from the groups —O—$(CH_2)_p$—O—, —O—$(CH_2)_p$—$CH_2$—, —O—CH═CH—, —$(CH_2)_{p+2}$—, —NH—$(CH_2)_{p+1}$, —N($C_1$-$C_3$-alkyl)-$(CH_2)_{p+1}$, and —NH—N═CH—, whereby p=1 or 2, and the terminal oxygen atoms and/or carbon atoms and/or nitrogen atoms are linked to directly adjacent ring-carbon atoms, or $NR^6R^7$, whereby $R^6$ and $R^7$, independently of one another, mean hydrogen, $C_1$-$C_5$-alkyl or (CO)—($C_1$-$C_5$)-alkyl, $R^3$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^4$ means a hydrogen, halogen, hydroxy, ($C_1$-$C_5$)-alkyl, ($C_1$-$C_5$)-alkoxy, ($C_1$-$C_5$)-alkylthio, ($C_1$-$C_5$)-perfluoroalkyl, cyano, nitro, $NR^6R^7$, $COOR^9$, (CO)$NR^6R^7$ or a ($C_1$-$C_5$)-alkylene)-O—(CO)—($C_1$-$C_5$)-alkyl group $R^5$ means a group selected from —($C_1$-$C_{10}$)alkyl, which may be optionally partially or completely halogenated, —($C_2$-$C_{10}$)alkenyl, —($C_2$-$C_{10}$)alkynyl, ($C_3$-$C_7$)cycloalkyl-($C_1$-$C_8$)alkyl, ($C_3$-$C_7$)cycloalkyl-($C_1$-$C_8$)alkyenyl, ($C_3$-$C_7$)cycloalkyl-($C_2$-$C_8$)alkynyl, heterocyclyl-($C_1$-$C_8$)alkyl, heterocyclyl-($C_1$-$C_8$)alkenyl, heterocyclyl-($C_2$-$C_8$)alkynyl,

—$R^8$, $R^8$—($C_1$-$C_8$)alkyl, $R^8$—($C_2$-$C_8$)alkenyl, $R^8$—($C_2$-$C_8$)alkynyl, —S—($C_1$-$C_{10}$)-alkyl, —$SO_2$—($C_1$-$C_{10}$)-alkyl

—S—$R^8$,

—$SO_2$—$R^8$,

—CN

-Hal,

—O—($C_1$-$C_{10}$)-alkyl,

—$NR^6R^7$, wherein $R^6$, $R^7$ have the meaning defined above

—O—$R^8$,

—OH with the exception of —$CH(CH_3)_2$, or —$C(CH_3)$═$CH_2$ $R^8$ means an aryl group which may optionally be substituted by 1-3 hydroxy, halogen, $C_1$-$C_5$-alkyl, $C_1$-$C_5$-alkoxy, cyano, $CF_3$, nitro, COO($C_1$-$C_5$)-alkyl) or C(O)$OCH_2$-phenyl or a heteroaryl group whereby the heteroaryl group may contain 1-3 hetero atoms which may optionally be substituted by 1-3 alkyl groups, hydroxy, halogen, cyano or $C_1$-$C_5$-alkoxy groups, and their salts, solvates or salts of solvates.

More preferred is the use of compounds of Formula (I) wherein:

$R^1$ and $R^2$ independently of one another, mean a hydrogen atom, a hydroxy group, a halogen atom, an optionally substituted ($C_1$-$C_{10}$)-alkyl group, an optionally substituted ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$ together mean a group that is selected from the groups —O—$(CH_2)_p$—O—, —O—$(CH_2)_p$—$CH_2$—, —O—CH═CH—, —$(CH_2)_{p+2}$—, —NH—$(CH_2)_{p+1}$, —N($C_1$-$C_3$-alkyl)-$(CH_2)_{p+}$i, and —NH—N═CH—, whereby p=1 or 2, and the terminal oxygen atoms and/or carbon atoms and/or nitrogen atoms are linked to directly adjacent ring-carbon atoms, or $NR^6R^7$, whereby $R^6$ and $R^7$, independently of one another mean hydrogen, $C_1$-$C_5$-alkyl or (CO)—($C_1$-$C_5$)-alkyl, $R^3$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^4$ means a hydrogen atom, a hydroxy group, a halogen atom, $R^5$ means a group selected from —($C_1$-$C_{10}$)alkyl, which may be optionally partially or completely halogenated —($C_2$-$C_{10}$)alkenyl, —($C_2$-$C_{10}$)alkynyl, ($C_3$-$C_7$)cycloalkyl-($C_1$-$C_8$)alkyl, ($C_3$-$C_7$)cycloalkyl-($C_2$-$C_8$)alkenyl, ($C_3$-$C_7$)cycloalkyl-($C_2$-$C_8$)alkynyl, heterocyclyl-($C_1$-$C_8$)alkyl, heterocyclyl-($C_2$-$C_8$)alkenyl, heterocyclyl-($C_2$-$C_8$)alkynyl,

—$R^8$, $R^8$—($C_1$-$C_8$)alkyl, $R^8$—($C_2$-$C_8$)alkenyl, $R^8$—($C_2$-$C_8$)alkynyl, —S—($C_1$-$C_{10}$)-alkyl,

—S—$R^8$,

—$SO_2$—$R^8$,

—$SO_2$—($C_1$-$C_{10}$)-alkyl,

—CN,

-Hal,

—O—(C1-C1o)-alkyl,

—$NR^6R^7$ wherein $R^8$, $R^7$ have the meaning indicated above

—O—$R^8$,

—OH with the exception of —$CH(CH_3)_2$, or —$C(CH_3)=CH_2$ $R^8$ means an aryl which may optionally be substituted with 1-3 alkyl, hydroxy, halogen, cyano or $C_1$-$C_5$-alkoxy groups or a heteroaryl group wherein the heteroaryl group may contain 1-3 heteroatoms which may optionally be substituted with 1-3 alkyl, hydroxy, halogen, cyano or $C_1$-$C_5$-alkoxy groups, n means an integer selected from 1, 2, 3, 4, 5 and their salts, solvates or salts of solvates.

More preferred is the use of compounds of Formula (I) wherein $R^1$ and $R^2$, independently of each other, mean a hydrogen atom, a hydroxyl group, a halogen atom, an optionally substituted ($C_1$-$C_{10}$)-alkyl group, an optionally substituted ($C_1$-$C_{10}$)-alkoxy group, a ($C_1$-$C_5$)-perfluoroalkyl group, a cyano group, or $NR^6R^7$, whereby $R^6$ and $R^7$, independently of one another, mean hydrogen, $C_1$-$C_5$-alkyl or (CO)—($C_1$-$C_5$)-alkyl, $R^3$ means a hydrogen atom, a hydroxy group, a halogen atom, a cyano group, an optionally substituted ($C_1$-$C_{10}$)-alkyl group, a ($C_1$-$C_{10}$)-alkoxy group, or a ($C_1$-$C_5$)-perfluoroalkyl group, $R^4$ means hydrogen, $C_1$-$C_3$-alkyl, $C_1$-$C_3$-alkoxy, hydroxy, halogen, $R^5$ means a group selected from —($C_1$-$C_{10}$)-alkyl, which may be optionally partially or completely halogenated —($C_2$-$C_{10}$)-alkenyl, —($C_2$-$C_{10}$)-alkynyl, —($C_3$-$C_7$)cycloalkyl-($C_1$-$C_8$)alkyl, —($C_3$-$C_7$)cycloalkyl-($C_2$-$C_8$)alkenyl, —S—($C_1$-$C_{10}$)-alkyl, —$SO_2$—($C_1$-$C_{10}$)-alkyl, —CN, -Hal, —O—($C_1$-$C_{10}$)-alkyl, —$NR^6R^7$ wherein $R^8$, $R^7$ have the meaning defined above, —OH with the exception of —$CH(CH_3)_2$, or —$C(CH_3)=CH_2$ and their salts, solvates or salts of solvates.

A further aspect of the invention are compounds of general formula I according to claim 1, wherein $R^1$, $R^2$ and $R^3$ are independently of one another hydrogen, fluorine, chlorine, bromine, a cyano group, a methoxy group, a ethoxy group, a hydroxy group, $R^4$ is hydrogen, $C_1$-$C_3$-alkyl, halogen, $R^5$ is hydroxyl group, chlorine, —S—$CH_3$, —S—$CH_2$—$CH_3$, —S—$CH_2$—$CH_2$—$CH_3$, —O—$CH_3$ or —O—$CH_2$—$CH_3$, —O—$CH_2$—$CH_2$—$CH_3$, —N—$(CH_3)_2$, —N—$(CH_2—CH_3)_2$ and their salts, solvates or salts of solvates.

A further aspect of the invention are compounds of general formula I according to claim 1, wherein $R^1$, $R^2$ and $R^3$ are independently of one another hydrogen, fluorine, chlorine, bromine, a cyano group, a methoxy group, a ethoxy group, a hydroxyl group, $R^4$ is hydrogen, $C_1$-$C_3$-alkyl, halogen, $R^5$ is a hydroxyl group, chlorine, —S—$CH_3$, —S—$CH_2$—$CH_3$, —S—$CH_2$—$CH_2$—$CH_3$, —O—$CH_3$, —O—$CH_2$—$CH_3$, —O—$CH_2$—$CH_2$—$CH_3$ or $N(CH_3)_2$ and their salts, solvates or salts of solvates.

Even more preferred is the use of compounds of Formula (I) wherein $R^1$ and $R^2$, and $R^3$, are independently of each other, hydrogen, fluorine, chlorine, bromine, a cyano group, a methoxy group, a ethoxy group, a hydroxyl group, $R^4$ is hydrogen, $CrC_3$-alkyl, halogen, $R^5$ is a hydroxyl group, chlorine, —S—$CH_3$, —S—$CH_2$—$CH_3$, —S—$CH_2$—$CH_2$—$CH_3$, —O—$CH_3$ or —O—$CH_2$—$CH_3$, —O—$CH_2$—$CH_2$—$CH_3$ and their salts, solvates or salts of solvates.

Still even more preferred is the use of compounds of Formula (I), wherein $R^1$ and $R^2$ are independently of one another hydrogen, fluorine, chlorine, a methoxy group, a hydroxyl group, $R^3$ is hydrogen, fluorine, chlorine or a methoxy group, $R^4$ is hydrogen or fluorine, $R^5$ is a hydroxy group, a chlorine atom, —S—$CH_3$, —S—$CH_2$—$CH_3$, —O—$CH_{3i}$—O—$CH_2$—$CH_3$ or $N(CH_3)_2$ and their salts, solvates or salts of solvates.

A further aspect of the invention are compounds of general formula I according to claim 1, wherein $R^1$ and $R^2$ are independently of one another hydrogen, fluorine, chlorine, a methoxy group, $R^3$ is hydrogen, fluorine, chlorine or a methoxy group, $R^4$ is hydrogen or fluorine, $R^5$ is a hydroxyl group, a chlorine atom, —S—$CH_3$, —S—$CH_2$—$CH_3$, —O—$CH_3$, or —O—$CH_2$—$CH_3$ and their salts, solvates or salts of solvates.

In a more preferred embodiment, the compounds for use are in enantiomerically pure form, and their salts, solvates or salts or solvates.

In an even more preferred embodiment, the compound for use is selected from the following list:

5-{[1-(2-Fluoro-4-methoxyphenyl)-3,3,3-trifluoro-2-hydroxy-2-([methylsulfanyl]methyl)propyl]amino}-1H-quinolin-2-one 5-{[2-([Ethylsulfanyl]methyl)-1-(2-fluoro-4-methoxyphenyl)-3,3,3-trifluoro-2-hydroxypropyl]amino}-1H-quinolin-2-one 5-{[1-(2-Chloro-3-fluoro-4-methoxyphenyl)-3,3,3-trifluoro-2-hydroxy-2-([methylsulfanyl]methyl)propyl]amino}-1H-quinolin-2-one 5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one 5-{[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{[3,3,3-trifluoro-2-hydroxy-2-([methoxymethyl)-1-phenylpropyl]amino}-1H-quinolin-1-one 5-{[1-(2-Chloro-3-fluoro-4-methoxyphenyl)-2-(diaminomethyl)-3,3,3-trifluoro-2-hydroxypropyl]amino}-7-fluoro-1H-quinolin-2-one 5-{[1-(4-Chloro-3-fluoro-2-methoxyphenyl)-3,3,3-trifluoro-2-hydroxy-2-(methoxymethyl)propyl]amino}-7-fluoro-1H-quinolin-2-one 5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{[1-(2-Chloro-3-fluoro-4-hydroxyphenyl)-3,3,3-trifluoro-2-hydroxy-2-(hydroxymethyl)propyl]amino}-7-fluoro-1H-quinolin-2-one and their salts, solvates or salts of solvates.

Still more preferred is a compound, in particular enantiomerically pure compound, selected from:

5-{[1-(2-Fluoro-4-methoxyphenyl)-3,3,3-trifluoro-2-hydroxy-2-([methylsulfanyl]methyl)propyl]amino}-1H-quinolin-2-one 5-{[2-([Ethylsulfanyl]methyl)-1-(2-fluoro-4-methoxyphenyl)-3,3,3-trifluoro-2-hydroxypropyl]amino}-1H-quinolin-2-one 5-{[1-(2-Chloro-3-fluoro-4-methoxyphenyl)-3,3,3-trifluoro-2-hydroxy-2-([methylsulfanyl]methyl)propyl]amino}-1H-quinolin-2-one 5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one 5-{[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{[3,3,3-trifluoro-2-hydroxy-2-([methoxymethyl)-1-phenylpropyl]amino}-1H-quinolin-1-one and their salts, solvates or salts of solvates.

Still even more preferred is the use of a compound, in particular in enantiomerially pure form, selected from the following list:

5-{{1S, 2R)[1-(2-Fluoro-4-methoxyphenyl)-3,3,3-trifluoro-2-hydroxy-2-([methylsulfanyl]methyl)propyl]amino}-1H-quinolin-2-one 5-{(1S,2R)[2-([Ethylsulfanyl]methyl)-1-(2-fluoro-4-methoxyphenyl)-3,3,3-trifluoro-2-hydroxypropyl]amino}-1H-quinolin-2-one 5-{(1S,2R)[1-(2-Chloro-3-fluoro-4-methoxyphenyl)-3,3,3-trifluoro-2-hydroxy-2-([methylsulfanyl]methyl)propyl]amino}-1H-quinolin-2-one 5-{(1S,2R)[1-(2-Chloro-3-fluoro-4-methoxyphenyl)-2-([ethylsulfanyl]methyl)-trifluoro-2-hydroxypropyl]amino}-7-fluoro-1H-quinolin-2-one 5-{(1S,2S)[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-((1S,2S)[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-((1S,2S)[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{(1S,2S)[1-(5-Chloro-3-fluoro-2-methoxyphenyl)-3,3,3-trifluoro-2-hydroxy-2-(hydroxymethyl)propyl]amino}-7-fluoro-1H-quinolin-2-one 5-{{1S, 2R)[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{(1S,2S)[3,3,3-trifluoro-2-hydroxy-2-([methoxymethyl)-1-phenylpropyl]amino}-1H-quinolin-1-one 5-{[(1S,2R)[1-(2-Chloro-3-fluoro-4-methoxyphenyl)-2-(diaminomethyl)-3,3,3-trifluoro-2-hydroxypropyl]amino}-7-fluoro-1H-quinolin-2-one 5-{(1S,2S)[1-(2-Chloro-3-fluoro-4-hydroxyphenyl)-3,3,3-trifluoro-2-hydroxy-2-(hydroxymethyl)propyl]amino}-7-fluoro-1H-quinolin-2-one and their salts, solvates or salts of solvates.

Still even more preferred is the use of compounds, in particular in enantiomerically pure form, selected from:

5-{(1S,2R)[1-(2-Fluoro-4-methoxyphenyl)-3,3,3-trifluoro-2-hydroxy-2-([methylsulfanyl]methyl)propyl]amino}-1-quinolin-2-one 5-{(1S,2R)[2-([Ethylsulfanyl]methyl)-1-(2-fluoro-4-methoxyphenyl)-3,3,3-trifluoro-2 hydroxypropyl]amino}-1H-quinolin-2-one 5-{(1S,2R)[1-(2-Chloro-3-fluoro-4-methoxyphenyl)-3,3,3-trifluoro-2-hydroxy-2-([methylsulfanyl]methyl)propyl]amino}-1H-quinolin-2-one 5-{(1S,2R)[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one 5-{(1S,2S)[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-{(1S,2S)[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{(1S,2S)[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{(1S,2S)[1-(5-Chloro-3-fluoro-2-methoxyphenyl)-3,3,3-trifluoro-2-hydroxy-2-hydroxymethyl)propyl]amino}-7-fluoro-1H-quinolin-2-one 5-{(1S,2R)[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{(1S,2S)[3,3,3-trifluoro-2-hydroxy-2-([methoxymethyl)-1-phenylpropyl]amino}-1H-quinolin-1-one and their salts, solvates or salts of solvates.

In yet another embodiment, the use of the compounds of Formula (I) is preferred according to the invention:

(I)

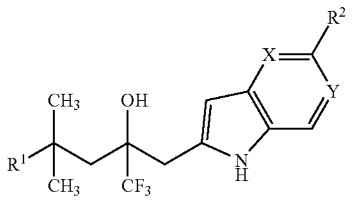

wherein:

$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;

$R^2$ is $C_1$-$C_5$ alkylthio wherein the sulfur atom is optionally oxidized to a sulfoxide or sulfone, optionally independently substituted with one, two, or three substituent groups selected from halogen, hydroxy, oxo, cyano, alkoxyalkyl, and aminocarbonyl;

X is CH or N; and

Y is CH or N, wherein X and Y are not both CH, or a tautomer, optical isomer, prodrug, co-crystal, or pharmaceutically acceptable salt thereof.

Preferred is the use of compounds of Formula (I) wherein:

$R^1$ is an aryl or heteroaryl group, each optionally independently substituted with one, two, or three substituent groups selected from $C_1$-$C_5$alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;

$R^2$ is $C_1$-$C_5$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;

X is CH; and

Y is N, or a tautomer, prodrug, co-crystal, or pharmaceutically acceptable salt thereof.

Preferred is the us of compounds of Formula (I) wherein:

$R^1$ is an aryl group, optionally substituted with one, two, or three substituent groups independently selected from $C_1$, $C_2$, or $C_3$ alkyl, aminocarbonyl, halogen, and $C_1$, $C_2$, or $C_3$ alkylthio wherein the sulfur atom is optionally oxidized to a sulfoxide or sulfone;

$R^2$ is $C_1$, $C_2$, or $C_3$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;

X is CH; and

Y is N, or a tautomer, prodrug, co-crystal, or pharmaceutically acceptable salt thereof.

Preferred is the use of compounds of Formula (I) wherein:

$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;

$R^2$ is $C_1$, $C_2$, or $C_3$ alkylthio wherein the sulfur atom is optionally oxidized to a sulfoxide or sulfone;

X is CH; and

Y is N, or a tautomer, prodrug, co-crystal, or salt thereof.

More preferred is the use of compounds of Formula (I) wherein:

$R^1$ is a phenyl group, optionally substituted with one or two substituent groups independently selected from aminocarbonyl, methyl, fluoro, chloro, bromo, and Ci or $C_2$ alkylthio wherein the sulfur atom is optionally oxidized to a sulfoxide or sulfone;

$R^2$ is Ci or $C_2$ alkylthio wherein the sulfur atom is optionally oxidized to a sulfoxide or sulfone;

X is CH; and

Y is N, or a tautomer, prodrug, co-crystal, or pharmaceutically acceptable salt thereof.

Suitable topical formulations of these compounds for use in the present invention are disclosed in WO 2018/046678 A1. WO 2018/046685 A1 discloses the use of these compounds in the topical treatment of T-cell mediated inflammatory skin diseases such as psoriasis, atopic dermatitis, allergic contact dermatitis.

BI-3047 has the following structure and is an inactive analogue of BI-653048:

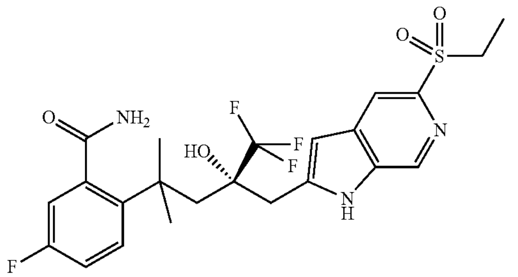 [SMILES: CCS(=O)(=O)c1cc2cc(C[C@@](O)(CC(C)(C)c3ccc(F)cc3C(N)=O)C(F)(F)F)[nH]c2cn1]

BI-3047 is not a SEGRM.

In particular, it was found in the examples that BI-653048 was able to rescue primary human fibroblast cells in monolayer (2D) culture from the growth inhibitory effects of wound exudates of non-healing wounds, as shown in FIG. 1A-1C for WE-1 to WE-3. This effect was dose-dependent with a maximum at 10 μM. In contrast, BI-3047, the inactive analogue of BI-653048, had no proliferation-promoting effect at all concentrations tested. In the absence of WE, both compounds showed similar inhibition of fibroblast growth (FIG. 1D).

In addition, BI-653048, but not BI-3047 reduced the secretion of IL-1β in the fibroblast cultures at the same concentrations which enhanced proliferation in the presence of a WE (FIG. 2).

For the process of wound healing, the production of collagens 1 and 3 by fibroblasts is important. Collagen-1 and -3 mRNA expression is reduced by an aggressive wound exudate (compare e.g. WE and medium in FIGS. 3A and 3C for collagen 1 and 3B and 3D for collagen 3). As depicted in FIGS. 3B, BI-653048, but not BI-3047, induced mRNA expression of both collagens 1 and 3 in the presence of wound exudate. There was no significant effect on collagen 1 mRNA in the presence of medium and a reduction of collagen 3 mRNA with medium for both compounds.

In the fibroblast-derived matrix formation assay (3D fibroblast culture), BI-653048 was effective in inducing matrix formation in the presence of wound exudate, as shown in FIG. 4. This effect could be completely abrogated by the glucocorticoid receptor antagonist mifepristone, indicating that the matrix promoting activity of the SEGRM is mediated by the glucocorticoid receptor.

Mapracorat and related 5-substituted quinolone and isoquinoline derivative compounds, including ZK-216348, as well as their synthesis are disclosed in WO 2006/050998 A1. In particular, the following compounds of formula (IIa) or (IIb) may be used:

(IIa)

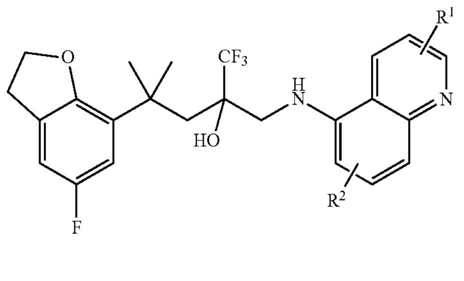

-continued (IIb)

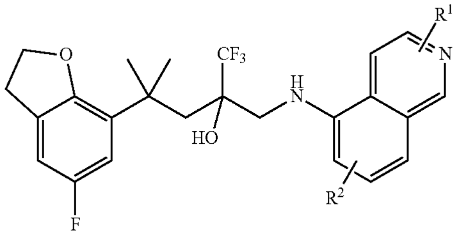

in which

R1 and R2, independently of one another, can be a hydrogen atom, a C1-3-alkyl group, a halogen atom, a cyano group, a C1-3-alkoxy group or a hydroxy group, as well as their racemates or separately present stereoisomers and optionally their pharmaceutically acceptable salts or their prodrugs.

The designation halogen atom or halogen means a fluorine, chlorine, bromine or iodine atom. A fluorine, chlorine or bromine atom is preferred.

The C1-C3-alkyl groups and the C1-C5-alkyl groups can be straight-chain or branched and stand for a methyl, ethyl, n-propyl, iso-propyl, n-butyl, iso-butyl, tert-butyl or n-pentyl, 2,2-dimethylpropyl, 2-methylbutyl or 3-methylbutyl group.

A methyl or ethyl group is preferred.

Radicals R1 and R2 preferably mean hydrogen, C1-3-alkyl, halogen or hydroxy. Especially preferred are hydrogen, methyl, chlorine and hydroxy.

Thus, preferred is the use of 5-substituted quinolone and isoquinoline derivative compounds of general formulas IIa and IIb, in which R1 and R2, independently of one another, preferably mean hydrogen, C1-3-alkyl, halogen or hydroxy.

The use of 5-substituted quinolone and isoquinoline derivative compounds of formulas I and IIb, in which R1 and R2, independently of one another, mean hydrogen, methyl, chlorine or hydroxy, is especially preferred.

More preferred is the use of 5-substituted quinolone and isoquinoline derivative compounds of general formula IIa.

The 5-substituted quinolone and isoquinoline derivative compounds of general formulas (IIa) und (IIb) for use according to the invention can be present as different stereoisomers because of the presence of asymmetry centers. Both the racemates and the separately present stereoisomers belong to the subject of this invention.

The separately present stereoisomers, i.e., (+)-enantiomers and (−)-enantiomers, in particular of Examples 1, 2, 3, 4, 5, 11 and 12 of WO 2006/050998 A1 are particularly preferred for use of the invention.

The compounds for use according to the invention, if they contain a hydroxy group in α-position to the quinolinyl- or isoquinolinyl-nitrogen atom, are also distinguished by the presence of a keto-enol-tautomerism. In terms according to the invention, both forms are part of the subject of the invention, even if, e.g., in the experimental part, only one of the two tautomeric forms has been cited.

In particular, the following SEGRMs can be used according to the invention:

5-[4-(5-Fluoro-2,3-dihydrobenzofuran-7-yl)-2-hydroxy-4-methyl-2-trifluoromethyl-pentylamino]-2-methylquinoline, 5-[4-(5-Fluoro-2,3-dihydrobenzofuran-7-yl)-2-hydroxy-4-methyl-2-trifluoromethyl-pentylamino]-1-methylisoquinoline), 5-[4-(5-Fluoro-2,3-dihydrobenzofuran-7-yl)-2-hydroxy-4-methyl-2-trifluoromethyl-pentylamino]isoquinol-1(2H)-one, 5-[4-(5-Fluoro-2,3-dihydrobenzofuran-7-yl)-2-hydroxy-4-methyl-2-trifluoromethyl-pentylamino]-2,6-dimethylquinoline, 5-[4-(5-Fluoro-2,3-dihydrobenzofuran-7-yl)-2-hydroxy-4-methyl-2-trifluoromethyl-pentylamino]-6-chloro-2-methylquinoline, 5-[4-(5-Fluoro-2,3-dihydrobenzofuran-7-yl)-2-hydroxy-4-methyl-2-trifluoromethyl-pentylamino]isoquinoline, 5-[4-(5-Fluoro-2,3-dihydrobenzofuran-7-yl)-2-hydroxy-4-methyl-2-trifluoromethyl-pentylamino]quinoline, 5-[4-(2,3-Dihydro-5-fluoro-7-benzofuranyl)-2-hydroxy-4-methyl-2-trifluoromethyl-pentylamino]quinolin-2[1H]-one, 6-Fluoro-5-[4-(5-fluoro-2,3-dihydrobenzofuran-7-yl)-2-hydroxy-4-methyl-2-trifluoromethyl-pentylamino]-2-methylquinoline, 8-Fluoro-5-[4-(5-fluoro-2,3-dihydrobenzofuran-7-yl)-2-hydroxy-4-methyl-2-trifluoromethyl-pentylamino]-2-methylquinoline, 5-[4-(5-Fluoro-2,3-dihydrobenzofuran-7-yl)-2-hydroxy-4-methyl-2-trifluoromethyl-pentylamino]-2-methylisoquinol-1(2H)-one, as well as their separate enantiomers:

2(R)-5-[4-(5-Fluoro-2,3-dihydrobenzofuran-7-yl)-2-hydroxy-4-methyl-2-trifluoromethyl-pentylamino]-2-methylquinoline), 2(R)-5-[4-(5-fluoro-2,3-dihydrobenzofuran-7-yl)-2-hydroxy-4-methyl-2-trifluoromethyl-pentylamino]-1-methylisoquinoline, 2(R)-5-[4-(5-Fluoro-2,3-dihydrobenzofuran-7-yl)-2-hydroxy-4-methyl-2-trifluoromethyl-pentylamino]isoquinol-1(2H)-one, 2(R)-5-[4-(5-Fluoro-2,3-dihydrobenzofuran-7-yl)-2-hydroxy-4-methyl-2-trifluoromethyl-pentylamino]-2,6-dimethylquinoline, 2(R)-5-[4-(5-Fluoro-2,3-dihydrobenzofuran-7-yl)-2-hydroxy-4-methyl-2-trifluoromethyl-pentylamino]-6-chloro-2-methylquinoline, 2(R)-5-[4-(5-Fluoro-2,3-dihydrobenzofuran-7-yl)-2-hydroxy-4-methyl-2-trifluoromethyl-pentylamino]isoquinoline, 2(R)-5-[4-(5-Fluoro-2,3-dihydrobenzofuran-7-yl)-2-hydroxy-4-methyl-2-trifluoromethyl-pentylamino]quinoline, 2(R)-5-[4-(2,3-Dihydro-5-fluoro-7-benzofuranyl)-2-hydroxy-4-methyl-2-trifluoromethyl-pentylamino]quinolin-2[1H]-one, 2(R)-6-Fluoro-5-[4-(5-fluoro-2,3-dihydrobenzofuran-7-yl)-2-hydroxy-4-methyl-2-trifluoromethyl-pentylamino]-2-methylquinoline, 2(R)-8-Fluoro-5-[4-(5-fluoro-2,3-dihydrobenzofuran-7-yl)-2-hydroxy-4-methyl-2-trifluoromethyl-pentylamino]-2-methylquinoline, 2(R)-5-[4-(5-Fluoro-2,3-dihydrobenzofuran-7-yl)-2-hydroxy-4-methyl-2-trifluoromethyl-pentylamino]-2-methylquinol-1(2H)-one, 2(S)-5-[4-(5-Fluoro-2,3-dihydrobenzofuran-7-yl)-2-hydroxy-4-methyl-2-trifluoromethyl-pentylamino]-2-methylquinoline), 2(S)-5-[4-(5-Fluoro-2,3-dihydrobenzofuran-7-yl)-2-hydroxy-4-methyl-2-trifluoromethyl-pentylamino]-1-methylisoquinoline), 2(S)-5-[4-(5-Fluoro-2,3-dihydrobenzofuran-7-yl)-2-hydroxy-4-methyl-2-trifluoromethyl-pentylamino]isoquinol-1(2H)-one, 2(S)-5-[4-(5-Fluoro-2,3-dihydrobenzofuran-7-yl)-2-hydroxy-4-methyl-2-trifluoromethyl-pentylamino]-2,6-dimethylquinoline, 2(S)-5-[4-(5-Fluoro-2,3-dihydrobenzofuran-7-yl)-2-hydroxy-4-methyl-2-trifluoromethyl-pentylamino]-6-chloro-2-methylquinoline, 2(S)-5-[4-(5-Fluoro-2,3-dihydrobenzofuran-7-yl)-2-hydroxy-4-methyl-2-trifluoromethyl-pentylamino]isoquinoline, 2(S)-5-[4-(5-Fluoro-2,3-dihydrobenzofuran-7-yl)-2-hydroxy-4-methyl-2-trifluoromethyl-pentylamino]quinoline, 2(S)-5-[4-(2,3-Dihydro-5-fluoro-7-benzofuranyl)-2-hydroxy-4-methyl-2-trifluoromethyl-pentylamino]quinolin-2[1H]-one, 2(S)-6-Fluoro-5-[4-(5-fluoro-2,3-dihydrobenzofuran-7-yl)-2-hydroxy-4-methyl-2-trifluoromethyl-pentylamino]-2-methylquinoline, 2(S)-8-Fluoro-5-[4-(5-fluoro-2,3-dihydrobenzofuran-7-yl)-2-hydroxy-4-methyl-2-trifluoromethyl-pentylamino]-2-methylquinoline, 2(S)-5-[4-(5-Fluoro-2,3-dihydrobenzofuran-7-yl)-2-hydroxy-4-methyl-2-trifluoromethyl-pentylamino]-2-methylisoquinol-1(2H)-one.

Especially preferred is 5-[4-(5-fluoro-2,3-dihydrobenzofuran-7-yl)-2-hydroxy-4-methyl-2-trifluoromethyl-pentylamino]-2-methylquinoline and its separately present enantiomers 2-(R)-5-[4-(5-fluoro-2,3-dihydrobenzofuran-7-yl)-2-hydroxy-4-methyl-2-trifluoromethyl-pentylamino]-2-methylquinoline and 2-(S)-5-[4-(5-fluoro-2,3-dihydrobenzofuran-7-yl)-2-hydroxy-4-methyl-2-trifluoromethyl-pentylamino]-2-methylquinoline.

In an even more preferred embodiment, mapracorat or a pharmaceutically acceptable salt thereof can be used according to the invention. Mapracorat is the INN name of the compound with following formula (I):

(I)

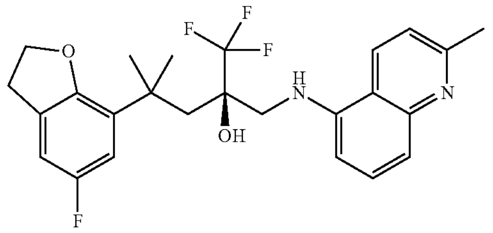

ZK-216348 has the following structure (III)

(III)

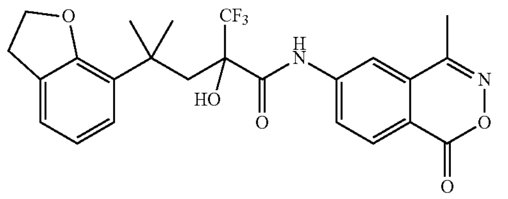

Figure 5:
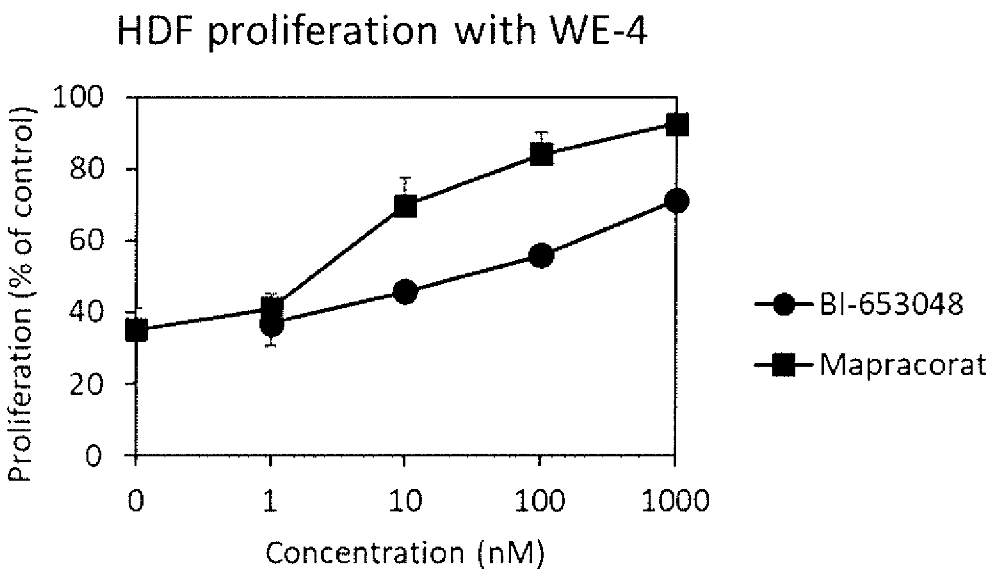

In particular, it was found in the examples that mapracorat enhanced proliferation of fibroblasts in 2D culture in the presence of wound exudate in the same way as BI-653048 (FIG. 5).

Figure 6:
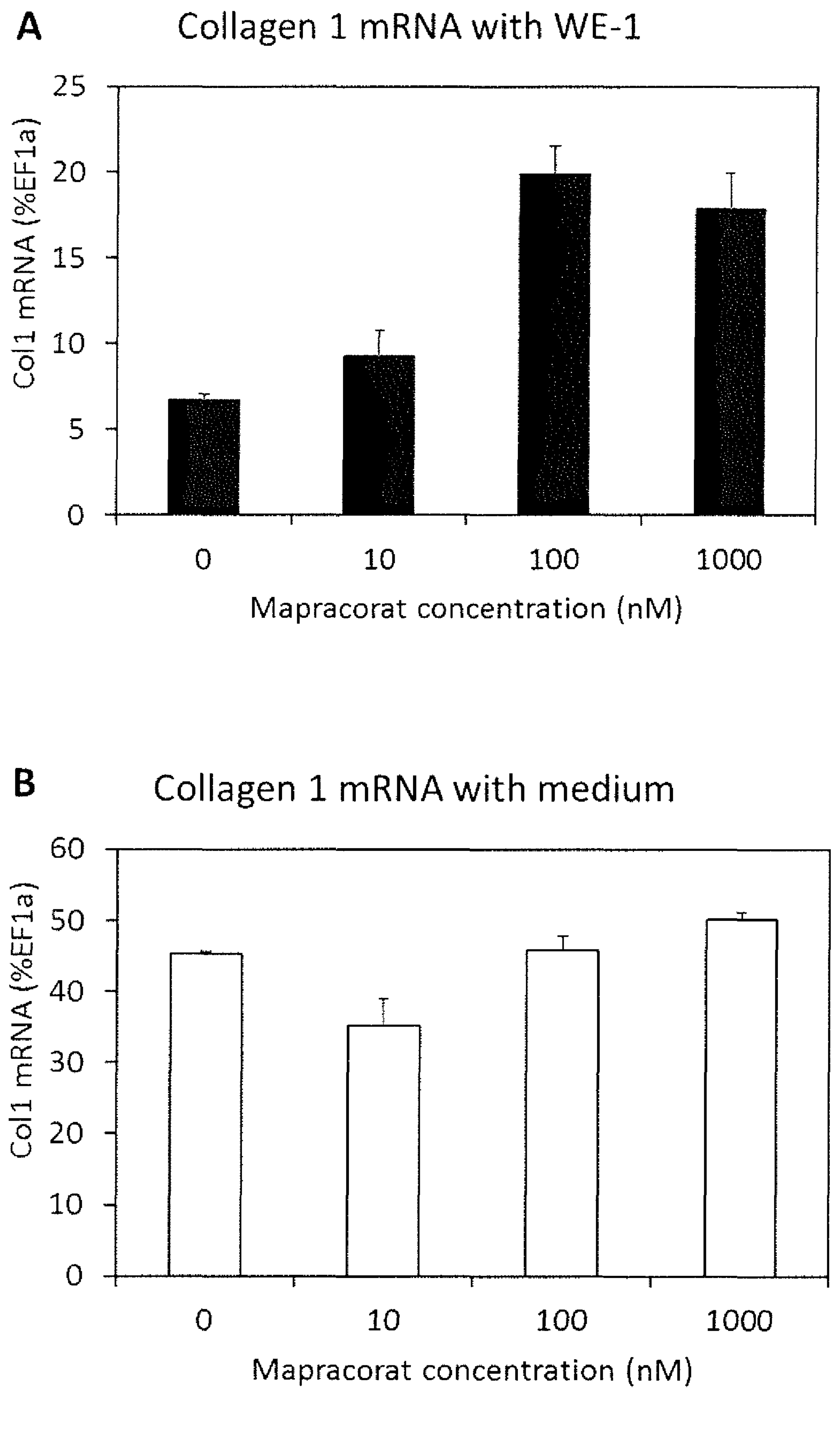
Figure 7:
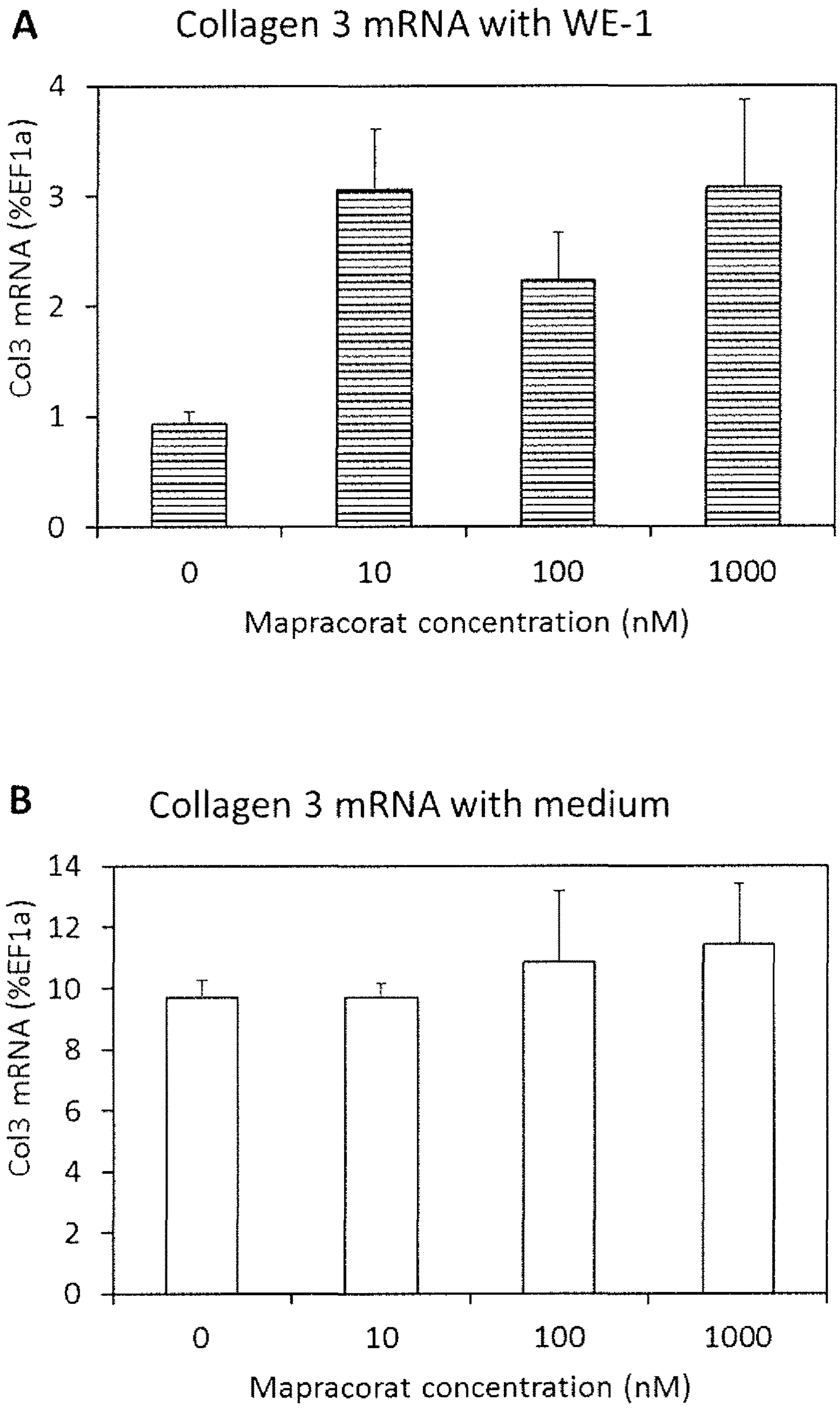

Graded concentrations of mapracorat enhanced mRNA expression of collagen 1 and collagen 3 in 2D fibroblast culture in the presence of wound exudate, but not medium (FIG. 6 and FIG. 7, respectively). Conversely, mapracorat dose-dependently inhibited mRNA expression of IL-1β in these cultures, as shown in FIG. 8A (IL-1β mRNA levels in medium were below the detection limit, FIG. 8B).

Moreover, it was found that mapracorat reduced the wound score from days 6 to 12 in wounds treated with wound exudates from chronic human wounds and the TLR 7/8 agonist R848 as inducers of delayed wound healing in a pig model of delayed wound healing. Mapracorat did not have any negative effect on the healing of control wounds in the presence of human serum.

In particular, it was found in the examples that ZK-216348 and HY14234 were able to rescue fibroblasts in 2D culture from wound-exudate-induced inhibition of proliferation (FIGS. 9A, 10A, and 11A). ZK216348 was less efficient. Both ZK-216348 and HY14234 inhibited wound exudate-induced Il-1β secretion in the fibroblast cultures in the presence of 3 different wound exudates (FIGS. 9B, 10B, and 11B).

In a particularly preferred embodiment, the SEGRM for use of the invention is selected from:

(i) a compound of formula (IIa) or (IIb) below:

(IIa)

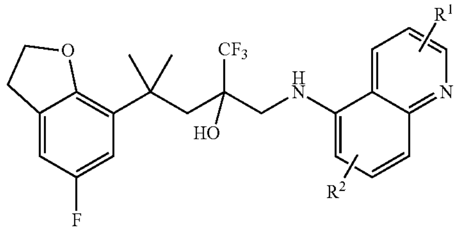

(IIb)

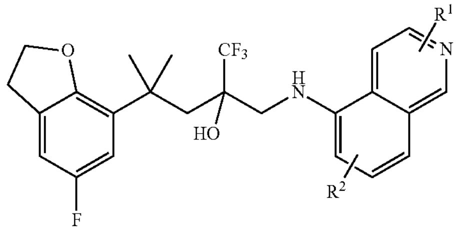

in which $R^1$ and $R^2$, independently of one another, can be a hydrogen atom, a $C_{1-3}$-alkyl group, a halogen atom, a cyano group, a $C_{1-3}$-alkoxy group or a hydroxy group, as well as their racemates or separately present stereoisomers and optionally their pharmaceutically acceptable salts or their prodrugs;

(ii) the compound (R)-2-(4-((5-(Ethylsulfonyl)-1H-pyrrolo[2,3-c]pyridin-2-yl)methyl)-5,5,5-trifluoro-4-hydroxy-2-methylpentan-2-yl)-5-fluorobenzamide, or a pharmaceutically acceptable salt thereof;

(iii) the compound of following formula below:

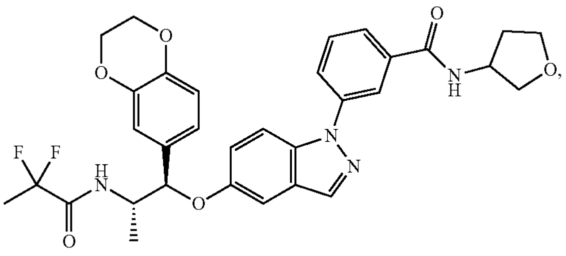 [SMILES: C[C@H](NC(=O)C(C)(F)F)[C@H](Oc1ccc2c(cnn2-c2cccc(C(=O)NC3CCOC3)c2)c1)c1ccc2c(c1)OCCO2]

or a pharmaceutically acceptable salt thereof;

(iv) the compound of following formula below:

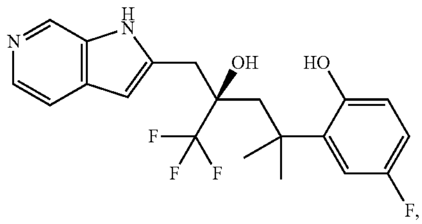

or a pharmaceutically acceptable salt thereof;

(v) a compound of following formula (I) below:

(I)

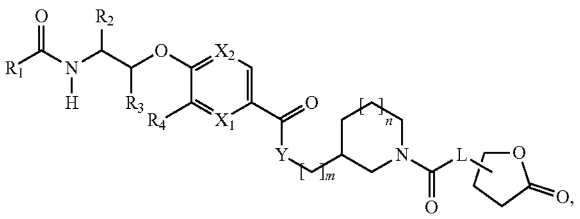

wherein $R_1$ is selected from the group consisting of 5- and 6-membered heteroaryl, $(C_1\text{-}C_6)$alkyl, $(C_3\text{-}C_6)$cycloalkyl, (4-6)-membered heterocycloalkyl and phenyl, wherein said 5- and 6-membered heteroaryl, $(C_1\text{-}C_6)$alkyl, $(C_3\text{-}C_6)$cycloalkyl, (4-6)-membered heterocycloalkyl and phenyl is optionally substituted with one or more substituents independently selected from $(C_1\text{-}C_4)$alkyl, $(C_1\text{-}C_4)$alkoxy, halogen, hydroxyl and cyano;

$R_2$ is selected from $(C_1\text{-}C_3)$alkyl and halo$(C_1\text{-}C_3)$alkyl;

$R_3$ is selected from phenyl, 5-membered heteroaryl and 6-membered heteroaryl, wherein said phenyl, 5-membered heteroaryl and 6-membered heteroaryl are optionally substituted with one or more substituents independently selected from $R_5$;

$R_4$ is selected from hydrogen, halogen, $(C_1\text{-}C_4)$alkyl and halo$(C_1\text{-}C_4)$alkyl;

$R_5$ is selected from halogen, cyano, $(C_1\text{-}C_6)$alkyl, $(C_3\text{-}C_6)$cycloalkyl, $(C_1\text{-}C_6)$alkoxy, halo$(C_1\text{-}C_6)$alkyl, halo$(C_1\text{-}C_6)$alkoxy, hydroxy$(C_1\text{-}C_6)$alkyl, phenyl, 5-membered heteroaryl, 6-membered heteroaryl and $—S(O)_2R_a$, wherein $R_a$ represents $(C_1\text{-}C_4)$alkyl;

$X_1$ is selected from CH, $C(R_b)$ and N, wherein $R_b$ represents halogen, $(C_1\text{-}C_4)$alkyl or halo$(C_1\text{-}C_4)$alkyl;

$X_2$ is selected from CH and N;

Y is selected from —NH— and —O—;

m is 0 or 1; n is 0 or 1;

L represents a bond, —O—, —NH— or $—N(R_c)—$, wherein $R_c$ represents $(C_1\text{-}C_4)$alkyl;

or pharmaceutically acceptable salts, hydrates or solvates thereof;

and (vi) a compound of following formula (III) below:

(III)

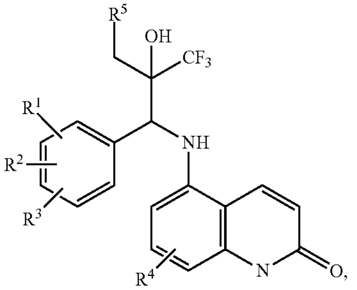

wherein $R^1$ and $R^2$ independently of one another, mean a hydrogen atom, a hydroxy group, a halogen atom, an optionally substituted $(C_1\text{-}C\text{-}_{10})$-alkyl group, an optionally substituted $(C_1\text{-}C\text{-}_{10})$-alkoxy group, a $(C_1\text{-}C_{10})$-alkylthio group, a $(C_1\text{-}C_5)$-perfluoroalkyl group, a cyano group, a nitro group, or $R^1$ and $R^2$ together mean a group that is selected from the groups $—O—(CH_2)_p—O—$, $—O—(CH_2)_p—CH_2—$, —O—CH═CH—, $—(CH_2)_{p+2}—$, $—NH—(CH_2)_{p+1}$, $—N(C_1\text{-}C_3\text{-alkyl})\text{-}(CH_2)_{p+1}$, and —NH—N═CH—, whereby p=1 or 2, and the terminal oxygen atoms and/or carbon atoms and/or nitrogen atoms are linked to directly adjacent ring-carbon atoms, or $NR^6R^7$, whereby $R^6$ and $R^7$, independently of one another, mean hydrogen, $C_1\text{-}C_5$-alkyl or $(CO)—(C_1\text{-}C_5)$-alkyl, $R^3$ means a hydrogen atom, a hydroxy group, a halogen atom, a cyano group, an optionally substituted $(C_1\text{-}C_{10})$-alkyl group, a $(C_1\text{-}C_{10})$-alkoxy group, a $(C_1\text{-}C_{10})$-alkylthio group, or a $(C_1\text{-}C_5)$-perfluoroalkyl group, $R^4$ means a hydrogen, halogen, hydroxy, $(C_1\text{-}C_5)$-alkyl, $(C_1\text{-}C_5)$alkoxy, $(C_1\text{-}C_5)$-alkylthio, $(C_1\text{-}C_5)$-perfluoroalkyl, cyano, nitro, $NR^6R^7$, $COOR^9$, $(CO)NR^6R^7$ or a $(C_1\text{-}C_5\text{-alkylene})\text{-}O—(CO)—(C_1\text{-}C_5)$alkyl group, $R^5$ means a group selected from $—(C_1\text{-}C_{10})$alkyl, which may be optionally partially or completely halogenated, $—(C_2\text{-}C_{10})$alkenyl, $—(C_2\text{-}C_{10})$alkynyl, $(C_3\text{-}C_7)$cycloalkyl-$(C_1\text{-}C_8)$alkyl, $(C_3\text{-}C_7)$cycloalkyl-$(C_1\text{-}C_8)$alkyenyl, $(C_3\text{-}C_7)$cycloalkyl-$(C_2\text{-}C_8)$alkynyl, heterocyclyl-$(C_1\text{-}C_8)$alkyl, heterocyclyl-$(C_1\text{-}C_8)$alkenyl, heterocyclyl-$(C_2\text{-}C_8)$alkynyl, $—R^8$, $R^8$—($C_1$-$C_8$)alkyl,
$R^8$—($C_2$-$C_8$)alkenyl,
$R^8$—($C_2$-$C_8$)alkynyl,
—S—($C_1$-$C_{10}$)-alkyl,
—$SO_2$—($C_1$-$C_{10}$)-alkyl,
—S—$R^8$,
—$SO_2$—$R^8$,
—CN,
-Hal,
—O—($C_1$-$C_{10}$)-alkyl,
—$NR^6R^7$ wherein $R^8$, $R^7$ have the meaning defined above,
—O—$R^8$,
—OH,
with the exception of —$CH(CH_3)_2$) or —$C(CH_3)$=$CH_2$,
$R^8$ means an aryl group which may optionally be substituted by 1-3 hydroxy, halogen, $C_1$-$C_5$-alkyl, $C_1$-$C_5$-alkoxy, cyano, $CF_3$, nitro, COO($C_1$-$C_5$-alkyl) or C(O)$OCH_2$-phenyl or a heteroaryl group
whereby the heteroaryl group may contain 1-3 hetero atoms which may optionally be substituted by 1-3 alkyl groups, hydroxy, halogen, cyano or $C_1$-$C_5$-alkoxy groups, and their salts, solvates or salts of solvates.

In an even more preferred embodiment, the Selective Glucocorticoid Receptor Modulator (SEGRM), or pharmaceutically acceptable salt thereof, for use of the invention is selected from following compounds:

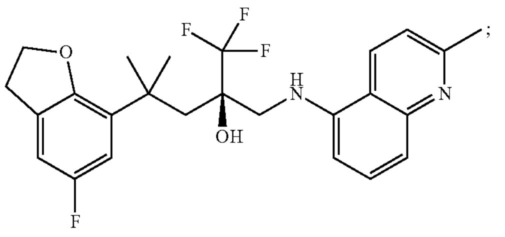

(III)

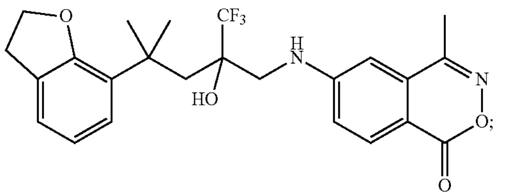

(R)-2-(4-((5-(Ethylsulfonyl)-1H-pyrrolo[2,3-c]pyridin-2-yl)methyl)-5,5,5-trifluoro-4-hydroxy-2-methylpentan-2-yl)-5-fluorobenzamide;

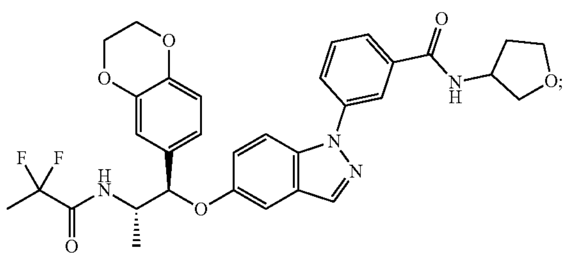

-continued

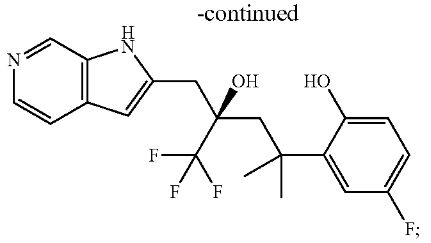

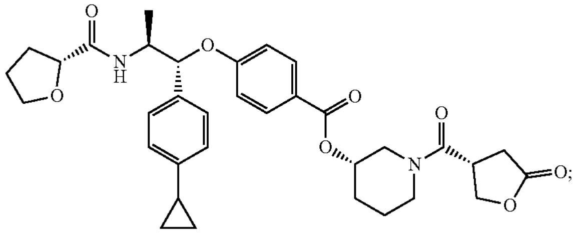

[(3S)-1-[(3R)-5-oxotetrahydrofuran-3-carbonyl]-3-piperidyl]4-[(1R,2S)-1-(4-cyclopropylphenyl)-2-[[(2R)-tetrahydrofuran-2-carbonyl]amino]propoxy]benzoate;
5-{[(1S,2S)-1-(2-chloro-3-fluoro-4-methoxyphenyl)-3,3,3-trifluoro-2-hydroxy-2-(methoxymethyl)propyl]amino}-7-fluoro-1H-quinolin-2-one;
5-{(1S,2S)[1-(2-chloro-3-fluoro-4-methoxyphenyl)-3,3,3-trifluoro-2-hydroxy-2-(hydroxymethyl)propyl]amino}-7-fluoro-1H-quinolin-2-one, and
5-{(1S,2S)[1-(2-chloro-3-fluoro-4-methoxyphenyl)-3,3,3-trifluoro-2-hydroxy-2-(hydroxymethyl)propyl]amino}-7-fluoro-1H-quinolin-2-one,
or a pharmaceutically acceptable salt thereof.

In particular, a plurality of SEGRMs were tested in 3D fibroblast culture with wound exudate from patient #92. The results are shown in FIG. 12. AZD7594 was the most active of the SEGRM tested in 3D culture, followed by mapracorat and BI653048. This is in line with their potencies for glucocorticoid receptor activation ($EC_{50}$ values of 0.9 nM, 1.9 nM and 55 nM, respectively). Moreover, HY-14234 was found to be active. The inactive analogue BI3047 did not induce matrix formation.

The term "pharmaceutically acceptable" is used to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound used in the invention.

Pharmaceutically acceptable acid addition salts can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, betahydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalenesulfonate, 3-phenylpropionate, picrate, pivalate, thiocyanate, tosylate, and undecanoate.

Pharmaceutically acceptable base addition salts include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quarternized with agents such as lower alkyl (C1-C6) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Preferred physiologically acceptable salts of mapracorat include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid. Physiologically acceptable salts of mapracorat also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

The term $C_2$-$C_8$-alkenyl is a straight or branched, substituted or unsubstituted, chain including isomers having an E- or Z-configurated double bond such as e.g. vinyl, propen-1-yl, propen-2-yl (Allyl), but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl. If the alkenyl residue is placed between two other moieties the term alkenyl means alkenylene such as e.g. vinylene, propen-1-ylene, propen-2-ylene (Allylen), but-1-en-1-ylene, but-1-en-2-ylene, but-2-en-1-ylene, but-2-en-2-ylene, 2-methyl-prop-2-en-1-ylene, 2-methyl-prop-1-en-1-ylene, but-1-en-3-ylen, but-3-en-1-ylene.

The term $C_2$-$C_8$-alkynyl stands for a straight or branched chain e,g, $—C≡CH$, $—CH_2—C≡CH$, $—C≡C—CH3$, $—CH(CH_3)—C≡CH$, $—C{=}C—CH_2(CH_3)$, $—C(CH_3)_2—C≡CH$, $—C≡C—CH(CH_3)_{2i}$$—CH(CH_3)—C≡C—CH_3$, $—CH_2—C≡C—CH_2(CH_3)$ or, if the alkynyl residue is placed between two other moieties the term alkynyl means alkynylene such as e.g. $—C≡C—$, $—CH_2—C≡C—$, $—C≡C—CH_2—$, $—CH(CH_3)—C≡V—$, $—C≡C—CH(CH_3)—$, $—C(CH_3)_2—C≡C—$, $—C≡C—C—(CH_3)_2—$, $—CH(CH_3)—C≡C—CH_2—$, $—CH_2—C{=}C—CH(CH_3)—$.

The term $C_3$-C7-cycloalkyl means a substituted or unsubstituted group selected from cyclopropyl, cyclobutyl, cyclopentyl, cyclohexyl, cycloheptyl. The possible substitutents may be selected from hydroxy, halogen, ($C_1$-$C_5$)-alkyl, ($C_1$-$C_5$)-alkoxy, $NR^4R^5$, COO($C_1$-$C_5$)-alkyl, CHO, cyano.

The term $C_3$-$C_7$-cycloalkyl-($C_1C_{10}$)-alkyl- means e.g. $—(CH_2)$-cycloalkyl, $—(C_2H_4)$-cycloalkyl, $—(C_3H_6)$-cycloalkyl, $—(C_4H_8)$-cycloalkyl, $—(C_5H_{10})$-cycloalkyl whereby the cycloylkyl stand for e.g. cyclopropyl, cyclobutyl, cyclopentyl, cyclohexyl, cycloheptyl.

The term $C_3$-$C_7$-cycloalkyl-($C_2$-$C_8$)-alkenyl means e.g. $—(CH{=}CH)$-cycloalkyl, $—[C(CH_3){=}CH]$-cycloalkyl, $—[CH{=}C(CH_3)]$-cycloalkyl, $—(CH{=}CH—CH_2)$-cycloalkyl, $—(CH_2—CH{=}CH)$-cycloalkyl, $—(CH{=}CH—CH_2—CH_2)$-cycloalkyl, $—(CH_2—CH{=}CH—CH_2)$-cycloalkyl, $—(CH_2—CH_2—CH{=}CH)$-cycloalkyl, $—(C(CH_3){=}CH—CH_2)$-cycloalkyl, $—(CH{=}C(CH_3)—CH_2)$-cycloalkyl whereby the term cycloalkyl is defined above.

The term heterocyclyl means e.g. piperidinyl-, morpholinyl-, thiomorpholinyl-, piperazinyl-, tetrahydrofuranyl-, tetrahydrothienyl-, imidazolidinyl- or pyrrolidinyl- whereby the heterocyclyl group may be bound via any possible ring atom. The heterocyclyl group may be substituted by $C_1$-$C_5$-alkyl (optionally substituted), hydroxy-, $C_1$-$C_5$-alkoxy-, $NR^4R^5—$, halogen, cyano-, $COOR^8—$, CHO—. If possible these substituents may also be bound to one of the free nitrogen atoms if any. N-oxides are also included in the definition.

The term heterocyclyl-($C_1$-$C_{10}$)-alkenyl- means an alkylene group as defined above which is connected to the heterocyclyl group which also is already defined above.

The term heterocyclyl-($C_2$-$C_8$)-alkenyl- means an alkylenylene group as defined above which is connected to the heterocyclyl group which also is already defined above.

The term aryl in the sense of the invention means aromatic or partially aromatic carbocyclic rings having 6 to 14 carbon atoms, e.g. phenyl and which may also have a condensed second or third ring such as e.g. napthyl or anthranyl. Further examples are phenyl, naphthyl, tetralinyl, anthranyl, benzoxazinone, dihydroindolone, indanyl, and indenyl. The aryl groups may be substituted at any position leading to a stable molecule by one or several substitutents, e.g. 1-3 substitutents, such as e.g. hydroxy, halogen, $C_1$-$C_5$-alkyl, $C_1$-$C_5$-alkoxy, cyano, $CF_3$, nitro, COO($C_1$-$C_5$-alkyl or benzyl) or a heteroaryl group, preferably by 1-3 $C_1$-$C_5$-alkyl groups, hydroxyl, halogen, cyano or $C_r C_5$-alkoxy.

The term heteroaryl means an aromatic ring system having 1-3 heteroatoms selected from nitrogen, oxygen or sulfur, for five membered rings the maximum number of heteroatoms is three whereby only two oxygen or sulfur atoms are allowed provided that these two are not directly bound to each other.

Possible heteroaryl rings are e.g. thienyl, furanyl, pyrrolyl, oxazolyl, thiazolyl, imidazolyl, pyrazolyl, isoxazolyl, isothiazolyl, oxadiazolyl, triazolyl, thiadiazolyl, benzofuranyl, benzothienyl, benzothiazol, benzoxazolyl, benzimidazolyl, indazolyl, indolyl, isoindolyl, pyridyl, pyridazinyl, pyrimidinyl, pyrazinyl, triazinyl, azaindolizinyl, benzopyridyl, benzopyridazinyl, benzopyrimidinyl, benzopyrazinyl, benzotriazinyl, quinolyl, isoquinolyl, phthalidyl, thiophthalidyl, indolonyl, dihydroindolonyl, isoindolonyl, dihydroisoindolonyl, benzofuranyl or benzimidazolyl.

A SEGRM for use in the invention is administered to a subject in a therapeutically effective amount. For systemic applications, the respective SEGRM dose will be in the range of about 10 to 1000 mg/day, depending on the respective SEGRM. Topical formulations, such as cutaneous or intradermal formulations of SEGRMs may be administered in a concentration of about 0,00001 to 10% (w/v), about 0,00001 to 6% (w/v) or about 0,00001 to 1% (w/v), such as 0,0001 to 0.1% (w/v), such as a cream, gel, lotion, ointment, liposomal or nanoparticulate formulation or the like 0.001 to 1% (w/v). Intradermal formulations may be administered e.g. using microneedles.

For example, a topical formulation of mapracorat may preferably comprise mapracorat at a concentration of >0.01 weight-% to <10, 9, 8, 7, 6, 5, 4, 3, 2 or 1 weight-%, in particular >0.01 weight-% to <5, 4, 3, 2 or 1 weight-%, or >0.05 weight-% to 0.15<weight-% or >0.02 weight % to <0.5 weight-%, or any range of a combination of these values.

For example, the topical formulation disclosed in WO 2018/046678 for the compounds of WO 2009/065503 can be used according to the present invention. The formulations relate to a water-free multi-phase gel system comprising an outer lipid matrix and an inner phase gelled by means of polymer, characterized in that the multi-phase gel system comprises (a) an outer lipid matrix; and (b) comprises an inner phase gelled by at least one polymer, said polymer being selected from the group consisting of cellulose derivatives, acrylate polymers and derivatives thereof or mixtures thereof and the active ingredient is selected from compounds of the general formula (I)

(I)

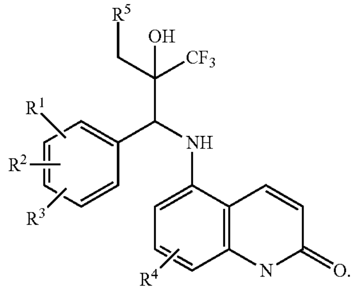

wherein the compound is defined as above.

In particular, such topical formulations are preferred for use in the present invention wherein the active ingredient is selected from the following three compounds:

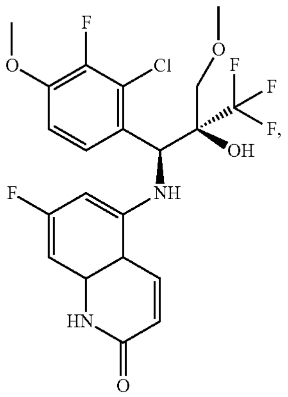

-continued

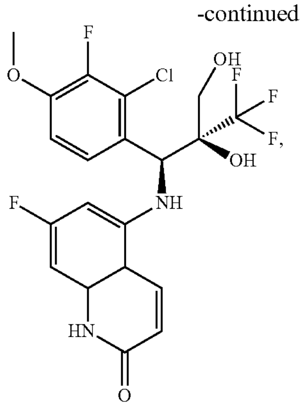

and

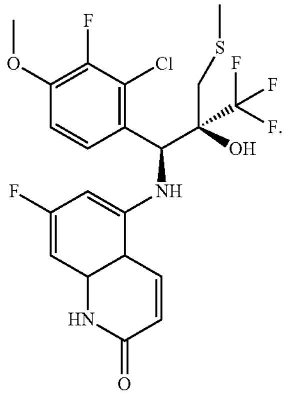

Preferably, the lipid phase contains skin-compatible lipids selected from the group consisting of petrolatum, Paraffin wax, microcrystalline wax, squalene, cetylstearyl octanoate, ethyl oleate, glyceryl tri-caprylate/caprate, myristyl myristate, propylene glycol dicaprate, cetyl esters, isopropyl myristate, isopropyl palmitate, Mono-, di- and triglycerides, ethoxylated glycerides, polyethylene glycol esters, sorbitan esters, hard fat, dibutyladipate, ethyl linoleate, crodamols, isocetylstearate, cetyl palmitates, cetyl alcohol, oley-alcohol, stearyl alcohol, dicaprylylether, oleic acid, waxes, in particular yojoba wax and beeswax, cholesterol, polyethylene glycols, lanolin, lanolin alcohols, silicone oils and mixtures thereof. Preferably, the lipid phase constitutes a proportion of 60 to 95% by weight, more preferably 65 to 92% by weight, more preferably 70 to 90% by weight, of the multi-phase gel system.

Preferably, the the lipid phase contains 50 to 90 wt. %, more preferably 55 to 85 wt. %, more preferably 58 to 80 wt. % petrolatum;

0 to 20 wt. %, more preferably 1 to 15 wt. %, more preferably 5 to 13 wt. % paraffin oil;

0 to 8 wt. %, more preferably 1 to 6 wt. %, more preferably 1 to 4 wt. % beeswax;

0 to 20 wt. %, more preferably 1 to 15 wt. %, more preferably 5 to 13 wt. % hard paraffin; and 0 to 8 wt. %, more preferably 1 to 6 wt. %, more preferably 1 to 4 wt. % cyclomethicone, the weights being based on the multi-phase gel system.

Preferably, the inner gelled phase comprises at least one polymer selected from the group consisting of a cellulose derivative, an acrylate polymer or a derivative thereof or a mixture thereof. Preferably, the inner gelled phase contains a proportion of 5 to 40% by weight, more preferably 8 to 35% by weight, more preferably 10 to 30% by weight, of the multi-phase gel system.

Preferably, a combination of a cross-linked acrylate polymer and hydroxypropyl cellulose is used in the gelled inner phase. Preferably, the inner gelled phase comprises a mixture of a polyol and a carbonic diester. Preferably, the inner gelled phase contains a mixture of propylene glycol and propylene carbonate. Preferably, the inner gelled phase comprises—

0.05 to 0.5% by weight, more preferably 0.075 to 0.4% by weight, more preferably 0.1 to 0.3% by weight, of the crosslinked acrylate polymer;

0.01 to 0.1 wt. %, more preferably 0.01 to 0.08 wt. %, more preferably 0.01 to 0.06 wt. %, of the cellulose derivative, in particular the hydroxypropyl cellulose;

1 to 15 wt. %, more preferably 2 to 13 wt. %, more preferably 3 to 10 wt. %, of the carbonic acid diester, in particular the propylene carbonate; and 0.5 to 20 wt. %, more preferably 0.75 to 17 wt. %, more preferably 1 to 15 wt. %, of polyol, in particular propylene glycol;

the weights always being based on the multiphase gel system.

The invention may be used to treat or prevent different types of skin wounds exhibiting impaired skin wound healing. Different types of skin wounds exhibiting impaired skin wound healing which can be treated in accordance with the present invention include a wound of a diabetic patient, a skin wound which is infected by at least one microorganism, an ischemic wound, a wound in a patient suffering from deficient blood supply or venous stasis, an ulcer, such as a diabetic ulcer, venous ulcer, arterial ulcer, such as ulcus cruris arteriosum, mixed ulcer, or pressure ulcer, a neuropathic wound, ulcus cruris, surgical wound, burn, dehiscence, neoplastic ulcer, a bullous skin disease, such as epidermolysis bullosa, and rare ulcer. Microorganisms infecting skin wounds are known in the art and include bacteria and fungi, such as corynebacteria, staphylococci, streptococci, and yeasts such as candida species.

Therefore, in a preferred embodiment of the present invention, the skin wound is selected from a wound of a diabetic patient, a skin wound which is infected by at least one microorganism, an ischemic wound, a wound in a patient suffering from deficient blood supply or venous stasis, an ulcer, such a diabetic ulcer, venous ulcer, arterial ulcer, such as ulcus cruris arteriosum, mixed ulcer, or pressure ulcer, a neuropathic wound, ulcus cruris, surgical wound, burn, dehiscence, neoplastic ulcer, a bullous skin disease, such as epidermolysis bullosa, and rare ulcer.

The subject or individual may be an otherwise healthy individual or may exhibit further diseases and/or co-morbidities, and/or is treated with medication(s) for further diseases and/or co-morbidities. In a preferred embodiment, the subject or individual, in addition to impaired skin wound healing, exhibits further diseases, and/or co-morbidities, and/or is treated with medication(s) for further diseases and/or co-morbidities.

Therefore, in one preferred embodiment the subject suffers from at least one co-morbidity associated with impaired skin wound healing. Such co-morbidities are for example diabetes, suppressed immune system following transplantation of a graft and graft-versus-host disease (GvHD). Further co-morbidities include adipositas, increased blood pressure, venous stasis or peripheral arterial occlusion. Further co-morbidities are diseases treatable with glucocorticoids.

A co-morbidity is understood as the presence of one or more additional diseases or disorders co-occurring with a given disease.

Therefore, in another preferred embodiment of the present invention, the subject has undergone transplantation of a graft, and/or obtains immunosuppressive therapy, and/or is treated with at least one immunosuppressive drug. For example, immunosuppressive therapy is by administering a glucocorticoid and/or a calcineurin inhibitor. Accordingly, the immunosuppressive drug may be selected from a glucocorticoid and a calcineurin inhibitor. Suitable calcineurin inhibitors are known in the art and include tacrolimus, pimecrolimus and cyclosporin A. Suitable glucocorticoids are known in the art and include cortisol, cortisone acetate, prednisone, prednisolone, methylprednisolone, chloroprednisone, cloprednol, difluprednate, fludrocortisone acetate, fluocinolone, fluperolone, fluprednisolone, loteprednol, prednicarbate, tixocortol, triamcinolone, triamcinolone acetonide, dexamethasone, betamethasone, beclometasone, deoxycorticosterone acetate, alclometasone, clobetasol, clobetasone, clocortolone, desoximetasone, diflorasone, difluocortolone, fluclorolone, flumetasone, fluocortin, fluocortolone, fluprednidene, fluticasone, fluticasone furoate, halometasone, meprednisone, mometasone, mometasone furoate, paramethasone, prednylidene, rimexolone, ulobetasol, amcinonide, budesonide, ciclesonide, deflazacort, desonide, formocortal, fluclorolone acetonide, fludroxycortide, flunisolide, fluocinolone acetonide, fluocinonide, halcinonide, hydroxymethylprogesterone, and medroxyprogesterone, or a pharmaceutically acceptable salt thereof.

The present invention relates to SEGRMs, or pharmaceutically acceptable salts thereof, for the prevention and/or treatment of impaired skin wound healing in a subject.

A "skin wound" is understood as a damage to a skin of a living individual, such as cuts, tears, burns, or breaks. Preferably, a skin wound is understood as open injury of the skin of a living individual. The skin may be located at any area of an individual, such as for example the head, the arms, the legs, the chest, or the back. Further, the individual may have one, two, three, four or more skin wounds. Further, the area of a skin wound may differ. In a preferred embodiment, the skin wound forms wound exudate. In another preferred embodiment, the skin wound forms a wound biofilm.

"Impaired skin wound healing" refers to a skin wound which does not heal at an expected rate. In a preferred embodiment, the impaired skin wound healing is a non-healing skin wound or chronic skin wound. A non-healing skin wound is preferably understood as a skin wound which does not close within 2 months under standard therapy, preferably within 3 or more months under standard therapy. Preferably, a non-healing skin wound is characterized by a lack of wound closure, an increase of the area and/or depth of the wound, necrosis and/or infections of the skin wound, and/or lack of granulation.

As used herein, a "healing skin wound" is understood as a skin wound which heals at an expected rate, in particular, as a skin wound which closes within 2 months under standard therapy. Preferably, a healing skin wound is characterized by ongoing wound closure, granulation, absence of necrosis and/or absence of infections.

An "ulcer" is understood as a sore on the skin, accompanied by the disintegration of tissue. Ulcers can result in complete loss of the epidermis and often portions of the dermis and even subcutaneous fat.

The "subject" or "individual" is an animal, preferably the individual is a vertebrate, in particular a mammal, more preferably a human.

In another preferred embodiment of the present invention, the subject suffers from diabetes and/or has at least one diabetic ulcer.

The skin wound of the subject may already receive a treatment such as a standard therapy for treating wound healing, or may be untreated regarding the skin wound.

"Standard therapy" is understood as a treatment recommended in general by physicians for skin wounds, in particular one or more selected from wound dressings, surgical and biological (maggot) debridement, infection control, negative pressure therapy, and therapy with a biological or cell treatment.

Therefore, in one preferred embodiment the skin wound of the subject may be untreated or treated with standard therapy for treating wound healing or with one or more of the following for treating wound healing: compression, wound dressings, surgical debridement, biological debridement, infection control, antibiotic therapy, negative pressure therapy, proteins, in particular protein growth factors, antibodies, peptides, sugars, cells or cell constituents, artificial skin, human blood-derived products, gene therapy or genetically engineered wound bed modifications, drugs, herbal medicines, or plant extracts. In one preferred embodiment, the skin wound of the subject may be untreated or treated with standard therapy for treating wound healing wherein the standard therapy does not include treatment with protein growth factors. In another preferred embodiment, the skin wound of the subject may be untreated or treated with standard therapy for treating wound healing wherein the standard therapy includes treatment with protein growth factors.

Therefore, in another preferred embodiment of the present invention, the subject suffers from diabetes and/or has at least one diabetic ulcer, and/or the subject (i) has undergone transplantation of a graft, and optionally suffers from diabetes, and/or (ii) obtains immunosuppressive therapy, and optionally suffers from diabetes.

Further, it was surprisingly found in the examples that both an assay based on fibroblast proliferation as well as an assay based on fibroblast-derived matrix formation allows for the identification of subjects suffering from impaired skin wound healing which are responsive to a treatment and/or prevention with a SEGRM. Moreover, it was found that the secretion of the IL-1 cytokine IL-1beta is a sensitive and predictive marker. Accordingly, determining an IL-1 is in a preferred embodiment used in combination with an assay based on fibroblast proliferation and/or an assay based on fibroblast-derived matrix formation.

The assays may be used for successful stratification and identification of subjects suffering from impaired skin wound healing. Accordingly, the assays are useful for personalized medicine approaches.

Therefore, in yet another preferred embodiment of the present invention, the subject is identified to be responsive to the treatment of impaired skin wound healing by performing steps i) and/or ii):

- i) measuring the proliferation of fibroblast cells, and optionally the amount of at least one IL-1 cytokine marker in the supernatant of fibroblast cells, in the presence of:
  - (1) a wound exudate sample or wound biofilm sample obtained from the skin wound of said subject, and
  - (2) at least one Selective Glucocorticoid Receptor Modulator (SEGRM), or pharmaceutically acceptable salt thereof;
- ii) measuring the fibroblast-derived matrix formation by fibroblast cells in the presence of:
  - (1) a wound exudate sample or wound biofilm sample obtained from the skin wound of said subject, and
  - (2) at least one Selective Glucocorticoid Receptor Modulator (SEGRM), or pharmaceutically acceptable salt thereof.

In a more preferred embodiment, the subject is identified to be responsive to the treatment of impaired skin wound healing with a Selective Glucocorticoid Receptor Modulator (SEGRM), or pharmaceutically acceptable salt thereof, In case the value of proliferation of fibroblast cells measured in step i) and/or the value of the fibroblast-derived matrix formation by fibroblast cells measured in step ii) is at least 20% above a control value established in the absence of the at least one Selective Glucocorticoid Receptor Modulator (SEGRM), or pharmaceutically acceptable salt thereof of (2), and, optionally, in case the value for the amount of the at least one IL-1 cytokine marker in the supernatant of fibroblast cells obtained in step i) is below a control value established in the absence of the at least one Selective Glucocorticoid Receptor Modulator (SEGRM), or pharmaceutically acceptable salt thereof of (2).

In one preferred embodiment of the present invention, the sample is a wound exudate sample. In another preferred embodiment, the sample is a wound biofilm sample. In a more preferred embodiment, the sample is a wound exudate sample.

The SEGRM to be administered to the subject in case the subject is identified to be responsive may be the same SEGRM(s) or different SEGRM(s), preferably the same SEGRM(s).

Measuring the proliferation of fibroblast cells in the presence of a wound exudate sample, or wound biofilm sample, obtained from said skin wound and the SEGRMs of (2) may be performed as shown in the examples. The assay is also referred to as "HDF proliferation", "human dermal fibroblast proliferation", "fibroblast proliferation" or "2D fibroblast proliferation" assay in the present application. For the assay, fibroblast cells are used, which may be primary fibroblast cells, such as primary mammal dermal fibroblasts, or cells of a fibroblast cell line, preferably primary fibroblast cells. Methods for culturing fibroblast cells are known in the art and are for example described in the examples. For example, the cells may be cultured using DMEM medium containing FCS.

In a further preferred embodiment, the cells are incubated on a solid support, thereby allowing the cells to adhere to the support, as for example described in the Examples, where multiwell plates were used. Further, the cells are contacted with the wound exudate sample, or wound biofilm sample, which is optionally diluted, e.g. diluted with medium or a saline aqueous liquid, and the SEGRMs of (2). The contacting may be performed before or after adherence of the cells occurs. For example, the contacting may be achieved by adding the optionally diluted, liquid wound exudate sample, or wound biofilm sample, and the SEGRMs of (2) to the cells either prior to adherence, for example at the seeding of the cells, or after adherence. The contacting may be achieved e.g. by pipetting, and optionally gentle mixing. The cells are incubated for an appropriate time, such as for 6 hours to 300 hours, more preferably 12 hours to 200 hours, even more preferably 24 hours to 120 hours. In the examples, 72 hours were successfully used. For negative control samples, a corresponding liquid in the absence of the SEGRMs of (2) may be added in addition to wound exudate, or wound biofilm, or only wound exudate, or wound biofilm, is added. Subsequently, the amount, preferably the cell number, including the formation of extracellular matrix, of the fibroblast cells is determined, such as by fixing cells and determining total protein content. The cells may for example be fixed using paraformaldehyde. Further, a suitable dye, such as sulforhodamine B may be used for determining the amount, preferably the cell number, including the formation of extracellular matrix, of the fibroblast cells. The stained cells including the extracellular matrix formed may then be quantified e.g. by determining absorbance or fluorescence at a suitable wavelength, depending on the dye. Preferably, the steps are performed in 2D cell culture, which allows for culturing the cells adherently on a solid support. Preferably, the sample is a wound exudate sample.

Therefore, in another preferred embodiment, the method step includes the following steps:

(i) culturing fibroblast cells,
(ii) incubating the cells on a solid support, thereby allowing the cells to adhere to the support,
(iii) contacting the cells with (1) the wound exudate sample, or wound biofilm sample, which is optionally diluted, and the SEGRMs of (2), wherein the contacting may be performed before or after adherence of the cells occurs, and wherein the contacting of (1) and (2) may be performed simultaneously or sequentially, and
(iv) determining the amount, preferably the cell number, including the formation of extracellular matrix, of the fibroblast cells, such as by fixing cells and determining total protein content, preferably wherein the method is performed in 2D cell culture.

In one preferred embodiment of the present invention, the sample is a wound exudate sample. In another preferred embodiment, the sample is a wound biofilm sample. In a more preferred embodiment, the sample is a wound exudate sample.

Optionally, the amount of at least one IL-1 cytokine marker in the supernatant of fibroblast cells in i) is measured.

It was found in the Examples that an IL-1 cytokine, in particular IL-1beta, is a sensitive marker in the context of the present invention.

"IL-1 cytokine" is understood to encompass IL-1alpha and IL-1beta. In a preferred embodiment, the IL-1 cytokine is IL-1beta.

The amounts of the pro-inflammatory IL-1 cytokines secreted by fibroblasts were found to be particularly predictive for identifying healing skin wounds or non-healing skin wounds as well as for monitoring wound healing. In particular, higher amounts of these cytokines were found to be secreted in the presence of WE from non-healing wounds as compared to WE from healing wounds. Cytokines IL1alpha and IL-1beta are proteins, preferably human proteins, which are well-known to a skilled person. IL-1alpha (also known as Interleukin-1$\alpha$ or IL-1$\alpha$) and IL-1beta (also known as Interleukin-1$\beta$ or IL-1$\beta$) may be determined by methods known in the art, e.g. by using an immunological assay, even more preferably by using an ELISA assay, as described in the Examples, or by determining IL-1 cytokine mRNA, as described in the Examples. IL-1alpha and IL-1beta are known to be pro-inflammatory cytokines.

Therefore, in a preferred embodiment, the subject is identified to be responsive to the treatment of impaired skin wound healing by performing step i) measuring the proliferation of fibroblast cells, and optionally the amount of at least one IL-1 cytokine marker in the supernatant of fibroblast cells.

Preferably, the measuring of the amount of at least one IL-1 cytokine marker in the supernatant of fibroblast cells in i) includes the following steps:

(i) culturing fibroblast cells,
(ii) incubating the cells on a solid support, thereby allowing the cells to adhere to the support,
(iii) contacting the cells with (1) the wound exudate sample, or wound biofilm sample, which is optionally diluted, and the SEGRMs of (2), wherein the contacting may be performed before or after adherence of the cells occurs, and wherein the contacting of (1) and (2) may be performed simultaneously or sequentially, and
(iv) determining the amount of at least one IL-1 cytokine marker in the cell culture supernatant, preferably wherein the at least one IL-1 cytokine marker is determined by using an immunological assay, more preferably by using an ELISA assay, and/or by determining IL-1 cytokine mRNA, wherein the method is performed in 2D cell culture.

In one preferred embodiment of the present invention, the sample is a wound exudate sample. In another preferred embodiment, the sample is a wound biofilm sample. In a more preferred embodiment, the sample is a wound exudate sample.

The culturing of cells is preferably performed at about 20° C. to 40° C., more preferably 25° C. to 38° C., even more preferably at about 37° C.

Measuring the fibroblast-derived matrix formation by fibroblast cells in the presence of a wound exudate sample, or wound biofilm sample, obtained from a skin wound may be performed as shown in the examples. The assay is also referred to as "ECM formation", "fibroblast-derived matrix", or "3D fibroblast derived matrix" assay in the present application. For the assay, fibroblast cells are used, which may be primary fibroblast cells, such as primary mammal dermal fibroblasts, or cells of a fibroblast cell line, preferably primary fibroblast cells. In the examples, fibroblast cells are seeded on a support, which is preferably pre-coated with an adhesion enhancing agent, such as gelatin. For example, the coating may be achieved by incubating the support with a solution or suspension containing the adhesion enhancing agent, such as gelatin. In the examples, a 0.2% gelatin solution was successfully used. Preferably, the cells are cultured until confluence is reached. Subsequently, the cells are contacted with (i) a matrix promoting supplement, (ii) the wound exudate sample, or wound biofilm sample, which is optionally diluted, and (iii) the SEGRMs of (2), wherein (i), (ii) and (ii) may be contacted simultaneously or sequentially. For example, the matrix promoting supplement, which is preferably selected from a solution comprising Vitamin C or a physiologically acceptable salt thereof, such as the sodium salt, or 2-phospho-L-ascorbic acid or a physiologically acceptable salt thereof, and a combination of EGF and insulin, is added to the cells, e.g. by pipetting, and optionally gentle mixing. The wound exudate sample, or wound biofilm sample, which is optionally diluted, may be contacted simultaneously or sequentially and the SEGRMs of (2) are added simultaneously or sequentially. For example, the optionally diluted wound exudate sample, or wound biofilm sample, may be mixed with the matrix promoting supplement, and the mixture may be added to the cells, and the SEGRMs of (2) are added subsequently. Alternatively, the optionally diluted wound exudate sample, or wound biofilm sample, may be added separately, but simultaneously, or separately, but subsequent to or prior to the matrix promoting supplement and/or the SEGRMs of (2). In case of subsequent non-simultaneous contacting, the components (i), (ii) and (iii) are preferably contacted within 1 hour. The cells are subsequently incubated, preferably for 12 hours to 20 days, wherein the medium is optionally replaced at least one time with fresh medium supplemented with optionally diluted wound exudate, or wound biofilm, and matrix promoting supplement. In the example, the medium was replaced once after 4 days of incubation. As a 3-dimensional fibroblast-derived matrix is formed, the solid support preferably contains at least one cavity which allows for filling of the space and therefore allows for a 3D cell culture. Subsequently, the amount of the fibroblast-derived matrix is determined, such as by fixing cells and determining total protein content. The cells may for example be fixed using paraformaldehyde. Further, a suitable dye, such as sulforhodamine B may be used for determining the amount, preferably the cell number, including the formation of extracellular matrix, of the fibroblast cells. The stained cells including the formation of extracellular matrix may then be quantified e.g. by determining absorbance or fluorescence at a suitable wavelength, depending on the dye. For negative control samples, a corresponding liquid in the absence of the SEGRMs of (2) may be added in addition to wound exudate, or wound biofilm, or only wound exudate, or wound biofilm, is added. Preferably, the sample is a wound exudate sample.

Accordingly, the method step preferably includes the following steps:

(i) seeding fibroblast cells on a support, which is preferably pre-coated with an adhesion enhancing agent, such as gelatin,
(ii) culturing the cells on the support, preferably until confluence is reached,
(iii) contacting the cells with (i) a matrix promoting supplement, (ii) the wound exudate sample, or wound biofilm sample, which is optionally diluted, and (iii) the SEGRMs of (2), wherein (i) and (ii) may be contacted simultaneously or sequentially,
(iv) determining the amount of the fibroblast-derived matrix, such as by fixing cells and determining total protein content, preferably wherein the method is performed in 3D cell culture.

In one preferred embodiment of the present invention, the sample is a wound exudate sample. In another preferred embodiment, the sample is a wound biofilm sample. In a more preferred embodiment, the sample is a wound exudate sample.

The "fibroblast-derived matrix" or "FDM" is understood as the extracellular matrix (ECM) formed by living fibroblast cells in an environment conducive for matrix formation, e.g. in the presence of a matrix promoting supplement. FDM is obtainable as described in the examples. In particular, FDM is obtainable by (i) seeding fibroblast cells on a support, which is pre-coated with an adhesion enhancing agent, such as gelatin, (ii) culturing the cells on the support, preferably until confluence is reached and (iii) contacting the cells with a matrix promoting supplement, such as Vitamin C or a physiologically acceptable salt thereof, or 2-phospho-L-ascorbic acid or a physiologically acceptable salt thereof, or a combination of EGF and insulin.

A "matrix promoting supplement" is understood as a compound or composition which promotes the formation of fibroblast-derived matrix by living fibroblast cells in an in vitro cell culture. Suitable matrix promoting supplements are Vitamin C or a physiologically acceptable salt thereof, such the sodium salt, or 2-phospho-L-ascorbic acid or a physiologically acceptable salt thereof, and a combination of EGF and insulin, as well as compositions comprising the compounds, such as solutions or suspensions. A combination of EGF and insulin may be provided to the cell culture separately, e.g. as separate solutions comprising EGF or insulin respectively, or together, e.g. as solution comprising EGF and insulin.

An "adhesion enhancing agent" is an agent which enhances adhesion of cells to a solid support, such as a plastic support, but which does not substantially interfere with the viability of the cells. In a preferred embodiment, the adhesion enhancing agent is gelatin or fibronectin, more preferably gelatin.

"2D cell culture" is understood as a cell culture wherein the cells are cultured in a planar or substantially planar surface. In a preferred embodiment, the 2D cell culture is culturing of adherent cells.

"3D cell culture" is understood as a cell culture wherein the cells are cultured on a non-planar or substantially non-planar surface. In a preferred embodiment, the 3D cell culture is culturing of adherent cells and/or culturing of cells within a matrix, such as ECM, in particular FDM.

A "support" or "solid support" is preferably selected from a chip, array, such as a microarray or nanoarray, a plate, such as a multiwell plate, or a dish. For cell culture applications, the solid support is preferably suitable for culturing cells, for example the support may be a plastic support.

"Wound exudate" is understood as the extracellular fluid located within and above a skin wound. The wound exudate is also referred to as a "liquid biopsy".

"Wound biofilm" is understood as substance, resulting from an infection of a skin wound by micro-organisms that are capable of forming colonies. Typically, the wound biofilm is a gummy or gum-like substance. A wound biofilm comprises microbial species selected from bacteria, fungi, yeasts, algae and other micro-organisms, and cellular debris. A wound biofilm is formed when certain types of micro-organisms attach themselves to the surface of skin wounds by secreting a gummy or gum-like substance. For example, a wound biofilm sample may be obtained by surgical sharp debridement of the wound surface or by wiping of the wound surface with a swab, such as a cotton swab or nylon-flocked swab, or wound dressing material.

A "wound exudate sample" or "WE" is understood as a sample of wound exudate obtained from a skin wound of an individual. Methods for obtaining a wound exudate sample are known in the art. For example, a wound exudate sample may be obtained by a physical or chemical method, in particular by applying negative pressure to the skin wound, such as by using a negative pressure drainage device, a method using capillary forces, collecting wound exudate in a film dressing or membrane, collecting wound exudate in a syringe, applying an absorptive material, such as absorptive beads, or a filter, or by using a swab, such as a cotton swab or nylon-flocked swab, in particular wherein the film dressing or membrane is a cellulose layer and/or wherein the absorptive material is a cellulose layer. Preferred suitable cellulose layers are nanocellulose layers. The volume of wound exudate sample may vary and may be in the range of 1 nl to 1 l, 10 nl to 1 l, or 100 nl to 1 l, such as 1 μl to 1 l, 1 ml to 1 l or 10 ml to 1 l. For example, wound exudate samples investigated in the examples had a volume of up to 400 ml and typically had a volume of 0.1 to 100 ml, in particular 1 to 50 ml. The wound exudate sample may be used for the methods of the invention directly after obtaining the sample or may be stored, in particular stored at <4° C., <0° C. or <10° C., such as about −20° C. or −80° C., before usage in the methods of the invention.

A "wound biofilm sample" or "WB" is understood as a sample of wound biofilm obtained from a skin wound of an individual. Methods for obtaining a wound biofilm sample are known in the art. For example, a wound biofilm sample may be obtained by surgical sharp debridement or by wiping of the wound surface with a swab, such as a cotton swab or nylon-flocked swab, or wound dressing material. The volume of wound biofilm sample may vary and may be in the range of 1 nl to 1 l, 10 nl to 1 l, or 100 nl to 1 l, such as 1 μl to 10 ml, 1 μl to 1 ml or 10 μl to 1 ml. The wet weight of wound biofilm may vary and may be in the range of 10 μg to 10 g, 100 μg to 10 g, such as 1 mg to 10 g, 10 mg to 10 g, 100 mg to 10 g, or 1 g to 10 g. The wound biofilm sample may be used for the methods of the invention directly after obtaining the sample or may be stored, in particular stored at <4° C., <0° C. or <10° C. before usage in the methods of the invention. The wound biofilm sample can be extracted with a suitable liquid, such as cell culture medium or buffer, in particular with liquid of 5 to 10 times of the weight of the sample.

It was surprisingly found that the above assays relating to measuring the proliferation of fibroblast cells and the fibroblast-derived matrix formation by fibroblast cells can reliably identify subjects responsive to a treatment and/or prevention of impaired skin wound healing of any of the above embodiments of the invention.

Moreover, it was found that the accuracy of the identification of responsive subjects is improved in case of both measuring the proliferation of fibroblast cells, and optionally measuring the amount of at least one IL-1 cytokine. Accordingly, in a more preferred embodiment, the subject is identified to be responsive to the treatment of impaired skin wound healing in case the value of proliferation of fibroblast cells measured in step i) and the value of the fibroblast-derived matrix formation by fibroblast cells measured in step ii) is at least 20% above a control value established in the absence of the SEGRMs of (2), and, optionally, in case the value for the amount of the at least one IL-1 cytokine marker in the supernatant of fibroblast cells obtained in step i) is below a control value established in the absence of the at least one Selective Glucocorticoid Receptor Modulator (SEGRM), or pharmaceutically acceptable salt thereof of (2).

Accordingly, in a yet further preferred embodiment, the subject is identified to be responsive to the treatment of impaired skin wound healing in case the value of proliferation of fibroblast cells measured in step i) and/or the value of the fibroblast-derived matrix formation by fibroblast cells measured in step ii) is at least 30%, 40%, 50%, 60%, 70%, 80%, 100% or more above a control value established in the absence of the SEGRMs of (2), and, optionally, in case the value for the amount of the at least one IL-1 cytokine marker in the supernatant of fibroblast cells obtained in step i) is below a control value established in the absence of the at least one Selective Glucocorticoid Receptor Modulator (SEGRM), or pharmaceutically acceptable salt thereof of (2).

Accordingly, in a yet further preferred embodiment, the subject is identified to be responsive to the treatment of impaired skin wound healing in case the value of proliferation of fibroblast cells measured in step i) and/or the value of the fibroblast-derived matrix formation by fibroblast cells measured in step ii) is at least 30%, 40%, 50%, 60%, 70%, 80%, 100% or more above a control value established in the absence of the SEGRMs of (2), and, optionally, in case the value for the amount of the at least one IL-1 cytokine marker in the supernatant of fibroblast cells obtained in step i) is at least 5%, 10%, 15%, 20%, 30%, 40%, 50% or more below a control value established in the absence of the at least one Selective Glucocorticoid Receptor Modulator (SEGRM), or pharmaceutically acceptable salt thereof of (2).

The control value(s) may be determined in parallel or may be established independently, preferably in parallel.

Moreover, the accuracy and reliability can be further increased by including one or more additional assays which determine macrophage M1 and M2 markers and/or cytokine markers IL1alpha, IL1beta and/or TNFalpha in macrophage/fibroblast co-culture in the context of wound exudate, or wound biofilm, obtained from the respective subject. These M1 and M2 markers may be cell surface protein markers, protein markers in the supernatant of macrophages or marker mRNAs in macrophages.

Macrophages are tissue-resident professional phagocytes and antigen-presenting cells (APC), which differentiate from circulating peripheral blood monocytes. Activated macrophages of different phenotypes are classified by skilled persons into M1-macrophages and M2 macrophages. M1-macrophages are activated macrophages which comprise immune effector cells with an acute inflammatory phenotype. These are highly aggressive against bacteria and produce large amounts of cytokines. The M2-macrophages are alternatively activated and anti-inflammatory.

A "M2 marker" is understood as a protein marker which is specific for M2 macrophages. Preferably, the marker is secreted by the macrophages. Suitable M2 markers are known in the art and are preferably selected from CCL22 and CCL18. The markers may be determined by methods known in the art, e.g. by using an immunological assay, even more preferably by using an ELISA assay.

A "M1 marker" is understood as a protein marker which is specific for M1 macrophages. Preferably, the marker is secreted by the macrophages. Suitable M1 markers are known in the art and are preferably selected from CXCL10 and IL-23p19. The markers may be determined by methods known in the art, e.g. by using an immunological assay, even more preferably by using an ELISA assay.

A "M1 cell surface marker" is understood as a protein marker which is expressed at the surface of macrophages, and which is specific for M1 macrophages. Suitable M1 cell surface markers are known in the art and are preferably selected from CD38, CD64 and CD197. The amount(s) and/or frequency distribution(s) of the cell surface markers may be determined by an immunological assay and/or a fluorescence assay, in particular by FACS analysis, whereby typically a frequency distribution is determined.

A "M2 cell surface marker" is understood as a protein marker which is expressed at the surface of macrophages, and which is specific for M2 macrophages. Suitable M2 cell surface markers are known in the art and are preferably selected from CD200 receptor (CD200R), CD206 and CD209. The amount(s) and/or frequency distribution(s) of the cell surface markers may be determined by an immunological assay and/or a fluorescence assay, in particular by FACS analysis, whereby typically a frequency distribution is determined.

A "M2 marker mRNA" is understood as an mRNA which is expressed by macrophages, and which is specific for M2 macrophages. Suitable M2 marker mRNAs are known in the art and are preferably selected from CD200 receptor (CD200R), CD206, CD209, CCL22 and CCL18. The marker mRNAs may be determined by methods known in the art. Preferably, the amount may be determined by contacting a probe which specifically binds to a marker mRNA, wherein the probe is optionally labelled, with the macrophage RNA under conditions which are conducive to hybridization, and detecting the hybridized probe. For example, the mRNA may be reversely transcribed into cDNA prior to detection.

A "M1 marker mRNA" is understood as an mRNA which is expressed by macrophages, and which is specific for M1 macrophages. Suitable M1 marker mRNAs are known in the art and are preferably selected from CD38, CD64, CD197, CXCL10 and IL-23p19. Preferably, the amount may be determined by contacting a probe which specifically binds to a marker mRNA, wherein the probe is optionally labelled, with the macrophage RNA under conditions which are conducive to hybridization, and detecting the hybridized probe. For example, the mRNA may be reversely transcribed into cDNA prior to detection.

The ratio of M1/M2 markers is indicative of a responsive subject, in combination with one or more cellular assays described above relating to measuring the proliferation of fibroblast cells, measuring the fibroblast-derived matrix (FDM) formation by fibroblast cells and measuring the proliferation of keratinocyte cells. In particular, an elevated ratio of M1/M2 markers, M1/M2 cell surface markers or M1/M2 marker mRNAs is indicative of a non-responsive subject, whereas a low ratio of M1/M2 markers, M1/M2 cell surface markers or M1/M2 marker mRNAs is indicative of a responsive subject.

Moreover, the amounts of the pro-inflammatory cytokines IL1alpha, IL1beta and TNF-alpha secreted by macrophages and/or fibroblasts in a macrophage/fibroblast co-culture were found to be particularly predictive for identifying healing skin wounds or non-healing skin wounds as well as for monitoring wound healing. In particular, higher amounts of these cytokines were found to be secreted in the presence of WE from non-healing wounds as compared to WE from healing wounds. Cytokines IL1alpha, IL1beta and TNF-alpha are proteins, preferably human proteins, which are well-known to a skilled person. IL1alpha (also known as Interleukin-1α or IL-1α), IL1beta (also known as Interleukin-1β or IL-1β) and TNF-alpha (also known as Tumor Necrosis Factor α or TNF-α) may be determined by methods known in the art, e.g. by using an immunological assay, even more preferably by using an ELISA assay, as described in the Examples, or by determining IL1alpha, IL1beta or TNF-alpha mRNA expression. IL1alpha, IL1beta and TNF-alpha are known to be pro-inflammatory cytokines.

Therefore, in a more preferred embodiment of the present invention, in addition, step iiia) and/or one, two, three or four of the following steps iiib) to iiie) are performed:

- iiia) measuring the proliferation of keratinocyte cells in the presence of:
  - (1) a wound exudate sample, or wound biofilm sample, obtained from the skin wound of said subject, and
  - (2) at least one Selective Glucocorticoid Receptor Modulator (SEGRM), or pharmaceutically acceptable salt thereof,
- iiib) measuring the amount(s) of one or more M1 marker(s) and one or more M2 marker(s) in the supernatant of macrophages incubated with
  - (1) a wound exudate sample or wound biofilm sample obtained from said skin wound, and
  - (2) at least one Selective Glucocorticoid Receptor Modulator (SEGRM), or pharmaceutically acceptable salt thereof,
  - wherein the macrophages are in co-culture with fibroblasts, and
  - wherein the one or more M1 markers are selected from CXCL10 and IL-23p19, and the one or more M2 markers are selected from CCL22 and CCL18,
- iiic) measuring the amount(s) and/or frequency distribution(s) of one or more M1 cell surface marker(s) and one or more M2 cell surface marker(s) on macrophages incubated with
  - (1) a wound exudate sample or wound biofilm sample obtained from said skin wound, and
  - (2) at least one Selective Glucocorticoid Receptor Modulator (SEGRM), or pharmaceutically acceptable salt thereof,
  - wherein the macrophages are in co-culture with fibroblasts, and
  - wherein the one or more M1 cell surface markers are selected from CD38, CD64 and CD197, and wherein the one or more M2 cell surface markers are selected from CD200 receptor, CD206 and CD209,
- iiid) measuring the expression level(s) of one or more M1 marker mRNA(s) and one or more M2 marker mRNA(s) in macrophages incubated with
  - (1) a wound exudate sample or wound biofilm sample obtained from said skin wound, and
  - (2) at least one Selective Glucocorticoid Receptor Modulator (SEGRM), or pharmaceutically acceptable salt thereof,
  - wherein the macrophages are in co-culture with fibroblasts, and
  - wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18,
- iiie) measuring the amount(s) of one or more cytokine markers in the supernatant of macrophages incubated
  - (1) with a wound exudate sample or wound biofilm sample obtained from said skin wound, and
  - (2) at least one Selective Glucocorticoid Receptor Modulator (SEGRM), or pharmaceutically acceptable salt thereof,
  - wherein the macrophages are in co-culture with fibroblasts, and
  - wherein the one or more cytokine markers are selected from IL-1alpha, IL-1beta and TNF-alpha, and wherein the subject is identified to be responsive to the treatment with a least one Selective Glucocorticoid Receptor Modulator (SEGRM), or pharmaceutically acceptable salt thereof, in case the value of proliferation of fibroblast cells measured in step i) and/or the value of the fibroblast-derived matrix formation by fibroblast cells measured in step ii) and/or the value of the proliferation of keratinocyte cells in step iiia) is at least 20% above a control value established in the absence of the at least one Selective Glucocorticoid Receptor Modulator (SEGRM), or pharmaceutically acceptable salt thereof of (2), and, optionally, in case the value for the amount of the at least one IL-1 cytokine marker in the supernatant of fibroblast cells obtained in step i) is below a control value established in the absence of the at least one Selective Glucocorticoid Receptor Modulator (SEGRM), or pharmaceutically acceptable salt thereof of (2), and/or in case one or more of the following applies:

- the ratio of amount(s) of one or more M1 marker(s) to the amount(s) of one or more M2 marker(s) obtained in iiib) is/are below a control value established in the absence of the at least one Selective Glucocorticoid Receptor Modulator (SEGRM), or pharmaceutically acceptable salt thereof of (2), the ratio of amount(s) and/or frequency distribution(s) of one or more M1 cell surface marker(s) to the amount(s) and/or frequency distribution(s) of one or more M2 cell surface marker(s) obtained in iiic) is/are below a control value established in the absence of the at least one Selective Glucocorticoid Receptor Modulator (SEGRM), or pharmaceutically acceptable salt thereof of (2), in particular wherein the ratio is selected from a CD38/CD209 ratio, a CD197/CD209 ratio and a CD197/CD206 ratio, the ratio of expression level(s) of one or more M1 marker mRNA(s) to the expression level(s) of one or more M2 marker mRNA(s) obtained in iiid) is/are below a control value established in the absence of the at least one Selective Glucocorticoid Receptor Modulator (SEGRM), or pharmaceutically acceptable salt thereof of (2), the value obtained in iiie) is below a control value established in the absence of the at least one Selective Glucocorticoid Receptor Modulator (SEGRM), or pharmaceutically acceptable salt thereof of (2)

Preferably, the subject is identified to be responsive to the treatment with the SEGRM(s) of (2), in case the value of proliferation of fibroblast cells measured in step i) and/or the value of the fibroblast-derived matrix formation by fibroblast cells measured in step ii) and/or the value of the proliferation of keratinocyte cells in step iiia) is at least 20% above a control value established in the absence of the at least one Selective Glucocorticoid Receptor Modulator (SEGRM), or pharmaceutically acceptable salt thereof of (2), and, optionally, in case the value for the amount of the at least one IL-1 cytokine marker in the supernatant of fibroblast cells obtained in step i) is below, such as at least 5%, 10%, 15%, 20%, 30%, 40%, 50% or more below, a control value established in the absence of the at least one Selective Glucocorticoid Receptor Modulator (SEGRM), or pharmaceutically acceptable salt thereof of (2), and/or in case the following applies:

the value obtained in iiie) is below, such as at least 5%, 10%, 15%, 20%, 30%, 40%, 50% or more below, a control value established in the absence of the at least one Selective Glucocorticoid Receptor Modulator (SEGRM), or pharmaceutically acceptable salt thereof of (2).

In a more preferred embodiment, the cytokine marker in iiie) is selected from IL-1alpha and IL-1beta, even ore preferably the cytokine marker in iiie) is IL-1beta.

It was found that the following M1 cell surface marker/M2 cell surface marker ratios are also predictive for responsiveness: a CD38/CD209 ratio, a CD197/CD209 ratio or a CD197/CD206 ratio below a control value established in the absence of the SEGRM(s) of (2) is identifying a patient to be responsive to the treatment with the SEGRM(s).

Therefore, in another preferred embodiment, the ratio of amount(s) and/or frequency distribution(s) is selected from a CD38/CD209 ratio, a CD197/CD209 ratio and a CD197/CD206 ratio.

The frequency distribution may be determined by determining the % age of cells which are positive for a given marker within a population, which is the most commonly used readout in FACS analysis. Alternatively, the amount may be determined by determining the quantity of cell surface expression, as a surrogate for the number of labelled molecules on the cell surface per individual cell when using labelled binding agents for the markers, as for example measured by the mean fluorescence intensity.

In a preferred embodiment, measuring the amount(s) of one or more M1 marker(s) and one or more M2 marker(s) in the supernatant of macrophages incubated with a wound exudate sample or wound biofilm sample obtained from a skin wound includes the following steps:

(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample, or wound biofilm sample, which is optionally diluted, and the SEGRMs of (2), and
(iv) determining the amount of one or more M1 markers and one or more M2 markers in the cell culture supernatant, preferably wherein the one or more M1 markers are selected from CXCL10 and IL-23p19, and/or the one or more M2 markers are selected from CCL22 and CCL18, more preferably wherein the markers are determined by using an immunological assay, even more preferably by using an ELISA assay.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample, or wound biofilm sample, which is optionally diluted, for example by pipetting the sample to the cells, and the SEGRMs of (2), and optionally gentle mixing. The compounds are added after macrophages have differentiated; e.g. after 4 to 7 days. Further, the cells are incubated, preferably for 1 hour to 100 hours. Subsequently, the amount of one or more M1 markers and one or more M2 markers in the cell culture supernatant is determined. The supernatant is typically harvested for such purpose and the markers are determined using a suitable assay, such as immunological assay. For example, an ELISA may be used.

In another preferred embodiment, measuring the amount(s) and/or frequency distribution(s) of one or more M1 cell surface marker(s) and one or more M2 cell surface marker(s) on macrophages incubated with a wound exudate sample or wound biofilm sample obtained from a skin wound includes the following steps:

(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample, or wound biofilm sample, which is optionally diluted, and the SEGRMs of (2)
(iv) determining the amount(s) and/or frequency distribution(s) of one or more M1 cell surface marker(s) and one or more M2 cell surface marker(s) on the cell surface of macrophages.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample, or wound biofilm sample, which is optionally diluted, for example by pipetting the sample to the cells, and the SEGRMs of (2), and optionally gentle mixing. The compounds are added after macrophages have differentiated; e.g. after 4 to 7 days. Further, the cells are incubated, preferably for 1 hour 100 hours. Subsequently, the amount(s) and/or frequency distribution(s) of one or more M1 cell surface marker(s) and one or more M2 cell surface marker(s) on the cell surface of macrophages is/are determined. For example, the cells may be harvested and subjected to FACS analysis, gating on the monocyte/macrophage population. Geometric means of mean fluorescence intensities can be used to quantify surface marker expression.

Preferably, the one or more M1 cell surface markers are selected from CD38, CD64 and CD197, and/or the one or more M2 cell surface markers are selected from CD200 receptor (CD200R), CD206 and CD209, more preferably wherein the amount(s) and/or frequency distribution(s) of the cell surface markers are determined by an immunological assay and/or a fluorescence assay, in particular by FACS analysis.

It was found that the following M1 cell surface marker/M2 cell surface marker ratios are also predictive for determining responsiveness: a CD38/CD209 ratio, a CD197/CD209 ratio and a CD197/CD206 ratio. A CD38/CD209 ratio, a CD197/CD209 ratio or a CD197/CD206 ratio below a control value established in the absence of the SEGRMs of (2) is identifying a patient to be responsive to the treatment with the SEGRMs.

Therefore, in another preferred embodiment, the ratio of amount(s) and/or frequency distribution(s) is selected from a CD38/CD209 ratio, a CD197/CD209 ratio and a CD197/CD206 ratio.

Accordingly, in another preferred embodiment, the one or more M1 cell surface marker is selected from CD38 and the one or more M2 cell surface marker is selected from CD209, or the one or more M1 cell surface marker is selected from CD197 and the one or more M2 cell surface marker is selected from CD209 and CD206.

In one preferred embodiment, step (iv) comprises contacting the macrophages with binding agents, preferably antibodies, which specifically recognize one or more M1 surface marker(s) and one or more M2 surface marker(s), wherein the binding agents are optionally labelled, in particular labelled with a fluorescent label, and determining the amount of binding molecules bound to the macrophages, in particular by determining mean fluorescence intensity, thereby determining the amount(s) of the cell surface markers. For example, antibodies specifically recognizing the surface markers and which contain a fluorescent label may be used.

In another preferred embodiment, step (iv) comprises contacting the macrophages with binding agents, preferably antibodies, which specifically recognize one or more M1 surface marker(s) and one or more M2 surface marker(s), wherein the binding agents are optionally labelled, in particular labelled with a fluorescent label, and determining the percentages of cells which are positive for the one or more M1 surface marker(s) and the one or more M2 surface marker(s), respectively, within a cell population, in particular wherein FACS analysis is performed, thereby determining the frequency distribution(s) of the cell surface markers. For example, antibodies specifically binding to the surface markers and which contain a fluorescent label may be used.

Determination of proteins as binding agents of a marker protein can be performed using any of a number of known methods for identifying and obtaining proteins that specifically interact with proteins or polypeptides, for example, a yeast two-hybrid screening system. A binding agent which specifically recognizes a marker has preferably at least an affinity of $10^7$ l/mol for its corresponding target molecule. The binding agent which specifically recognizes a marker preferably has an affinity of $10^8$ l/mol or even more preferred of $10^9$ l/mol for its target marker molecule. As the skilled person will appreciate, the term specific is used to indicate that other biomolecules present in the sample do not significantly bind to the binding agent which specifically recognizes the marker. Preferably, the level of binding to a biomolecule other than the target marker molecule results in a binding affinity which is only 10% or less, more preferably only 5% or less of the affinity to the target marker molecule, respectively. A preferred specific binding agent will fulfill both the above minimum criteria for affinity as well as for specificity.

A binding agent which specifically recognizes a marker preferably is an antibody reactive with the marker. The term antibody refers to a polyclonal antibody, a monoclonal antibody, antigen binding fragments of such antibodies, single chain antibodies as well as to genetic constructs comprising the binding domain of an antibody. The term "antibodies" includes polyclonal antibodies, monoclonal antibodies, fragments thereof such as F(ab')2, and Fab fragments, as well as any naturally occurring or recombinantly produced binding partners, which are molecules that specifically bind to a marker protein. Any antibody fragment retaining the above criteria of a specific binding agent can be used.

For measurement, the sample obtained from an individual is incubated with the binding agent that specifically recognizes the marker in question under conditions appropriate for formation of a binding agent marker-complex. Such conditions need not be specified, since the skilled artisan without any inventive effort can easily identify such appropriate incubation conditions. The amount of binding agent marker-complex is measured and used in the methods and uses of the invention. As the skilled artisan will appreciate there are numerous methods to measure the amount of the specific binding agent marker-complex all described in detail in relevant textbooks (cf., e.g., Tijssen P., supra, or Diamandis, E. P. and Christopoulos, T. K. (eds.), Immunoassay, Academic Press, Boston (1996)).

Particularly, monoclonal antibodies to the marker(s) are used in a quantitative (amount or concentration of the marker(s) is determined) immunoassay.

For example, the marker may be detected in a sandwich type assay format. In such assay a first specific binding agent is used to capture the marker in question on the one side and a second specific binding agent (e.g. a second antibody), which is labeled to be directly or indirectly detectable, is used on the other side. The second specific binding agent may contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of binding agent remaining on the support after wash. The amount of the second binding agent that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques. Spectroscopic methods can be used to detect dyes (including, for example, colorimetric products of enzyme reactions), luminescent groups and fluorescent groups. Biotin can be detected using avidin or streptavidin, coupled to a different reporter group, commonly a radioactive or fluorescent group or an enzyme. Enzyme reporter groups can generally be detected by the addition of substrate, generally for a specific period of time, followed by spectroscopic, spectrophotometric or other analysis of the reaction products. Standards and standard additions can be used to determine the level of antigen in a sample, using well known techniques.

Immunoassays for measuring marker proteins of the invention include for example ELISA, enzyme immunoassay (EIA) and electro-chemiluminescence immunoassay (ECLIA) for the quantitative determination of a marker protein described herein.

In another preferred embodiment, measuring the expression level(s) of one or more M1 marker mRNA(s) and one or more M2 marker mRNA(s) in macrophages incubated with a wound exudate sample or wound biofilm sample obtained from a skin wound includes the following steps:

(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample, or wound biofilm sample, which is optionally diluted, and the SEGRMs of (2), and
(iv) determining the expression level(s) of one or more M1 marker mRNA(s) and one or more M2 marker mRNA(s) in the macrophages.

In one preferred embodiment of the present invention, the sample is a wound exudate sample. In another preferred embodiment, the sample is a wound biofilm sample. In a more preferred embodiment, the sample is a wound exudate sample.

Preferably, the one or more M1 marker mRNA(s) are selected from CD38, CD64, CD197, CXCL10 and IL-23p19, and/or the one or more M2 marker mRNA(s) are selected from CD200 receptor (CD200R), CD206, CD209, CCL22 and CCL18, more wherein the method comprises contacting a probe which specifically binds to a marker mRNA, wherein the probe is optionally labelled, with the macrophage RNA under conditions which are conducive to hybridization, and detecting the hybridized probe.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample, or wound biofilm sample, which is optionally diluted, for example by pipetting the sample to the cells, and the SEGRMs of (2), and optionally gentle mixing. The compounds are added after macrophages have differentiated; e.g. after 4 to 7 days. Further, the cells are incubated, preferably for 1 hour 100 hours. Subsequently, the expression level(s) of one or more M1 marker mRNA(s) and one or more M2 marker mRNA(s) in the macrophages is determined. For example, the cells may be harvested and mRNA expression level(s) may be determined using suitable probes. For example, the expression level of a housekeeping gene such as actin or GAPDH may be determined and the expression level(s) of M1 or M2 marker RNA(s) may be determined as expression level relative to a housekeeping gene.

In another preferred embodiment, measuring the amount(s) of one or more cytokine markers selected from IL-1alpha, IL-1beta and TNF-alpha in the supernatant of macrophages incubated with a wound exudate sample or wound biofilm sample obtained from a skin wound includes the following steps:

(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted, and the SEGRMs of (2), and
(iv) determining the amount of one or more cytokine markers selected from IL-1alpha, IL-1beta and TNF-alpha in the cell culture supernatant, preferably wherein the cytokine markers are determined by using an immunological assay, more preferably by using an ELISA assay.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample or wound biofilm sample, which is optionally diluted, and the SEGRMs of (2), wherein the contacting may be performed for example by pipetting the sample to the cells, and optionally gentle mixing. The compounds are added after macrophages have differentiated; e.g. after 4 to 7 days. Further, the cells are incubated, preferably for 1 hour to 100 hours. Subsequently, the amount of one or more of IL-1alpha, IL-1beta and TNF-alpha in the cell culture supernatant is determined. The supernatant is typically harvested for such purpose and the cytokine markers are determined using a suitable assay, such as immunological assay. For example, an ELISA may be used. In a preferred embodiment, the sample is a wound exudate sample.

The amounts of IL-1alpha, IL-1beta and TNF-alpha in the supernatant of macrophages are indicative for a patient responsive to the treatment with the compound(s) of (2).

Accordingly, a patient is identified to be responsive to the treatment with the compound(s) of (2) in case the value obtained for the amounts of IL-1alpha, IL-1beta and TNF-alpha is below a control value established in the absence of the compound(s) of (2).

A SEGRM for therapeutic or preventive use of the prevention or as comprised in a kit or kit-of-parts of the invention is preferably in a pharmaceutical composition. The pharmaceutical compositions contain the respective active agent(s), and optionally one or more pharmaceutically acceptable excipients and/or pharmaceutically acceptable excipients. The active agent is a SEGRM or a pharmaceutically acceptable salt thereof.

A "pharmaceutically acceptable carrier" means a carrier or diluent that does not cause significant irritation to an organism and does not abrogate the biological activity and properties of the administered active agent. The carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

In one preferred embodiment of any of the above aspects of the invention, a SEGRM is formulated for systemic, preferably oral or intravenous administration, or is formulated for local administration, in particular for topical, mucosal, ocular, intradermal or subcutaneous administration. For example, topical formulations for administration of mapracorat or a pharmaceutically acceptable salt thereof are known in the art and are described in detail in U.S. Pat. No. 8,282,909. Moreover, the skilled person is aware of techniques for providing further formulations for local administration, in particular for topical, mucosal, ocular, intradermal or subcutaneous administration. For example, a SEGRM or a pharmaceutically acceptable salt thereof may be formulated as being incorporated into a wound dressing or bandage, or as gel, semi-solid gel, cream, lotion, ointment, spray, foam, dispersion, salve, liposomal or nanoparticulate formulation or for application by microneedles.

Therefore, in yet a further preferred embodiment of the present invention, the Selective Glucocorticoid Receptor Modulator (SEGRM), or pharmaceutically acceptable salt thereof is (i) formulated for systemic, preferably oral or intravenous administration, or
(ii) formulated for local administration, in particular for topical, mucosal, ocular, intradermal or subcutaneous administration.

In one more preferred embodiment of the present invention, the SEGRM or the pharmaceutically acceptable salt thereof for use of the present invention is formulated for local administration, in particular for topical, mucosal, ocular, intradermal or subcutaneous administration.

Topical formulations for administration of mapracorat or a pharmaceutically acceptable salt thereof and related SEGRMs are known in the art and are described in detail in U.S. Pat. No. 8,282,909. Such Formulations comprise at least one Selective Glucocorticoid Receptor Modulator (SEGRM) and a) oleyl alcohol, b) cetearyl octanoate and c) a vegetable oil. In a more preferred embodiment, the SEGRM is a SEGRM as disclosed in U.S. Pat. No. 8,282,909, in particular mapracorat or a pharmaceutically acceptable salt thereof.

Therefore, in yet a further preferred embodiment of the present invention, the Selective Glucocorticoid Receptor Modulator (SEGRM), or pharmaceutically acceptable salt thereof is formulated for local administration, wherein said pharmaceutical formulation comprises at least one Selective Glucocorticoid Receptor Modulator (SEGRM) and a) oleyl alcohol, b) cetearyl octanoate and c) a vegetable oil.

In more preferred embodiments, the pharmaceutical formulation comprises at least one Selective Glucocorticoid Receptor Modulator (SEGRM) and a) 2 to 50% by weight of oleyl alcohol, b) 2 to 50% by weight of cetearyl octanoate and c) 2 to 50% by weight of a vegetable oil, preferably wherein:

the vegetable oil is soybean oil, olive oil, sesame oil, castor oil or peanut oil, or the pharmaceutical formulation further contains d) propylene glycol and e) glycerol, or the pharmaceutical formulation contains 3 to 15% (by weight) of oleyl alcohol, or the pharmaceutical formulation contains 2 to 15% (by weight) of cetearyl octanoate the pharmaceutical formulation contains which contains 3 to 15% (by weight) of vegetable oil, or the pharmaceutical formulation contains further contains a medium-chained triglyceride, mineral oil, cyclomethicone, stearyl alcohol, butylated hydroxytoluene, macrogolglycerolhydroxystearate, povidone, acrylic acid copolymer, hydroxyethylcellulose, acrylic acid, and/or trometamol, or the pharmaceutical formulation contains further containing d) silicon dioxide, or the pharmaceutical formulation further contains d) aluminium stearate, the pharmaceutical formulation further contains d) propylene glycol, e) glycerol, and f) propellant, the pharmaceutical formulation contains 2 to 10% (by weight) of propellant, or the propellant is a hydrocarbon or hydrofluoroalkane, or the solubility of at least one pharmaceutically active compound in water is 20 mg/l at 20° C. or less, or the pharmaceutical formulation contains 2 to 50% (by weight) of oleyl alcohol, 3 to 20% (by weight) of cetearyl octanoate, and 5 to 20% (by weight) of vegetable oil, or the pharmaceutical formulation contains contains 3 to 15% (by weight) of oleyl alcohol, 2 to 15% (by weight) of cetearyl octanoate, 3 to 15% (by weight) of vegetable oil, or the pharmaceutical formulation contains further contains a medium-chained triglyceride, mineral oil, cyclomethicone, stearyl alcohol, butylated hydroxytoluene, macrogolglycerolhydroxystearate, povidone, acrylic acid copolymer, hydroxyethylcellulose, acrylic acid, and/or trometamol, or the pharmaceutical formulation contains further contains silicon dioxide and aluminium stearate, or the pharmaceutical formulation contains 6 to 8% (by weight) of propellant, preferably wherein the propellant is propane, butane, isobutene, heptafluoropropane, tetrafluoroethane, dimethylether, or a mixture thereof.

In other preferred embodiments, the pharmaceutical formulation comprises at least one Selective Glucocorticoid Receptor Modulator (SEGRM) and a) 2 to 50% by weight of oleyl alcohol, b) 2 to 50% by weight of cetearyl octanoate and c) 2 to 50% by weight of a vegetable oil, more preferably wherein:

the pharmaceutical formulation further contains d) propylene glycol and e) glycerol, or the pharmaceutical formulation contains 3 to 15% (by weight) of oleyl alcohol, 2 to 15% (by weight) of cetearyl octanoate, 3 to 15% (by weight) of vegetable oil, or the pharmaceutical formulation further contains a medium-chained triglyceride, mineral oil, cyclomethicone, stearyl alcohol, butylated hydroxytoluene, macrogolglycerolhydroxystearate, povidone, acrylic acid copolymer, hydroxyethylcellulose, acrylic acid, and/or trometamol, or the pharmaceutical formulation further contains silicon dioxide or aluminium stearate, or the pharmaceutical formulation further contains d) propylene glycol, e) glycerol, and f) a propellant, or the pharmaceutical formulation contains 2 to 10% (by weight) of propellant, more preferably wherein the propellant is a hydrocarbon or a hydrofluoroalkane, or, wherein the propellant is propane, butane, isobutene, heptafluoropropane, tetrafluoroethane, dimethylether, or a mixture thereof, or, which contains 6 to 8% (by weight) of propellant and wherein the propellant is propane, butane, isobutene, heptafluoropropane, tetrafluoroethane, dimethylether, or a mixture thereof, or the solubility of at least one pharmaceutically active compound in water is 20 mg/l at 20° C. or less, or the pharmaceutical formulation further contains (R)-1,1,1-Trifluoro-4-(5-fluoro-2,3-dihydrobenzofuran-7-yl)-4-methyl-2-{[-(2-methyl-5 quinolyl)amino]methyl}pentan-2-ol, or the pharmaceutical formulation contains 2 to 50% (by weight) of oleyl alcohol, 3 to 20% (by weight) of cetearyl octanoate, and 5 to 20% (by weight) of vegetable oil.

The cream, foam and oleogel formulations as explicitly disclosed in U.S. Pat. No. 8,282,909 are particularly preferred topical formulations. These cream, foam and oleogel formulations are explicitly incorporated herein by reference:

| Examples (oleogel) | 1 | 2 | 3 | 4 | 5 | Ranges |
|---|---|---|---|---|---|---|
| active compound | 0.10 | 0.10 | 0.10 | 0.10 | 0.10 | 0.001-0.5 |
| Oleyl alcohol | 30.00 | 20.00 | 20.00 | 15.00 | 15.00 | 10.00-40.00 |
| Medium-chained triglycerides | — | 20.00 | 20.00 | 15.00 | 20.00 | 10.00-30.00 |
| Mineral oil | 5.00 | 20.00 | 10.00 | 20.00 | 20.00 | 2.00-25.00 |
| Cetearyl octanoate | 30.00 | 10.00 | 20.00 | 20.00 | 20.00 | 5.00-40.00 |
| Soybean Oil (vegetable oils) | 20.00 | 20.00 | 20.00 | 20.00 | 15.00 | 10.00-30.00 |
| Cyclomethicone | — | 5.90 | 4.90 | 6.90 | 3.90 | 1.00-10.00 |
| Silicon dioxide | 5.00 | 4.00 | 5.00 | — | — | 3.00-10.00 |
| Aluminium stearate | — | — | — | 3.00 | 6.00 | 2.00-8.00 |

| Examples (cream) | 1 | 2 | 3 | 4 | 5 | Ranges |
|---|---|---|---|---|---|---|
| active compound | 0.10 | 0.10 | 0.10 | 0,10 | 0.10 | 0.001-0.50 |
| Oleyl alcohol | 10.00 | 10.00 | 10.00 | 5.00 | 10.00 | 3.00-15.00 |
| Medium-chained triglycerides | — | — | — | 5.00 | — | 2.00-10.00 |
| Mineral oil | 8.00 | 4.00 | 4.00 | 4.00 | 4.00 | 2.00-10.00 |
| Cetearyl octanoate | 3.00 | 10.00 | 10.00 | 10.00 | 10.00 | 2.00-15.00 |
| Soybean Oil (vegetable oils) | 6.00 | 4.00 | 4.00 | 4.00 | 4.00 | 3.00-15.00 |
| Cyclomethicone | 3.50 | 2.50 | 2.50 | 2.50 | 2.50 | 1.00-5.00 |
| Stearyl alcohol | 2.00 | 2.00 | 2.00 | 2.00 | 2.00 | 1.00-5.00 |
| Butylated hydroxytoluene | 0.05 | 0.05 | 0.05 | 0.05 | 0.05 | 0.01-0.20 |
| Glycerol (85%) | 8.00 | 8.00 | 8.00 | 8.00 | 8.00 | 4.00-10.00 |
| Macrogolglycerolhydroxystearate | 1.50 | 1.50 | 1.50 | 1.50 | 1.50 | 0.50-5.00 |
| Povidone 90 | 4.00 | 4.00 | 4.00 | 4.00 | 4.00 | 2.00-8.00 |
| Propylene Glycol | 8.00 | 8.00 | 8.00 | 8.00 | 8.00 | 4.00-10.00 |
| Acrylic acid copolymer | 0.30 | — | 0.30 | 0.30 | — | 0.10-1.00 |
| Hydroxyethylcellulose | — | 1.50 | — | — | — | 0.10-1.00 |
| Acrylic acid | — | — | — | — | 1.00 | 0.50-2.00 |
| Trometamol solution 10% | to pH 7 | to pH 7 | to pH 7 | to pH 7 | to pH 7 | to pH 7.0 |
| Purified water | [ad 100.0] | [ad 100.0] | [ad 100.0] | [ad 100.0] | [ad 100.0] | [ad 100.0] |

| Examples (foam) | 1 | 2 | 3 | 4 | 5 | Ranges |
|---|---|---|---|---|---|---|
| active compound | 0.10 | 0.10 | 0.10 | 0.10 | 0.10 | 0.001-0.50 |
| Oleyl alcohol | 10.00 | 5.00 | 3.00 | 10.00 | 4.00 | 2.00-15.00 |
| Medium-chained triglycerides | — | 5.00 | 10.0 | — | 6.00 | 2.00-15.00 |
| Mineral oil | 4.00 | — | — | — | — | 2.00-6.00 |
| Cetearyl octanoate | 3.00 | 5.00 | 3.00 | 5.00 | 4.00 | 2.00-10.00 |
| Soybean Oil (vegetable oils) | 3.00 | 5.00 | 2.00 | — | 5.00 | 2.00-10.00 |
| Stearyl alcohol | 2.00 | — | — | — | 1.00 | 0.50-5.00 |
| Cetostearyl alcohol | — | 1.50 | 1.50 | 1.50 | 1.00 | 0.50-5.00 |
| Glyceryl Stearate | — | 0.50 | 0.50 | 0.50 | 0.50 | 0.50-2.00 |
| Glycerol (85%) | 8.00 | — | 4.00 | 8.00 | — | 2.00-10.00 |
| Macrogolglycerolhydroxystearate | 1.50 | — | — | — | 1.50 | 0.50-5.00 |
| Macrogol-400-Stearate | — | 2.50 | 2.00 | 2.50 | 1.00 | 0.50-5.00 |

-continued

| Examples (foam) | 1 | 2 | 3 | 4 | 5 | Ranges |
|---|---|---|---|---|---|---|
| Polysorbate 80 | — | 1.00 | 1.50 | 1.00 | 1.00 | 0.50-3.00 |
| Povidone 90 | 2.00 | — | — | — | — | 0.00-3.00 |
| Propylene Glycol | 8.00 | 8.00 | 8.00 | 10.00 | 4.00 | 2.00-10.00 |
| Methylcellulose | 0.10 | 0.10 | 0.10 | 0.15 | 0.10 | 0.05-1.00 |
| Xanthan gum | 0.30 | 0.20 | 0.10 | 0.20 | 0.30 | 0.05-2.00 |

| Examples (foam) | 1 | 2 | 3 | 4 | 5 | Ranges |
|---|---|---|---|---|---|---|
| Trometamol 10% | to pH 7 | to pH 7 | to pH 7 | to pH 7 | to pH 7 | to pH 7 |
| Purified water | [ad 100.0] | [ad 100.0] | [ad 100.0] | [ad 100.0] | [ad 100.0] | [ad 100.0] |
| Propellant | 2.0-10.0 for all examples | | | | | |

In another embodiment, the present invention relates to an in vitro method for identifying a subject suffering from impaired skin wound healing to be responsive to the treatment with a Glucocorticoid Receptor Modulator (SEGRM), or a pharmaceutically acceptable salt thereof, comprising performing steps i) and/or ii):

i) measuring the proliferation of fibroblast cells, and optionally the amount of at least one IL-1 cytokine marker in the supernatant of fibroblast cells, in the presence of:
   (1) a wound exudate sample or wound biofilm sample obtained from the skin wound of said subject, and
   (2) at least one Selective Glucocorticoid Receptor Modulator (SEGRM), or a pharmaceutically acceptable salt thereof;

ii) measuring the fibroblast-derived matrix formation by fibroblast cells in the presence of:
   (1) a wound exudate sample or wound biofilm sample obtained from the skin wound of said subject, and
   (2) at least one Selective Glucocorticoid Receptor Modulator (SEGRM), or a pharmaceutically acceptable salt thereof;

wherein the subject is identified to be responsive to the treatment with a Selective Glucocorticoid Receptor Modulator (SEGRM), or a pharmaceutically acceptable salt thereof, in case the value of proliferation of fibroblast cells measured in step i) and/or the value of the fibroblast-derived matrix formation by fibroblast cells measured in step ii) is at least 20% above a control value established in the absence of the at least one Selective Glucocorticoid Receptor Modulator (SEGRM), or pharmaceutically acceptable salt thereof of (2) and, optionally, in case the value for the amount of the at least one IL-1 cytokine marker in the supernatant of fibroblast cells obtained in step i) is below a control value established in the absence of the at least one Selective Glucocorticoid Receptor Modulator (SEGRM), or pharmaceutically acceptable salt thereof of (2).

In a preferred embodiment of the in vitro method of the invention, in addition, step iiia) and/or one, two, three or four of the following steps iiib) to iiie) are performed:

iiia) measuring the proliferation of keratinocyte cells in the presence of:
   (1) a wound exudate sample, or wound biofilm sample, obtained from the skin wound of said subject, and
   (2) at least one Selective Glucocorticoid Receptor Modulator (SEGRM), or pharmaceutically acceptable salt thereof, iiib) measuring the amount(s) of one or more M1 marker(s) and one or more M2 marker(s) in the supernatant of macrophages incubated with
   (1) a wound exudate sample or wound biofilm sample obtained from said skin wound, and
   (2) at least one Selective Glucocorticoid Receptor Modulator (SEGRM), or pharmaceutically acceptable salt thereof,
   wherein the macrophages are in co-culture with fibroblasts, and
   wherein the one or more M1 markers are selected from CXCL10 and IL-23p19, and the one or more M2 markers are selected from CCL22 and CCL18, iiic) measuring the amount(s) and/or frequency distribution(s) of one or more M1 cell surface marker(s) and one or more M2 cell surface marker(s) on macrophages incubated with
   (1) a wound exudate sample or wound biofilm sample obtained from said skin wound, and
   (2) at least one Selective Glucocorticoid Receptor Modulator (SEGRM), or pharmaceutically acceptable salt thereof,
   wherein the macrophages are in co-culture with fibroblasts, and
   wherein the one or more M1 cell surface markers are selected from CD38, CD64 and CD197, and wherein the one or more M2 cell surface markers are selected from CD200 receptor, CD206 and CD209, iiid) measuring the expression level(s) of one or more M1 marker mRNA(s) and one or more M2 marker mRNA (s) in macrophages incubated with
   (1) a wound exudate sample or wound biofilm sample obtained from said skin wound, and
   (2) at least one Selective Glucocorticoid Receptor Modulator (SEGRM), or pharmaceutically acceptable salt thereof,
      wherein the macrophages are in co-culture with fibroblasts, and
      wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, iiie) measuring the amount(s) of one or more cytokine markers selected from IL-1alpha, IL-1beta and TNF-alpha in the supernatant of macrophages incubated
   (1) with a wound exudate sample or wound biofilm sample obtained from said skin wound, and (2) at least one Selective Glucocorticoid Receptor Modulator (SEGRM), or pharmaceutically acceptable salt thereof, and wherein the subject is identified to be responsive to the treatment with a Selective Glucocorticoid Receptor Modulator (SEGRM), or pharmaceutically acceptable salt thereof, in case the value of proliferation of fibroblast cells measured in step i) and/or the value of the fibroblast-derived matrix formation by fibroblast cells measured in step ii) and/or the value of the proliferation of keratinocyte cells in step iiia) is at least 20% above a control value established in the absence of the at least one Selective Glucocorticoid Receptor Modulator (SEGRM), or pharmaceutically acceptable salt thereof of (2), and/or in case one or more of the following applies:

the ratio of amount(s) of one or more M1 marker(s) to the amount(s) of one or more M2 marker(s) obtained in iiib) is/are below a control value established in the absence of the at least one Selective Glucocorticoid Receptor Modulator (SEGRM), or pharmaceutically acceptable salt thereof of (2), the ratio of amount(s) and/or frequency distribution(s) of one or more M1 cell surface marker(s) to the amount(s) and/or frequency distribution(s) of one or more M2 cell surface marker(s) obtained in iiic) is/are below a control value established in the absence of the at least one Selective Glucocorticoid Receptor Modulator (SEGRM), or pharmaceutically acceptable salt thereof of (2), in particular wherein the ratio is selected from a CD38/CD209 ratio, a CD197/CD209 ratio and a CD197/CD206 ratio, the ratio of expression level(s) of one or more M1 marker mRNA(s) to the expression level(s) of one or more M2 marker mRNA(s) obtained in iiid) is/are below a control value established in the absence of the at least one Selective Glucocorticoid Receptor Modulator (SEGRM), or pharmaceutically acceptable salt thereof of (2), the value obtained in iiie) is below a control value established in the absence of the at least one Selective Glucocorticoid Receptor Modulator (SEGRM), or pharmaceutically acceptable salt thereof of (2).

In a preferred embodiment, the in vitro method of the invention is characterized by the features of the preferred embodiments of the Selective Glucocorticoid Receptor Modulator (SEGRM), or a pharmaceutically acceptable salt thereof, for use of the invention.

In yet another embodiment, the present invention relates to a kit or kit-of-parts, comprising:

(a) a pharmaceutical composition comprising at least one Selective Glucocorticoid Receptor Modulator (SEGRM), or a pharmaceutically acceptable salt thereof, and (b) a diagnostic kit comprising one or more of the following:

i) fibroblast cells, ii) a support having a plurality of defined areas or cavities, wherein a subset of areas or cavities are (i) coated with adhesion enhancing agent, and/or (ii) are filled with fibroblast-derived matrix (FDM), iii) a matrix promoting supplement.

In a preferred embodiment, the kit or kit-of-parts of the invention is characterized by the features of the preferred embodiments of the Selective Glucocorticoid Receptor Modulator (SEGRM), or a pharmaceutically acceptable salt thereof, for use of the invention.

Accordingly, it is understood that the preferred embodiments described in the context of other embodiments of the present invention also apply to this embodiment of the invention.

The pharmaceutical compositions, cells and matrix promoting supplement may be provided in containers, vials, syringes, ampules or the like.

The diagnostic kit of b) optionally further comprises one or more of the following: iv) keratinocyte cells, v) a matrix promoting supplement, vi) monocyte cells, and vii) binding agents, preferably antibodies, which specifically recognize one or more M1 marker(s) and one or more M2 marker(s), and/or binding agents, preferably antibodies, which specifically recognize one or more M1 surface marker(s) and one or more M2 surface marker(s), and/or probes which specifically recognize one or more M1 marker mRNA(s) and one or more M2 marker mRNA(s)

viii) binding agents, preferably antibodies, which specifically recognize one or more one or more cytokine markers selected from IL-1alpha, IL-1beta and TNF-alpha, or hybridization probes, which specifically hybridize to cytokine marker mRNAs selected from IL-1alpha, IL-1beta and TNF-alpha.

In a more preferred embodiment, the diagnostic kit of b) further comprises viii) binding agents, preferably antibodies, which specifically recognize one or more cytokine markers selected from IL-1alpha, IL-1beta and TNF-alpha, or hybridization probes, which specifically hybridize to cytokine marker mRNAs selected from IL-1alpha, IL-1beta and TNF-alpha.

In a more preferred embodiment, the cytokine markers are selected from IL-1alpha, IL-1beta, in particular IL-1beta.

Preferred M1 and M2 marker(s), cell surface marker(s) and/or marker mRNA(s) are described above.

In one preferred embodiment, the binding agents, preferably antibodies of vii) above are binding agents, preferably antibodies, which specifically recognize one or one more M1 cell surface marker(s) and one or more M2 cell surface marker(s), wherein the one ore more M1 cell surface markers are selected from CD38, CD64 and CD197, and wherein the one or more M2 cell surface markers are selected from CD200 receptor, CD206 and CD209, and, optionally:

binding agents, preferably antibodies, which specifically recognize one or more M1 marker(s) and one or more M2 marker(s), and/or probes which specifically recognize one or more M1 marker mRNA(s) and one or more M2 marker mRNA(s), wherein the one or more M1 markers are selected from CXCL10 and IL-23p19, and the one or more M2 markers are selected from CCL22 and CCL18, and wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18.

Accordingly, in another more preferred embodiment, the one or more M1 cell surface marker is selected from CD38 and the one or more M2 cell surface marker is selected from CD209, or the one or more M1 cell surface marker is selected from CD197 and the one or more M2 cell surface marker is selected from CD209 and CD206.

In one preferred embodiment, the keratinocyte cells are selected from HaCaT cells and primary keratinocyte cells, in particular human primary keratinocyte cells.

In a more preferred embodiment, the keratinocyte cells used in the present invention are HaCaT cells.

Fibroblast-derived matrix (FDM) is obtainable by (i) seeding primary human dermal fibroblast cells on a support, which is pre-coated with an adhesion enhancing agent, such as gelatin, (ii) culturing the cells on the support, preferably until confluence is reached and (iii) contacting the cells with a matrix promoting supplement, such as Vitamin C or a physiologically acceptable salt thereof, or 2-phospho-L-ascorbic acid or a physiologically acceptable salt thereof, or a combination of EGF and insulin. FDM may be formed in situ or may be transferred to the support after formation.

Moreover, supports, such as chips are preferred, which allow for performing the in vitro methods of the invention or method steps of the medical uses of the invention. For example, a chip may be provided, which allows for identifying subjects to be responsive to a treatment of impaired wound healing with a SEGRM or the pharmaceutically acceptable salt thereof.

Therefore, in another preferred embodiment, the present invention relates to a kit or kit-of-parts of the invention, wherein the support ii) of the diagnostic kit (b) is suitable for performing a method of the present invention or method steps of the medical uses of the invention, wherein the support comprises a plurality of defined areas or cavities and wherein:

- a) a subset of areas or cavities are coated with an adhesion enhancing agent,
- b) a subset of areas or cavities are coated with an adhesion enhancing agent and/or filled with fibroblast-derived matrix (FDM),
- c) a subset of areas or cavities are untreated,
- d) optionally:
  - d1) a subset of areas or cavities contain binding agents, preferably antibodies, which specifically recognize one or more M1 marker(s), and
  - d2) a subset of areas or cavities contain binding agents, preferably antibodies, which specifically recognize one or more one or more M2 marker(s),
- e) optionally:
  - e1) a subset of areas or cavities contain binding agents, preferably antibodies, which specifically recognize one or more M1 surface marker(s), and
  - e2) a subset of areas or cavities contain binding agents, preferably antibodies, which specifically recognize one or more M2 surface marker(s),
- f) optionally:
  - f1) a subset of areas or cavities contain probes which specifically recognize one or more M1 marker mRNA(s), and
  - f2) a subset of areas or cavities contain probes which specifically recognize one or more M2 marker mRNA(s), and
- g) optionally: a subset of areas or cavities contain binding agents, preferably antibodies, which specifically recognize one or more cytokine markers selected from IL-1alpha, IL-1beta and TNF-alpha wherein the subsets a) to g) are not overlapping, preferably

- (x) at least some of the areas or cavities pursuant to a) further contain fibroblast cells, and/or
- (xi) at least some of the areas or cavities pursuant to (x) or b) further contain monocyte cells, and/or
- (xii) at least some of the areas or cavities pursuant to c) further contain fibroblast cells, and/or
- (xiii) at least some of the areas or cavities pursuant to c) further contain keratinocyte cells, wherein the areas or cavities pursuant to (xii) and (xiii) are not overlapping.

In one preferred embodiment, the one or more M1 markers are selected from CXCL10 and IL-23p19, and the one or more M2 markers are selected from CCL22 and CCL18.

In one preferred embodiment, the one or more M1 cell surface markers are selected from CD38, CD64 and CD197, and wherein the one or more M2 cell surface markers are selected from CD200 receptor, CD206 and CD209.

In one preferred embodiment, the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18.

In one more preferred embodiment, the support of the kit or kit-of-parts is a chip, array, such as a microarray or nanoarray, a plate, such a multiwell plate, or a dish, and/or the support is a plastic support.

The solid support of the kit or kit-of-parts preferably contains a plurality of defined cavities. Cavities allow for filling of the space and therefore allow for a 3D cell culture. For example, a multiwell plate or a microarray or nanoarray comprising a plurality of defined cavities may be used. In the examples, a multiwell plate was successfully used. Preferably, the solid support does not substantially interfere with the viability of the cells and/or is suitable for culturing cells, for example the support may be a plastic support. For 3D cell culture, the solid support may contain a plurality of defined wells. For example, multi-well plates may be used. In one preferred embodiment, the support comprises 2, 3, 4, 5, 6, 7, 8, 9, 10 or more defined areas or cavities, such as 2, 3, 4, 5, 6, 7, 8, 9 or 10 to $10^5$, 2, 3, 4, 5, 6, 7, 8, 9 or 10 to $10^4$, 2, 3, 4, 5, 6, 7, 8, 9 or 10 to $10^3$, or 2, 3, 4, 5, 6, 7, 8, 9 or 10 to $10^2$defined areas or cavities.

In a yet further embodiment, the present invention relates to a method of preventing or treating impaired skin wound healing in a subject, comprising administering to a subject in need thereof a therapeutically effective amount of SEGRM, or a pharmaceutically acceptable salt thereof.

"Effective amount" refers to the amount sufficient to induce a desired biological, pharmacological, or therapeutic outcome in a subject. A therapeutically effective amount of a compound can be employed as a zwitterion or as a pharmaceutically acceptable salt. A therapeutically effective amount means a sufficient amount of the compound to treat or prevent impaired skin wound healing at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

FIGURE LEGENDS

FIG. 1: shows profiling of the active SEGRM compound BI-653048 in comparison with its inactive analogue BI-3047 in the human dermal fibroblast proliferation assay (2D) with or without wound exudate from patients 1-3 (1A-1C). Fibroblast proliferation in medium in the absence of WE is shown in 1D. Filled circles: graded concentrations of BI-653048; empty triangles: graded concentrations of BI-3047. The active compound reversed inhibition of wound exudate (WE)-induced fibroblast proliferation, while the inactive analogue had no effect.

FIG. 2: shows the effects of the active SEGRM compound BI-653048 in comparison with its inactive analogue BI-3047 in the presence of WE-1 on fibroblast proliferation (2A) as well as IL-1β secretion into the supernatant (2B). Filled circles: graded concentrations of BI-653048; empty triangles: graded concentrations of BI-3047. The active compound dose-dependently reversed inhibition of wound exudate (WE)-induced fibroblast proliferation and inhibited IL-1β secretion at the same concentrations. The inactive analogue had no effect on proliferation and much less effect on IL-1β secretion.

Figure 3:
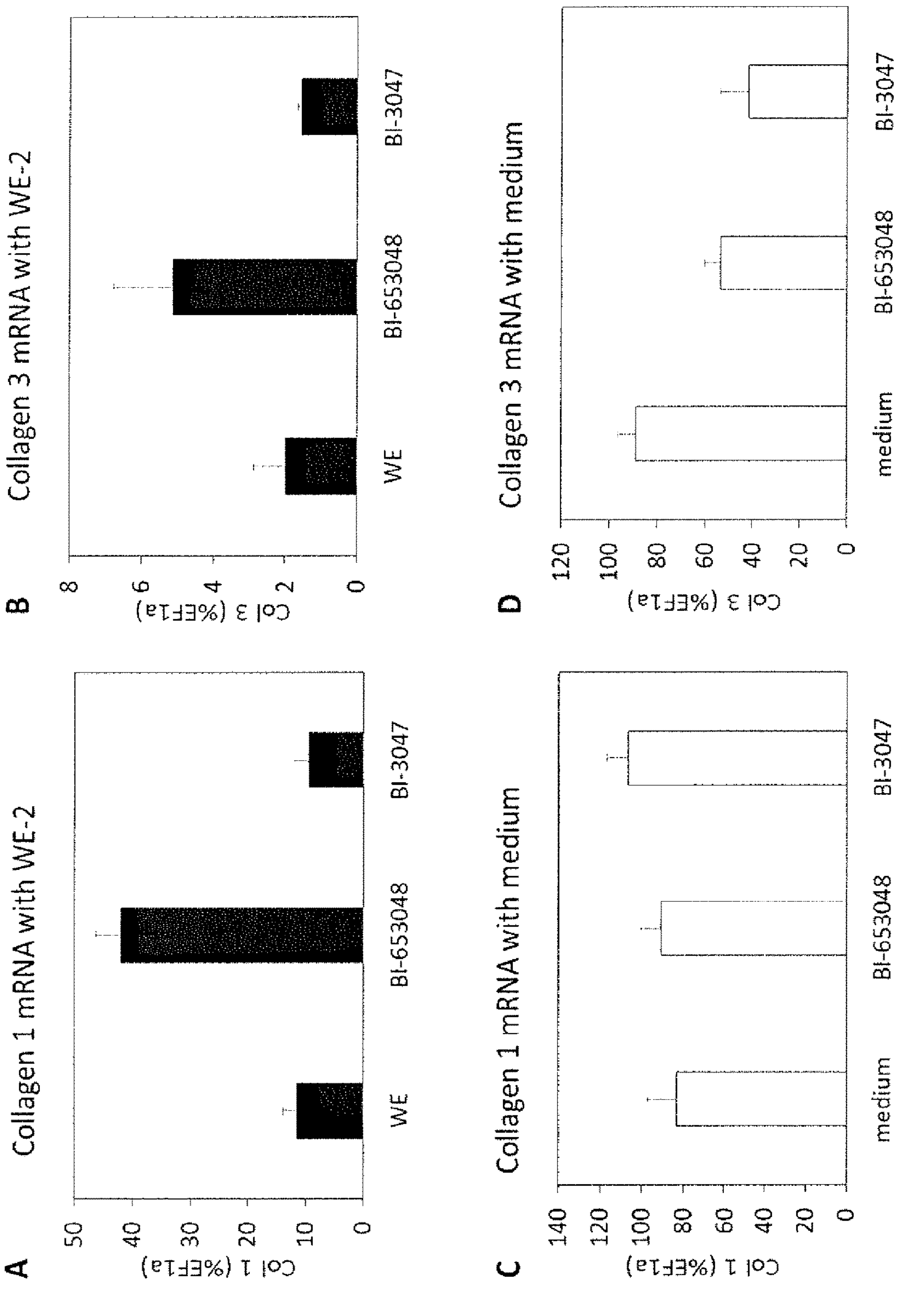
Figure 4:
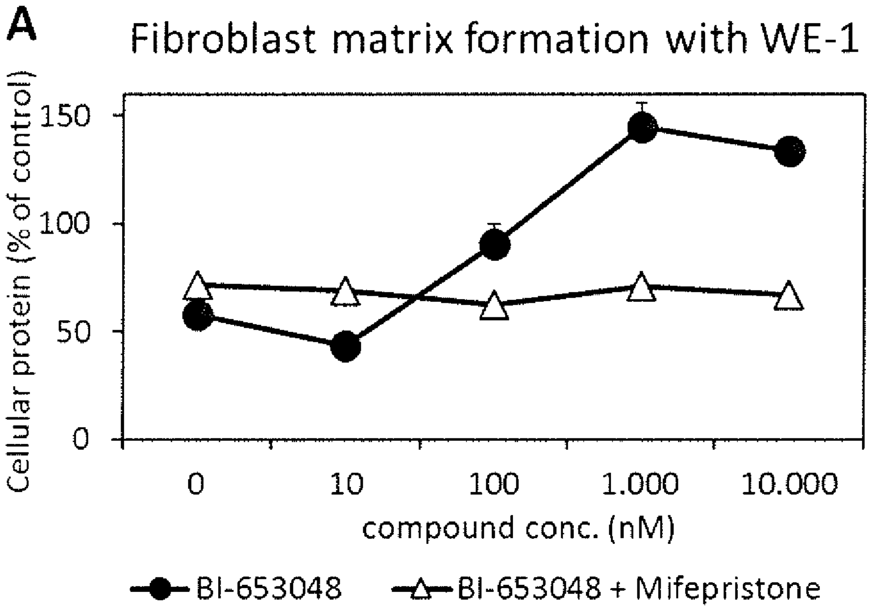

FIG. 3: shows the effects of the active SEGRM compound BI-653048 in comparison with its inactive analogue BI-3047 in the presence of WE-2 on the expression of mRNAs for collagens 1 and 3 in the fibroblast proliferation assay. Filled symbols (3A and 3B): 72-hour incubation performed in the presence of WE-2; empty symbols (3C and 3D): 72-hour incubation performed in medium in the absence of WE. Both compounds were used at 1 μM. The active compound enhanced collagen 1- and collagen 3 mRNA expression in the presence of WE, but not in medium.

FIG. 4: shows the effect of graded concentrations of the SEGRM BI-653048, both in the presence and absence of the glucocorticoid receptor antagonist mifepristone (concentration 1 μM) in 3D fibroblast culture regarding the formation of fibroblast-derived matrix with WE-1. The matrix-promoting effects of BI-653048 can be abrogated by addition of mifepristone, indicating that these effects are mediated by the glucocorticoid receptor.

FIG. 5: shows the effects of the SEGRM compounds mapracorat and BI-53048 in the presence of WE-4 on fibroblast proliferation. Filled circles: graded concentrations of BI-53048; filled squares: graded concentrations of mapracorat. Both compounds dose-dependently reversed inhibition of wound exudate (WE)-induced fibroblast proliferation, albeit at different concentrations.

FIG. 6: shows the effects of graded concentrations of mapracorat in the presence of WE-1 on the expression of mRNAs for collagen 1 in the fibroblast proliferation assay. Filled symbols (6A): 72-hour incubation performed in the presence of WE-1; empty symbols (6B): 72-hour incubation performed in medium in the absence of WE. Mapracorat dose-dependently enhanced collagen 1 mRNA expression in the presence of WE, but not in medium.

FIG. 7: shows the effects of graded concentrations of mapracorat in the presence of WE-1 on the expression of mRNAs for collagen 3 in the fibroblast proliferation assay. Filled symbols (7A): 72-hour incubation performed in the presence of WE-1; empty symbols (7B): 72-hour incubation performed in medium in the absence of WE. Mapracorat at all three concentrations enhanced collagen 3 mRNA expression in the presence of WE, but not in medium.

Figure 8:
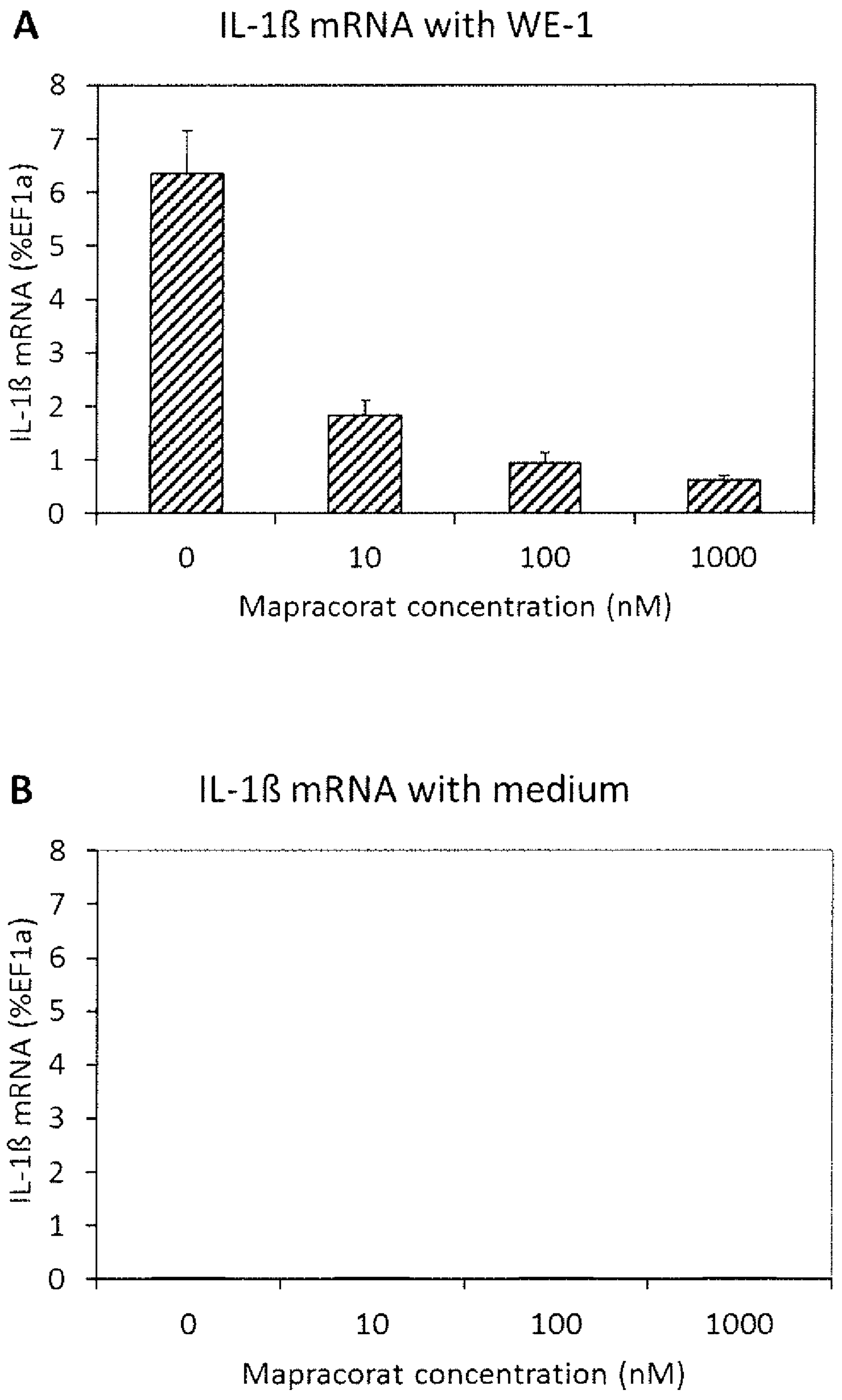

FIG. 8: shows the effects of graded concentrations of mapracorat in the presence of WE-1 on the expression of mRNAs for IL-1β in the fibroblast proliferation assay. Filled symbols (8A): 72-hour incubation performed in the presence of WE-1; empty symbols (8B): 72-hour incubation performed in medium in the absence of WE. Mapracorat dose-dependently inhibited IL-1β mRNA expression in the presence of WE. There was no IL-1β induction in medium.

Figure 9:
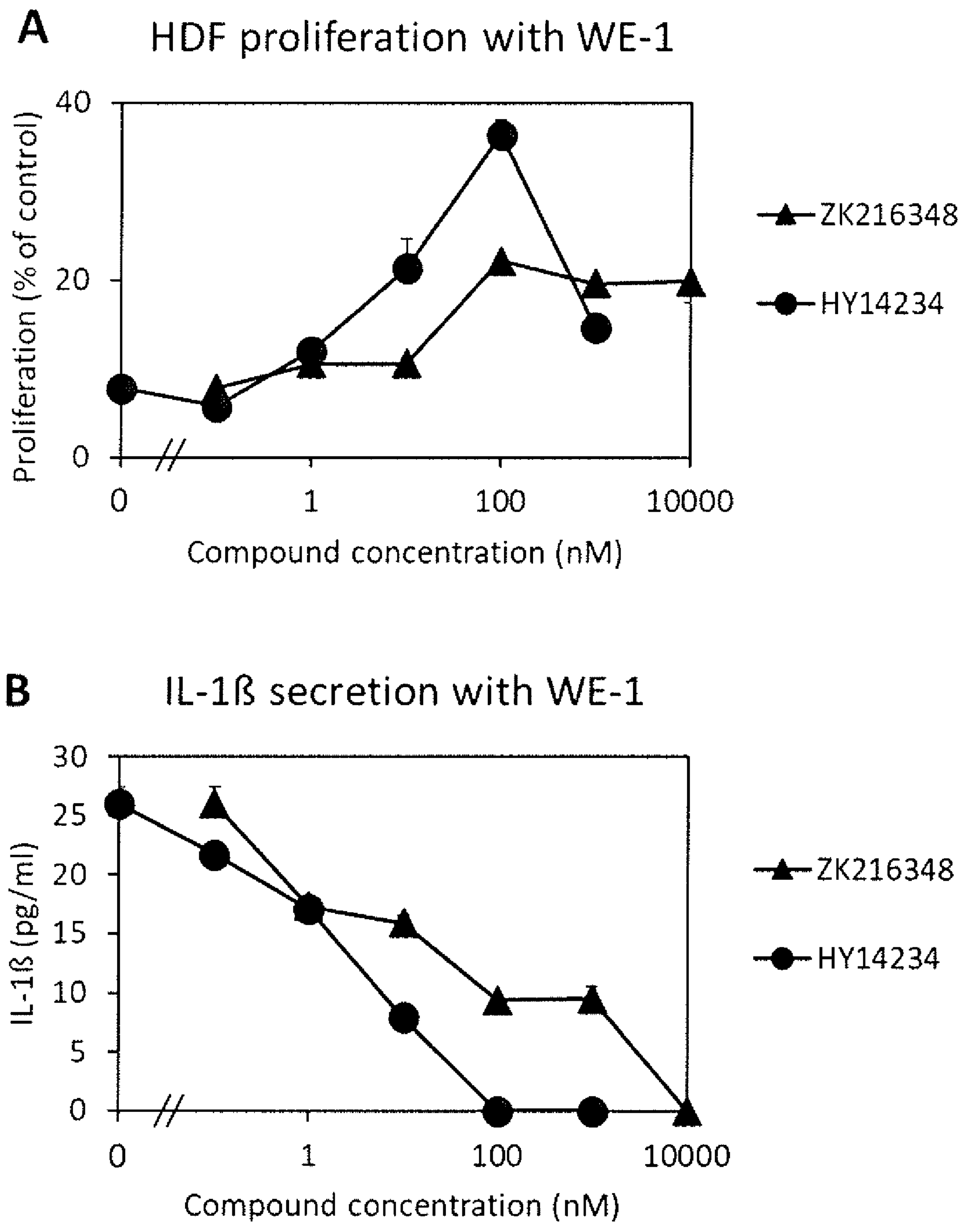

FIG. 9: shows the effects of the SEGRM compounds ZK216348 and HY14234 in the presence of WE-1 on fibroblast proliferation (9A) as well as IL-1β secretion into the supernatant (9B). Filled circles: graded concentrations of HY14234; filled triangles: graded concentrations of ZK216348. All tested compounds led to a dose-dependent partial reversion of the wound exudate (WE)-induced inhibition of fibroblast proliferation and they inhibited IL-1β secretion at the same concentrations. The efficacy of ZK216348 was not as high as for HY14234.

Figure 10:
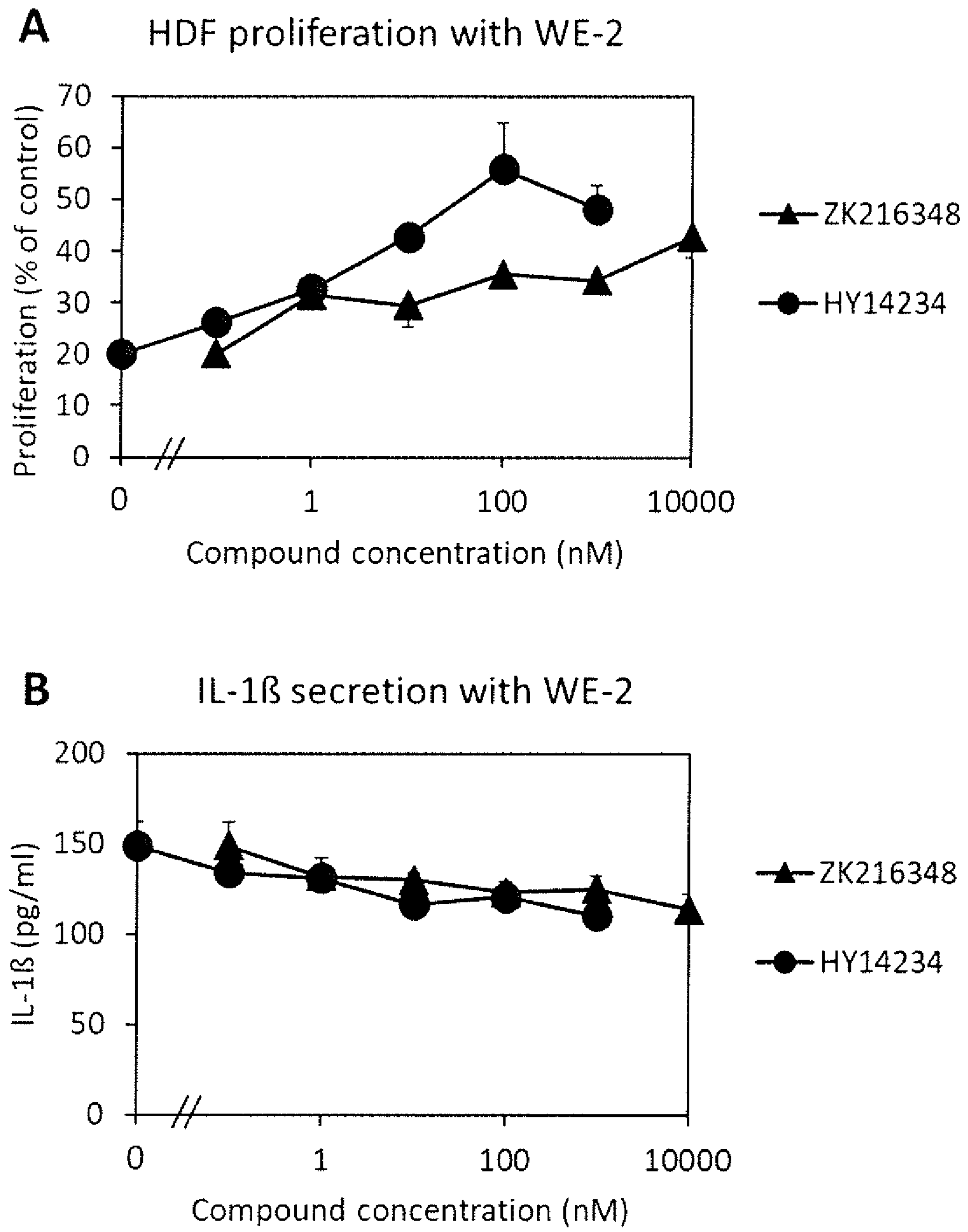

FIG. 10: shows the effects of the SEGRM compounds ZK216348 and HY14234 in the presence of WE-2 on fibroblast proliferation (10A) as well as IL-1β secretion into the supernatant (10B). Filled circles: graded concentrations of HY14234; filled triangles: graded concentrations of ZK216348. All tested compounds dose-dependently reversed inhibition of wound exudate (WE)-induced fibroblast proliferation, while in the context of WE-2, inhibition of IL-1β secretion was negligible.

Figure 11:
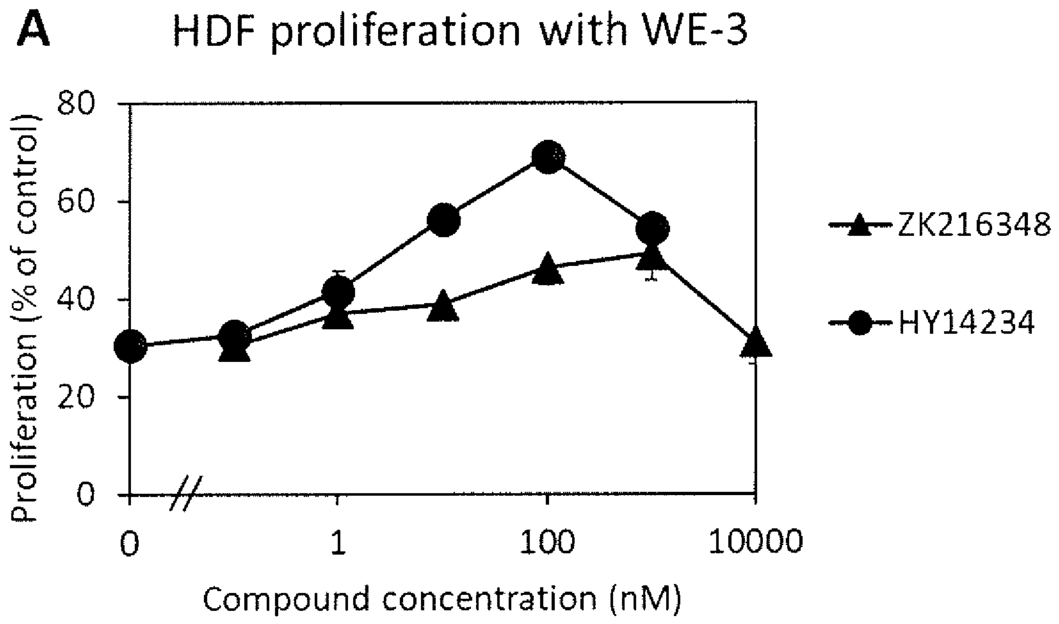
Figure 11:
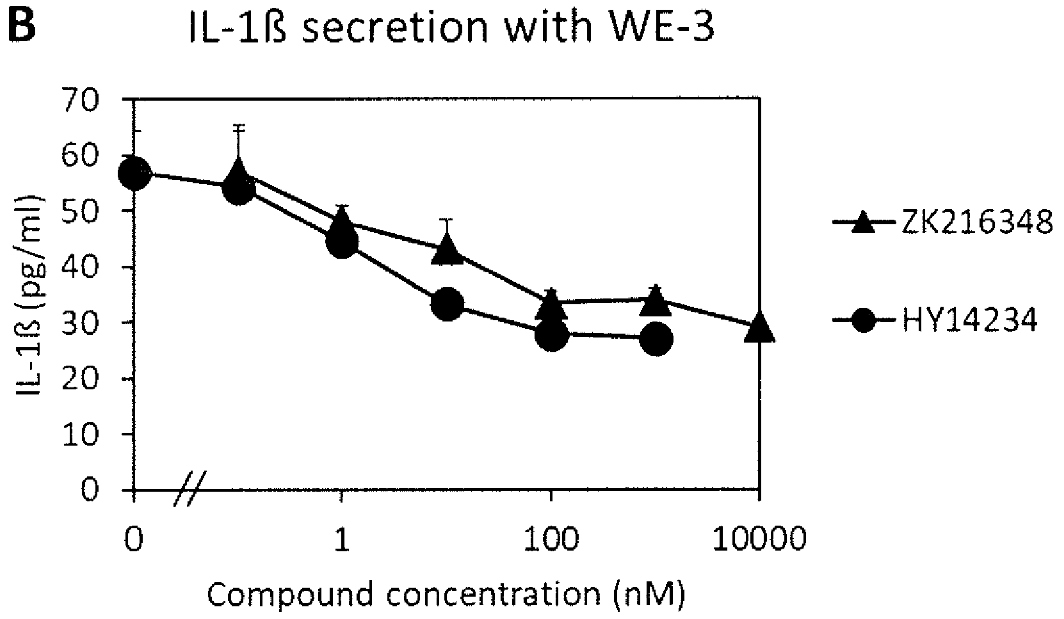

FIG. 11: shows the effects of the SEGRM compounds ZK216348 and HY14234 in the presence of WE-3 on fibroblast proliferation (11A) as well as IL-1β secretion into the supernatant (11B). Filled circles: graded concentrations of HY14234; filled triangles: graded concentrations of ZK216348. All tested compounds dose-dependently reversed inhibition of wound exudate (WE)-induced fibroblast proliferation and inhibited IL-1β secretion at the same concentrations. The efficacy of ZK216348 was not as high as for HY14234.

FIG. 12: shows the effect of a plurality of SEGRM in 3D fibroblast culture with WE from patient #92. AZD7594 was the most active of the SEGRM tested in 3D culture, followed by mapracorat and BI653048. This is in line with their potencies for glucocorticoid receptor activation ($EC_{50}$ values of 0.9 nM, 1.9 nM and 55 nM, respectively). The inactive compound BI3047 did not induce matrix formation. Filled diamonds: AZD7594; filled circles: mapracorat; filled squares: HY14234; filled triangles: BI653048; open triangles: BI3047; x: ZK216348.

FIG. 13: shows the effect of mapracorat in a pig model of delayed wound healing. Wounds were induced for 5 days on the back of pigs using human chronic wound exudates WE-01 and WE-02 or normal human serum in the presence of the TLR7/8 agonist R848 as inducer of inflammation (FIGS. 13A-C) or human serum alone as a control (FIG. 13D). Compound treatment started on day 6 and continued until day 10. Total wound score (wound appearance, size, content, pus, crust, erythema, erythema width, swelling, necrosis) was determined daily until day 12.

Mapracorat (MAPRA) at 10 mM and 1 mM reduced the wound score from days 6 to 12 with WE-01 (FIG. 13A), WE-02 (FIG. 13B) and R848 (FIG. 13C) as inducers of delayed wound healing. Mapracorat did not have any negative effect on the healing of control wounds in the presence of human serum (FIG. 13D).

While the general effect of mapracorat was similar in both pigs, the extent of wound score reduction differed, depending on the individual pig and the stimulus (WE and/or R848) used. Pig #2 responded better than pig #1, and the ameliorating effect of mapracorat was better for WE-02 then WE-01. In one preferred embodiment, a personalized medicine approach for individual patients may be performed, by performing methods described herein, including pretesting of the exudates of the patients against specific drugs, as described above.

Figure 14:
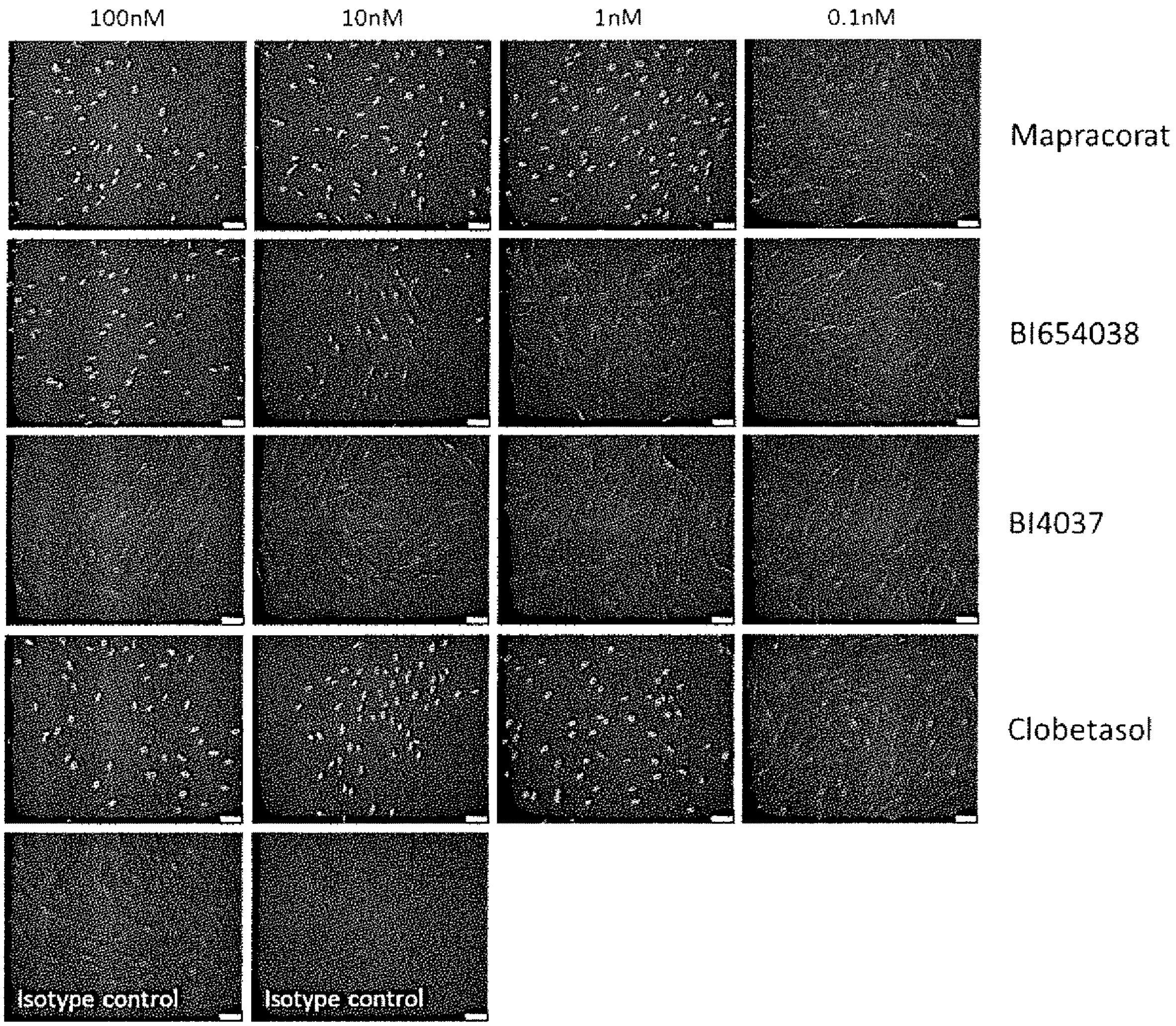

FIG. 14: shows the translocation of the glucocorticoid receptor from the cytoplasm (C) of fibroblasts into the nucleus (N) as a measure of activity. The cells were incubated with graded compound concentrations and intracellular glucocorticoid receptor localization was determined by indirect immunofluorescence, using an antibody directed against the receptor.

Both mapracorat and the active BI653048 show nuclear translocation at low concentrations (1-10 nM), while BI3047, the inactive stereoisomer of BI653048, is inactive up to 100 nM. Clobetasol as a positive control shows nuclear staining as well.

FIG. 15: the table shows the effects of 1 μM mapracorat on fibroblast proliferation in the presence of a high number of different wound exudates from chronic, non-healing skin wound of human patients. The level of proliferation in the presence of the respective WE was set to 100%, and formed the basis for the calculation of the effect of mapracorat. All values >120% (mean of WE control+2 SD) are considered growth promoting. In one preferred embodiment of the present invention, patients are preselected using methods of the present invention who are most likely to respond effectively to therapy in a personalized way, as described above.

Figure 16:
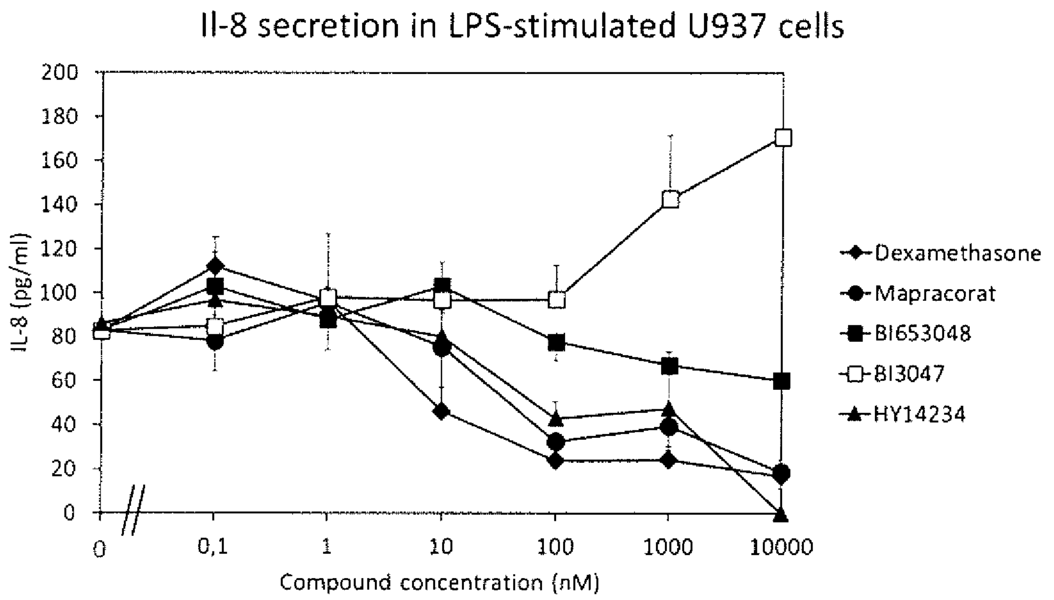
Figure 16:
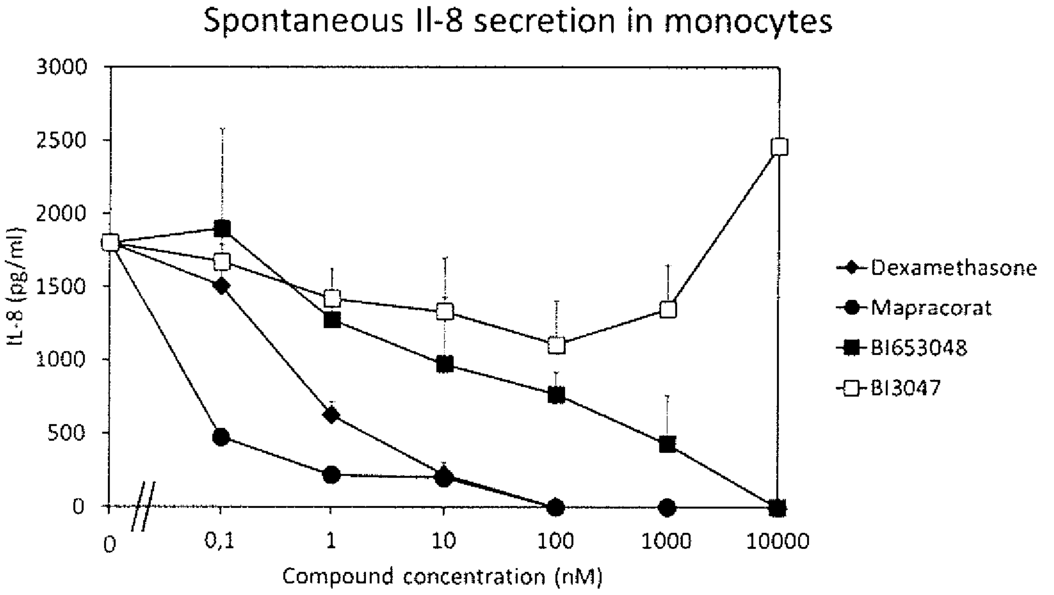

FIG. 16: shows the inhibition of LPS-induced IL-8 secretion in U937 cells (A) and of spontaneous IL-8 secretion in human monocytes (B) in response to the active SEGRM mapracorat (filled circles), HY14234 (filled triangles) and BI653048 (filled squares), the inactive compound BI3047 (open squares) and, as a comparator, the glucocorticoid dexamethasone (filled diamonds). The active SEGRM inhibited both LPS-induced and spontaneous IL-8 secretion in U937 and primary human monocytes, respectively, while the inactive stereoisomer showed even induced IL-8 secretion at the highest concentrations. The comparator corticosteroid, dexamethasone, inhibited IL-8 in a similar fashion as the SEGRM, thus confirming the anti-inflammatory properties of these compounds.

EXAMPLES

Example 1: Assays Used in the Invention

Abbreviations

Abbreviation Description
DMSO Dimethylsulfoxide
FACS Fluorescence activated cell sorting
FCS Fetal calf serum
FDM Fibroblast-derived matrices
HaCaT Human keratinocyte cell line
HBSS Hank's balanced salt solution
HDF Human dermal fibroblasts
HGF Hepatocyte growth factor
M-CSF Macrophage colony stimulating factor
PBS Phosphate buffered saline
RPMI Roswell Park Memorial Institute medium
SRB Sulforhodamine B
TGFbeta Transforming growth factor beta (TGF-β)
WE Wound exudate The assays described in Examples 1.1 and 1.2 represent predictive models for skin wound healing. Most of the non-healing wound exudates (WE) obtained from a variety of patients inhibit proliferation of primary human fibroblasts (HDF) in the assay as described in Example 1.1 and also inhibit the formation of fibroblast-derived matrices (FDM) in 3D, as described in Example 1.2.

Example 1.1: Fibroblast Proliferation Assay: Measuring the Proliferation of Fibroblast Cells and the Secretion of IL-1β in the Presence of a Wound Exudate Sample Obtained from a Skin Wound, in Particular Chronic Human Skin Wounds Primary human dermal fibroblasts (HDF) were purchased from CELLnTEC, Bern. They were routinely grown in Dulbecco's modified Eagle's medium (DMEM) containing 10% FCS, 2 mM glutamine, and 100 U/ml penicillin/100 μg/ml streptomycin. Media, antibiotics, and glutamine were bought from Lonza. The cells were used at passage 5-15. Cells were trypsinized and seeded at 2500 cells/well in 30 μl into the inner wells of 384-well plates in the absence or presence of graded compound concentrations with or without different dilutions of sterile-filtered WE in medium. For control samples, 30 μl medium was added instead of specific stimuli. The outer wells were loaded with sterile water. The cells were incubated for 72 hours at 37° C.

At the end of the incubation period, supernatants were removed for the determination of IL-1β, and the cells were fixed with 4% paraformaldehyde (Morphisto) for 15 minutes at room temperature and washed 3 times with PBS. A control plate was fixed after the overnight adherence of the cells (day 1) to determine the starting cell number.

Total cellular protein was determined as a measure of cell number by staining the fixed cells with sulforhodamine B (SRB, Sigma). A 0.4% SRB solution in 1% acetic acid was added to the wells for 30 minutes. The wells were then washed with 1% acetic acid until the wash solution remained colorless. After drying, the dye was eluted with 10 mM Tris-HCl, pH8.5, and absorbance was measured either at 550 or 492 nm for lower and higher cell densities, respectively. The average absorbance of the sample representing the day 1 starting cell number was subtracted from the absorbance values of the WE-treated cells.

IL-1β levels were determined with a commercial ELISA kit. The amount of IL-1β contained in the wound exudate added to the cells was subtracted from the total IL-B in the supernatants in order to determine the cytokine secreted by the cells.

All experiments were carried out in triplicate for each sample and concentration, and means±standard deviation (SD) were used for the evaluation of the experiment. Results are expressed as percentage of control values for unstimulated cells.

The table in FIG. 15 shows the effects of 1 μM mapracorat on fibroblast proliferation in the presence of a high number of different wound exudates from chronic, non-healing skin wound of human patients. The level of proliferation in the presence of the respective WE was set to 100%, and formed the basis for the calculation of the effect of mapracorat. All values >120% (mean of WE control+2 SD) are considered growth promoting.

Further results are shown in Table 1 below:

TABLE 1

| | WE | AZD1594 |
|---|---|---|
| WE-04 | 100 | 1139 |
| WE-05 | 100 | 203 |
| WE-37 | 100 | 171 |
| WE-03 | 100 | 161 |

TABLE 1-continued

| | WE | AZD1594 |
|---|---|---|
| WE-02 | 100 | 196 |
| WE-77 | 100 | 128 |

The table shows the effects of 1 μM AZD7594 on fibroblast proliferation in the presence of a plurality of different wound exudates. The level of proliferation in the presence of the respective WE was set to 100%, and formed the basis for the calculation of the effect of AZD7594, which are given in % proliferation of respective WE controls. All values >120% (mean of WE control+2 SD) are considered growth promoting. The efficacy of AZD7594 was comparable to the effect of mapracorat (cf. FIG. 15).

Example 1.2: Measuring the Fibroblast-Derived Matrix Formation (FDM) by Fibroblast Cells: Measuring the Fibroblast-Derived Matrix Formation by Fibroblast Cells in the Presence of a Wound Exudate Sample Obtained from a Skin Wound, in Particular Chronic Human Skin Wound Human dermal fibroblast (HDF) cells were seeded at 1250 cells/well on day −3 into 384-well tissue culture plates, which had been pre-coated for 1 hour at 37° C. with 0.2% gelatin solution (Sigma). When the cells reached confluence (=day 0), a matrix promoting supplement (vitamin C: 2-phospho-L-ascorbic acid trisodium salt, 100 μg/ml; Sigma) was added together with test samples containing TGF-β1 or graded concentrations of compounds −/+WE as described for the HDF proliferation assay. After 4 days, medium was replaced by fresh vitamin C—and stimulus—as well as compound-containing medium, maintaining the conditions initiated on day 0. TGF-β1 was included as a positive control to promote FDM formation. After a total incubation time of 7 to 8 days, FDM production was measured in fixed cultures via SRB staining and evaluated as described above. In some cases, the experiment was stopped and evaluated already on day 4.

Experimental results are for example shown in FIG. 12. FIG. 12 shows the effect of a plurality of SEGRM in 3D fibroblast culture with WE from patient #92. AZD7594 was the most active of the SEGRM tested in 3D culture, followed by mapracorat and BI653048. This is in line with their potencies for glucocorticoid receptor activation (EC50 values of 0.9 nM, 1.9 nM and 55 nM, respectively). The inactive BI3047, which is not a SEGRM, did not induce matrix formation.

Example 1.3: Keratinocyte Proliferation Assay: Measuring the Proliferation of Keratinocyte Cells in the Presence of a Wound Exudate Sample Obtained from a Skin Wound, in Particular Chronic Human Skin Wound The HaCaT keratinocyte cell line was routinely cultured in DMEM containing 10% FCS, 2 mM glutamine, and 100 U/ml penicillin/100 μg/ml streptomycin. The proliferation assay was carried out as described for HDF cells. Primary human keratinocytes were grown in KBM medium (Lonza) containing 0.06 mM calcium and supplemented with growth factors (Lonza) on plastic coated with rat tail collagen (40 μg/ml; Gibco) or gelatin (0.2%; Sigma). No antibiotics were used. The proliferation assay was carried out as described for HDF cells.

Example 1.4: Primary Human Macrophage Stimulation Assay: Measuring Cytokine Production Primary human macrophages were differentiated from monocytes, which had been isolated from peripheral blood mononuclear cells (PBMC). PBMC were isolated from buffy coats obtained from the Red Cross, Vienna, using LymphoPrep (Technoclone). 30 ml of buffy concentrate was diluted 1:2 with PBS, gently underlayered with 15 ml Lymphoprep in a 50 ml Falcon tube and centrifuged for 25 minutes at 1800 rpm at 21° C. The interphase was carefully transferred to a new Falcon tube and filled up to 50 ml with ice cold PBS. After another centrifugation step (10 minutes, 1200 rpm, 4° C.), the cell pellet was washed 3 times with PBS, resuspended in RPMI medium containing 20% FCS and 10% DMSO and frozen in liquid nitrogen. Monocytes were generated from frozen aliquots using positive selection with the CD14 Beads-Kit (Miltenyi) on an autoMACS-Sorter (Miltenyi) according to the manufacturer's instructions.

For culture and differentiation into macrophages, monocytes were seeded at 3-5×$10^6$ monocytes/well in 6-well-plates (Nunc) and incubated with 20 ng/ml M-CSF (R&D Systems) in RPMI supplemented with 10% FCS, 2 mM glutamine, and 100 U/ml penicillin/100 μg/ml streptomycin in a total volume of 5 ml per well. After 2 days, 2 ml of the supernatant were removed and replaced by 2.5 ml/well of fresh medium containing 20 ng/ml M-CSF. On the third day, microscopic examination revealed differentiation into adherent, frequently elongated cells.

The macrophages were harvested and re-seeded in 200 μl or 50 μl serum-free medium on 96-well or 384-well plates, respectively, combining cells with graded concentrations of test compounds in the absence or presence of various dilutions of sterile-filtered WE.

A combination of 100 ng/ml LPS (Sigma) and 50 ng/ml IFN-γ (PeproTech) served as positive control for the induction of cytokine secretion. For negative control samples, medium was added instead of specific stimuli.

After 24 hours, the supernatants were transferred to fresh plates and frozen at −20° C. for future cytokine analysis (IL-1α, IL-1β, TNF-α). The cytokine concentrations of the input WE were subtracted from the supernatant levels in order to calculate WE-induced cytokine stimulation.

Example 1.5: Human Monocyte-Dermal Fibroblast Co-Cultures as In Vitro Models that Reflect Macrophage Behavior in Human Skin measuring (a) the amount(s) of one or more M1 marker(s) and one or more M2 marker(s) in the supernatant of macrophages incubated with a wound exudate sample obtained from a skin wound, wherein the macrophages are in co-culture with fibroblasts, and (b) measuring the amount(s) and/or frequency distribution(s) of one or more M1 cell surface marker(s) and one or more M2 cell surface marker(s) on macrophages incubated with a wound exudate sample obtained from a skin wound, wherein the macrophages are in co-culture with fibroblasts, (c) measuring the expression level(s) of one or more M1 marker mRNA(s) and one or more M2 marker mRNA(s) in macrophages incubated with a wound exudate sample obtained from a skin wound, wherein the macrophages are in co-culture with fibroblasts and (d) the amount(s) of one or more cytokine markers selected from IL-1alpha, IL-1beta and TNF-alpha in the supernatant of macrophages incubated with a wound exudate sample obtained from a skin wound, wherein the macrophages are in co-culture with fibroblasts CD14+ monocytes, isolated from PBMC of healthy donors by magnetic bead separation were incubated either alone or in the presence of primary human dermal fibroblasts (CellNTec) or fibroblast-derived matrices (FDM). FDM had been generated from primary human dermal fibroblasts by a 3-week incubation with the growth supplements vitamin C or insulin and EGF (vitamin C: 2-phospho-L-ascorbic acid trisodium salt, 100 μg/ml; human EGF, 5 ng/ml; human insulin, 5 μg/ml). Alternatively, fibroblast monolayer cultures can be used as well. After 4 days to a week to allow for macrophage differentiation in the presence or absence of M-CSF (25 ng/ml), the cultures were stimulated overnight with graded concentrations of test compounds in the absence or presence of various dilutions of sterile-filtered WE. IFN-γ (50 ng/ml), LPS (100 ng/ml) and IL-4 (25 ng/ml) or combinations thereof served as controls for M1 and M2 macrophage induction. For negative control samples, medium was added instead of specific stimuli. WE with and without compounds were added to the culture medium for overnight stimulation at dilutions ranging from 1:25 to 1:100.

Supernatants were harvested and frozen for cytokine determination by ELISA, and cells were harvested and subjected to FACS analysis, gating on the monocyte population. Geometric means or mean fluorescence intensities (MFI) were used to quantify surface marker expression.

There are 2 possibilities for evaluation: a) the % of cells positive for a given marker within a population, which is the most commonly used readout in FACS analysis, or b) the quantity of cell surface expression (as surrogate for the number of labelled molecules on the cell surface per individual cell), as measured by the mean fluorescence intensity.

Specific mRNA levels are determined as ratios compared to a housekeeping gene; the values obtained are "expression relative to housekeeping gene".

The following readouts were used:

- FACS: CD38, CD64 and CD197 for M1 macrophages, CD200 receptor (CD200R), CD206 and CD209 for M2 macrophages, CD163 as a marker of macrophage differentiation. Ratios of M1/M2 cell surface marker expression were calculated.
- ELISA: CXCL10 and IL-23p19 for M1 macrophages and CCL22 and CCL18 as M2 macrophage markers, IL-1alpha, IL-1beta and TNF-alpha as pro-inflammatory markers indicative of an M1 phenotype.
- mRNA: CD38, CD64 CD38, CD64 and CD197 for M1 macrophages, CD200 receptor (CD200R), CD206 and CD209 for M2 macrophages, CD163 as a marker of macrophage differentiation.

Example 1.6: Determination of CCL18

CCL18 in WE and in macrophage supernatants was determined in F96 Maxisorp Nunc Immuno plates (Nunc, #439454) using the hCCL18/PARC DuoSet ELISA Kit from R&D Systems (#DY394) according to the manufacturer's instructions. Enzyme reaction and measurement were performed as described for IL-1a.

Example 1.7: Analysis of Macrophage Surface Markers by Flow Cytometry

Cells were harvested and resuspended in FACS buffer (PBS containing 2% FCS). Unspecific antibody binding was prevented by incubation with human Trustain FCR blocking solution (Biolegend, #422302) on ice for 10 minutes. The following fluorchrome-conjugated antibodies from eBioscience (now ThermoFisher Scientific) were used to detect specific surface markers by staining on ice for 30 minutes: CD38-PerCPeFluor710 (#46-0388-42), CD197-APC (#17-1979-42), CD206-AF488 (#53-2069-42), CD209-PerCP Cy5.5 (#45-2099-42). Co-staining with CD45 eFluor (#506 69-0459-42) was used to distinguish macrophages from primary human fibroblasts when analyzed from co-cultures. After washing cells with FACS buffer, they were fixed with 1% paraformaldehyde in PBS and stored at 4° C. in the dark until data were acquired on a Gallios flow cytometer from Beckman Coulter and analyzed with the Kaluza analysis software 1.3.

Example 1.8: Analysis of mRNA Expression in Fibroblast Cultures

Cells were seeded into 24-well plates and incubated with compounds in the presence or absence of wound exudates for 72 hours. Total RNA was isolated using the RNeasy Mini Kit (QIAGEN #74106) according to the manufacturer's protocol. RNA integrity and concentration for each sample was confirmed and measured with the Qubit fluorometer. Each RNA sample was then diluted to 2 ng/μl in nuclease-free doubly distilled water.

20 ng of total RNA were reverse-transcribed into cDNA and immediately subjected to PCR amplification using the SuperScript Ill Platinum One-Step Quantitative RT-PCR System with ROX (Invitrogen #11745). qRT-PCR amplifications were performed in 20 μl reactions containing 9 μl 2× Reaction Mix with ROX, 0.4 μl SuperScript III RT/Platinum Taq Mix and 1 μl primer (final: 900 nM, Taqman Gene Expression Assay, Applied Biosystems)

The program included 30 minutes of reverse transcription at 48° C., an initial denaturation for 5 minutes at 95° C. followed by 40 cycles of denaturation at 95° C. for 15 seconds and annealing at 60° C. for 60 seconds. Reactions were set up in 96-well format PCR plates (Peqlab #732-2879) and carried out in a Mx3005P Real-Time PCR Detection System (Stratagene).

TaqMan Gene Expression Assays (Applied Biosystems) were used, which include preoptimized probe and primer sets specific for the genes being validated. The sequences and ID numbers are listed below:

```
EF1a
                                        (SEQ ID NO: 1)
AAGTGCTAACATGCCTTGGTTCAAG Hs00265885_g1

Collagen 1a
                                        (SEQ ID NO: 2)
AAGACGAAGACATCCCACCAATCAC Hs00164004_m1

Collagen 3a
                                        (SEQ ID NO: 3)
GAACTCAAGAGTGGAGAATACTGGG Hs00943809_m1

IL1β
                                        (SEQ ID NO: 4)
CAGATGAAGTGCTCCTTCCAGGACC Hs01555410_m1
```

The house keeping gene elongation factor 1a (EF1a) was used as a reference gene. Normalized expression was calculated using the comparative Ct (or ΔCt) method, and fold changes were derived from the 2-ΔΔCt values for each gene. Graphs were prepared using relative Ct values that were calculated by subtracting the EF1a Ct values from the corresponding Ct values for the gene being measured.

Example 1.9: Delayed Wound Healing in a Pig Model

The animal experiments were approved by governmental authorities. Two young farm pigs (10-12 kg) were anesthetized and full-thickness excisional wounds were developed using a 6 mm biopsy punch. During the first 5 days after wounding, the wounds were stimulated with a) 0.05% R848 (resiquimod) and 50 μl human wound exudate, b) 0.05% R848 and human serum or c) human serum alone. R848 was applied in the mornings and exudate and serum 6 hours later, in 50 μl of solutions gelified by the addition of 2% HPMC. On days 6-10, wounds were treated once daily with mapracorat or vehicle (50% PG/47.5% $H_2O$/0.5% Tween 80/2% HPMC). The wounds were clinically scored daily. The total wound score (maximum score=21) consisted of wound appearance (dry vs. moist), size, wound content, pus, crust, erythema intensity, erythema width, swelling and necrosis. Reported values are individual values for each of the 2 pigs.

Example 1.10: Translocation of the Glucocorticoid Receptor from the Cytoplasm into the Nucleus in Primary Human Fibroblasts Primary human fibroblasts were seeded into 384-well plates, as described in Example 1.1., using 2500 cells/well in a total volume of 50 μl. After adherence for 24 hours, the cells were serum-starved overnight and then incubated for 45 minutes at 37° C. with graded concentrations of SEGRMs or corticosteroids as positive controls. The cells were then fixed with 4% paraformaldehyde for 10 minutes at room temperature, followed by permeabilization with 0.5% Triton X100 in PBS in 1% BSA, for 10 minutes at room temperature. They were stained with a mouse-anti-glucocorticoid receptor monoclonal antibody (CellSignaling #47411) or mouse IgG1-kappa isotype control (e-Bioscience #14-4714) and developed with Alexa Fluor donkey-anti-mouse IgG (Molecular Probes #A21202). Cells were examined in on Olympus CKX53 fluorescence microscope and evaluated based on the localization of the glucocorticoid receptor: predominantly nuclear (N), nuclear+cytoplasmic (N/C) or predominantly cytoplasmic (C).

The results are shown in Table 2 below:

TABLE 2

| | 100 nM | 10 nm | 1 nM | 0.1 nM |
|---|---|---|---|---|
| AZD7594 | N | N | N | N/C |
| CORT108297 | N | N | N/C | C |
| HY14234 | N | N | N | N/C |
| Mapracorat | N | N | N | N/C |
| ZK216348 | N | N | N | N/C |
| BI-353048 | N | N | N | C |
| BI3047 | C/N | C | C | C |

The table shows the translocation of the glucocorticoid receptor from the cytoplasm (C) of fibroblasts into the nucleus (N) as a measure of activity. The cells were incubated with graded compound concentrations and intracellular glucocorticoid receptor localization was determined by indirect immunofluorescence, using an antibody directed against the receptor. The localization of the glucocorticoid receptor at compound concentrations ranging from 0.1 to 100 nM is indicated by N (nucleus), N/C (nucleus >cytoplasm), C/N (cytoplasm >nucleus) and C (cytoplasm).

Example 1.11: Primary Human Monocyte Cytokine Secretion Assay

Primary human monocytes were prepared from peripheral blood mononuclear cells (PBMC). PBMC were isolated from buffy coats obtained from the Red Cross, Vienna, using LymphoPrep (Technoclone). 30 ml of buffy concentrate was diluted 1:2 with PBS, gently underlayered with 15 ml Lymphoprep in a 50 ml Falcon tube and centrifuged for 25 minutes at 1800 rpm at 21° C. The interphase was carefully transferred to a new Falcon tube and filled up to 50 ml with ice cold PBS. After another centrifugation step (10 minutes, 1200 rpm, 4° C.), the cell pellet was washed 3 times with PBS, resuspended in RPMI medium containing 20% FCS and 10% DMSO and frozen in liquid nitrogen. Monocytes were generated from frozen aliquots using positive selection with the CD14 Beads-Kit (Miltenyi) on an autoMACS-Sorter (Miltenyi) according to the manufacturer's instructions.

Cells were seeded at $8\times10^5$/ml in 50 μl/well of a 384-well plate and combined cells with graded concentrations of test compounds. After 16 hours, the supernatants were transferred to fresh plates and frozen at −20° C. for IL-8 analysis, using a commercial ELISA kit.

Example 1.12: U937 Cell Stimulation Assay

The human monocytic cell line U937 (ATCC CRL 1593) was routinely grown in RPMI_1640 supplemented by 10% FCS and 2 mM glutamine, and 100 U/ml penicillin/100 μg/ml streptomycin. Cells were seeded at $4\times10^5$/ml in 50 μl/well of a 384-well plate and combined cells with graded concentrations of test compounds and LPS at 100 ng/ml. After 16 hours, the supernatants were transferred to fresh plates and frozen at −20° C. for IL-8 analysis, using a commercial ELISA kit.

Wound Exudates

Wound exudates (WE) from venous, arterial, pressure and diabetic ulcers as well as surgical wounds were harvested either in gel-free containers after negative pressure therapy or by swabbing with Nylon-flocked swabs (Copan #502CS01). Informed patient consent had been obtained according to the Declaration of Helsinki.

Test Compounds

Low molecular weight compounds (see list in Table 3) were dissolved in DMSO (Bioreagent for cell culture, Sigma) at 10 mM or 100 mM and diluted at least 1:1000 in medium for cellular assays (final DMSO concentration 50.1%). Compounds were typically tested in logarithmic (1:10) or half-logarithmic (1:3.33) dilution series, starting at 10 μM or 100 μM as the highest compound concentration.

Cells were incubated with compounds for 72 hours in proliferation assays and up to 8 days for FDM assay (refreshed after 4 days). When compounds were tested for their effect on WE stimulation, the incubation of cells with compounds was started and ended simultaneously with WE-incubation.

TABLE 3

List of low molecular weight compounds for cellular assays

| Compound | Source |
|---|---|
| Dexamethasone 21-acetate | Sigma-Aldrich |
| BI-653048 | Boehringer Ingelheim |
| BI-3047 | Boehringer Ingelhelm |
| Mifepristone | MedChem Express |
| Prednisolone | Sigma-Aldrich |
| Mapracorat | MedChem Express |
| ZK216348 | Axon Medchem |
| HY14234 | MedChem Express |
| AZD7594 | MedChem Express |

The invention claimed is:

1. A method of treating impaired skin wound healing in a subject, the method comprising administering to a subject in need thereof an effective amount of a Selective Glucocorticoid Receptor Modulator (SEGRM), or a pharmaceutically acceptable salt thereof, thereby treating impaired skin wound healing in the subject, wherein the SEGRM is selected from the group consisting of:

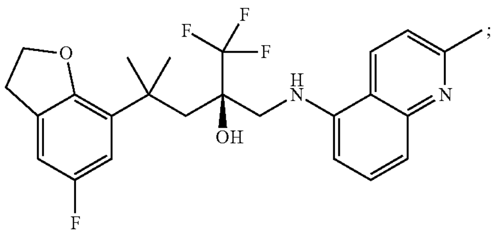

-continued

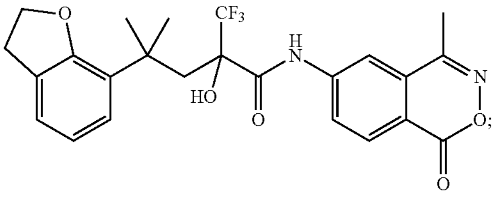

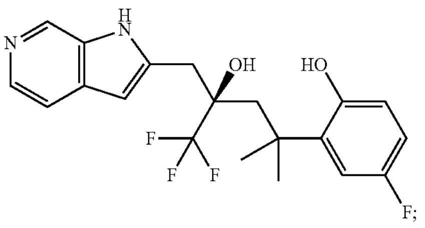 [SMILES: CC(C)(C[C@@](O)(Cc1cc2ccncc2[nH]1)C(F)(F)F)c1cc(F)ccc1O]

(R)-2-(4-((5-(Ethylsulfonyl)-1H-pyrrolo[2,3-c]pyridin-2-yl)methyl)-5,5,5-trifluoro-4-hydroxy-2-methylpentan-2-yl)-5-fluorobenzamide; and

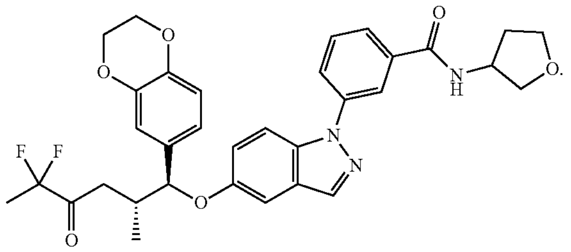 [SMILES: C[C@H](CC(=O)C(C)(F)F)[C@H](Oc1ccc2c(cnn2-c2cccc(C(=O)NC3CCOC3)c2)c1)c1ccc2c(c1)OCCO2]

2. The method of claim 1, wherein the impaired skin wound is selected from a skin wound which is infected by at least one microorganism, is caused by a bullous skin disease, is an ischemic wound, a venous ulcer, an arterial ulcer, a mixed ulcer, a pressure ulcer, a neuropathic wound, an ulcus cruris, a surgical wound, a burn, a dehiscence, a neoplastic ulcer, or a rare ulcer.

3. The method of claim 1, wherein the subject suffers from at least one co-morbidity associated with impaired skin wound healing, and/or wherein the subject is treated with at least one immunosuppressive drug.

4. The method of claim 3, wherein the at least one co-morbidity is diabetes.

5. The method of claim 1, wherein the subject suffers from diabetes.

6. The method of claim 1, wherein the Selective Glucocorticoid Receptor Modulator (SEGRM), or pharmaceutically acceptable salt thereof is (i) formulated for systemic administration, or (ii) formulated for local administration.

7. The method of claim 6, wherein the Selective Glucocorticoid Receptor Modulator (SEGRM), or pharmaceutically acceptable salt thereof is formulated for local administration, wherein said formulation comprises at least one Selective Glucocorticoid Receptor Modulator (SEGRM) and a) oleyl alcohol, b) cetearyl octanoate and c) a vegetable oil.

8. The method of claim 1, wherein the impaired skin wound is a diabetic ulcer, ulcus cruris arteriosum, or is caused by epidermolysis bullosa.

9. The method of claim 1, wherein the impaired skin wound is caused by diabetes in a diabetic patient.

10. The method of claim 1, wherein the subject has at least one diabetic ulcer.

11. The method of claim 1, wherein the subject has undergone transplantation of a graft.

12. The method of claim 1, wherein the subject is undergoing immunosuppressive therapy and optionally suffers from diabetes.

13. The method of claim 1, wherein the Selective Glucocorticoid Receptor Modulator (SEGRM), or pharmaceutically acceptable salt thereof is formulated for oral or intravenous administration.

14. The method of claim 1, wherein the Selective Glucocorticoid Receptor Modulator (SEGRM), or pharmaceutically acceptable salt thereof is formulated for topical, mucosal, ocular, intradermal, or subcutaneous administration.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: EF1a probe

<400> SEQUENCE: 1
aagtgctaac atgccttggt tcaag 25

<210> SEQ ID NO 2
<211> LENGTH: 25
<212> TYPE: DNA
<213> ORGANISM: Artificial Sequence
<220> FEATURE:
<223> OTHER INFORMATION: Collagen 1a probe

<400> SEQUENCE: 2
aagacgaaga catcccacca atcac 25

<210> SEQ ID NO 3
<211> LENGTH: 25
<212> TYPE: DNA
<213> ORGANISM: Artificial Sequence
<220> FEATURE:
<223> OTHER INFORMATION: Collagen 3a probe

<400> SEQUENCE: 3
gaactcaaga gtggagaata ctggg 25

<210> SEQ ID NO 4
<211> LENGTH: 25
<212> TYPE: DNA
<213> ORGANISM: Artificial Sequence
<220> FEATURE:
<223> OTHER INFORMATION: IL1 probe

<400> SEQUENCE: 4
cagatgaagt gctccttcca ggacc 25